US006245805B1

(12) United States Patent
Broder et al.

(10) Patent No.: US 6,245,805 B1
(45) Date of Patent: *Jun. 12, 2001

(54) METHOD, COMPOSITIONS AND KITS FOR INCREASING THE ORAL BIOAVAILABILITY OF PHARMACEUTICAL AGENTS

(75) Inventors: Samuel Broder, Weston; Kenneth L. Duchin, Fort Lauderdale, both of FL (US); Sami Selim, Irvine, CA (US)

(73) Assignee: Baker Norton Pharmaceuticals, Inc., Miami, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 08/733,142

(22) Filed: Oct. 16, 1996

Related U.S. Application Data

(63) Continuation-in-part of application No. 08/608,776, filed on Feb. 29, 1996, now Pat. No. 5,968,972.
(60) Provisional application No. 60/007,071, filed on Oct. 26, 1995.

(51) Int. Cl.[7] .................................................. A01N 43/02

(52) U.S. Cl. ........................................ 514/449; 514/449

(58) Field of Search ...................................... 514/11, 449

(56) References Cited

U.S. PATENT DOCUMENTS

| 5,114,951 | 5/1992 | King ........................... 514/290 |
| 5,118,493 | 6/1992 | Kelley et al. ................. 424/10 |
| 5,124,330 | 6/1992 | King ........................... 514/250 |
| 5,124,338 | 6/1992 | King ........................... 514/343 |
| 5,124,339 | 6/1992 | King ........................... 514/352 |
| 5,166,207 | 11/1992 | Smith .......................... 514/270 |
| 5,208,238 | 5/1993 | King ........................... 514/255 |
| 5,300,282 | 4/1994 | King ........................... 424/10 |
| 5,346,897 | 9/1994 | King ........................... 514/290 |
| 5,364,843 | 11/1994 | King ........................... 514/15 |
| 5,387,685 | 2/1995 | Powell et al. .................. 546/143 |
| 5,395,610 | 3/1995 | King ........................... 424/10 |
| 5,416,091 | 5/1995 | King ........................... 514/290 |
| 5,646,176 | 7/1997 | Golik et al. ................... 514/444 |
| 5,972,992 | 10/1999 | Carver et al. .................. 514/449 |
| 6,004,927 | 12/1999 | Benet et al. ................... 514/9 |
| 6,096,331 | 8/2000 | Desai et al. ................... 424/422 |

FOREIGN PATENT DOCUMENTS

WO 92/12132   7/1992   (WO).
WO 95/20980   8/1995   (WO).

OTHER PUBLICATIONS

Benet et al., *J. Cont. Release*, vol. 39, pp. 139–143 (1996).
Brock et al., *Cancer Res.*, vol. 55, pp. 459–462 (1995).
Wils et al., *Biochem. Pharm.*, vol. 48, pp. 1528–1530 (1994).
Chang et al., Clin. Pharm. Therap., vol. 59, pp. 297–303 (1996).
Chiu et al., Proc. of Am. Assoc. Pharm. Sci., Abstract PDD 7428 (Nov. 1995).
Bal et al., Proc. of Am. Assoc. Pharm. Sci., Abstract PDD 7459 (Nov. 1995).
Germann et al., J. Bioenerg. Biomemb., vol. 27, pp. 53–61 (1995).
Joel et al., Cancer Chemother. Pharmac., vol. 37, pp. 125–133 (1995).
Schinkel et al., J. Clin. Invest., vol. 96, pp. 1698–1705 (1995).
Scheffer et al., Nature Medicine, vol. 1, No. 6, pp. 578–582 (1995).
Lum et al., Drug Resistance in Clin. Onc. and Hematology, vol. 9, No. 2, pp. 319–336 (1995).
Fracasso et al., Proc. of ASCO, vol. 14, Abstract 1585, p. 486 (1995).
Bissery, Euro. J. Cancer, vol. 31A, Sup. 4, pp. S1–S6 (1995).
Leu et al., Cancer Chem. Pharmac., vol. 35, No. 5, pp. 432–436 (1995).
Keogh et al., N.E. J. Med., vol. 333, No. 10, pp. 628–633 (1995).
Levêque et al., Anticancer Res. vol. 15, pp. 331–336 (1995).
Montaseri et al., Pharm. Res., vol. 12, No. 9, p. S–429, Abstract PPDM 8411 (1995).
Muller, Proc. Nat. Acad. Sci., vol. 91, pp. 13033–13037 (1994).
Pouvelle et al., J. Clin. Invest., vol. 94, pp. 413–417 (1994).
Schinkel et al., Cell, vol. 77, pp. 491–502 (1994).
Fisher et al., Proc. of ASCO, vol. 13, Abstract 369, p. 144 (1994).
Siegsmund et al., J. Urol., vol. 151, pp. 485–491 (1994).

(List continued on next page.)

*Primary Examiner*—Richard L. Raymond
(74) *Attorney, Agent, or Firm*—Lerner, David, Littenberg, Krumholz & Mentlik, LLP

(57) ABSTRACT

A method of increasing the bioavailability upon oral administration of a pharmacologically active target agent, particularly an antitumor or antineoplastic agent which exhibits poor or inconsistent oral bioavailability (e.g., paclitaxel, docetaxel or etoposide), comprises the oral co-administration to a mammalian patient of the target agent and an oral bioavailability-enhancing agent (e.g., cyclosporin A, cyclosporin D, cyclosporin F or ketoconazole). The enhancing agent may be administered orally from 0.5–24 hrs. prior to the oral administration of one or more doses of the target agent, substantially simultaneously with the target agent or both prior to and substantially simultaneously with the target agent. A method of treating mammalian patients suffering from diseases responsive to target agents with poor oral bioavailability, as well as oral dosage forms containing such target agents, combination oral dosage forms containing bioavailability-enhancing agents and target agents and kits containing enhancing and target agent dosage forms and dosing information for the co-administration of the same are also disclosed.

53 Claims, 46 Drawing Sheets

OTHER PUBLICATIONS

Grant et al., Cancer Res., vol. 54, pp. 357–361 (1994).
Cresteil et al., Cancer Res., vol. 54, pp. 386–392 (1994).
Bartlett et al., J. Clin. Onc., vol. 12, No. 4, pp. 835–842 (1994).
Sikic et al., Anticancer Drug Resistance: Adv. Molec. Clin. Res. pp. 149–165 (1994).
Kumar et al., J. of Pharmac. and Exp. Therapeutics, vol. 268, No. 3, pp. 1160–1165 (1994).
Lepage et al., Current Op. in Neph. and Hypert., vol. 2, pp. 735–743 (1993).

Lum et al., J. Clin. Onc., vol. 10, No. 10, pp. 1635–1642 (1992).

Loehrer, Seminars in Onc., vol. 18, No. 6, Sup. 14, pp. 48–52 (1992).

Keller et al., Int. J. Cancer, vol. 51, pp. 433–438 (1992).

Hunter, et al., Pharm. Res. 10(5):743–749 (1993).

Kobayashi, Proc. Annu. Meet. Am. Soc. Clin. Oncol., 15:A1489 (1996).

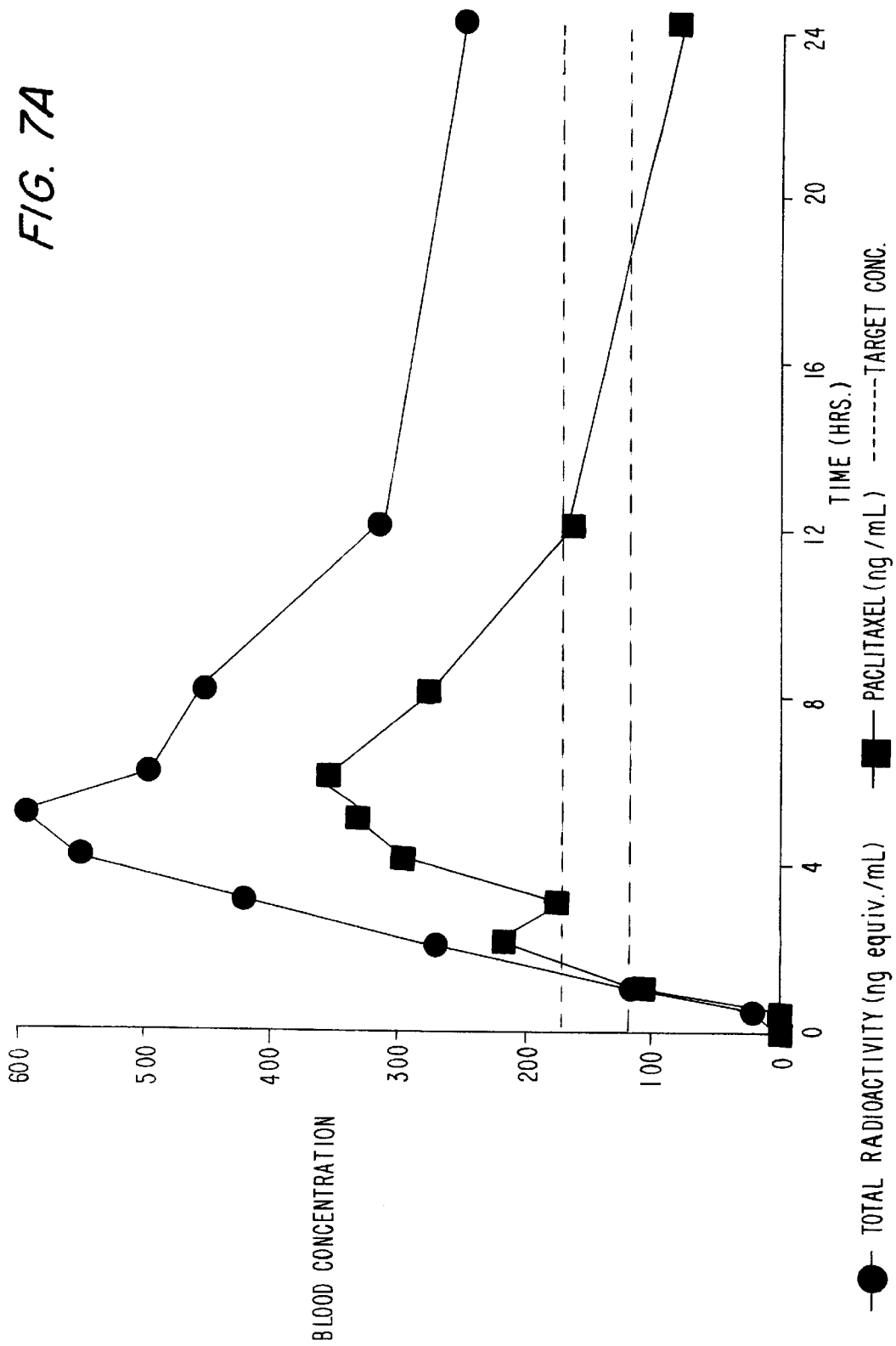

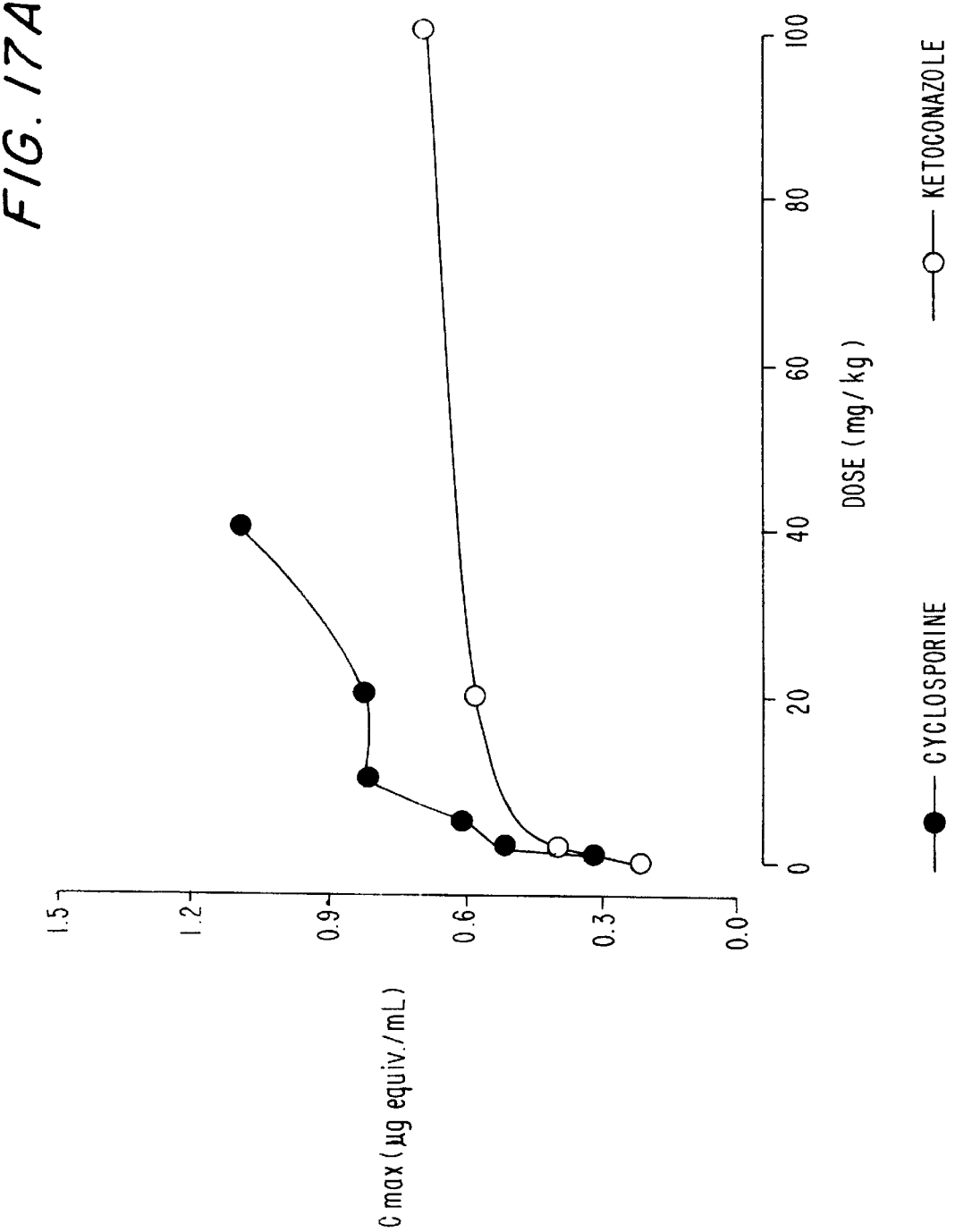

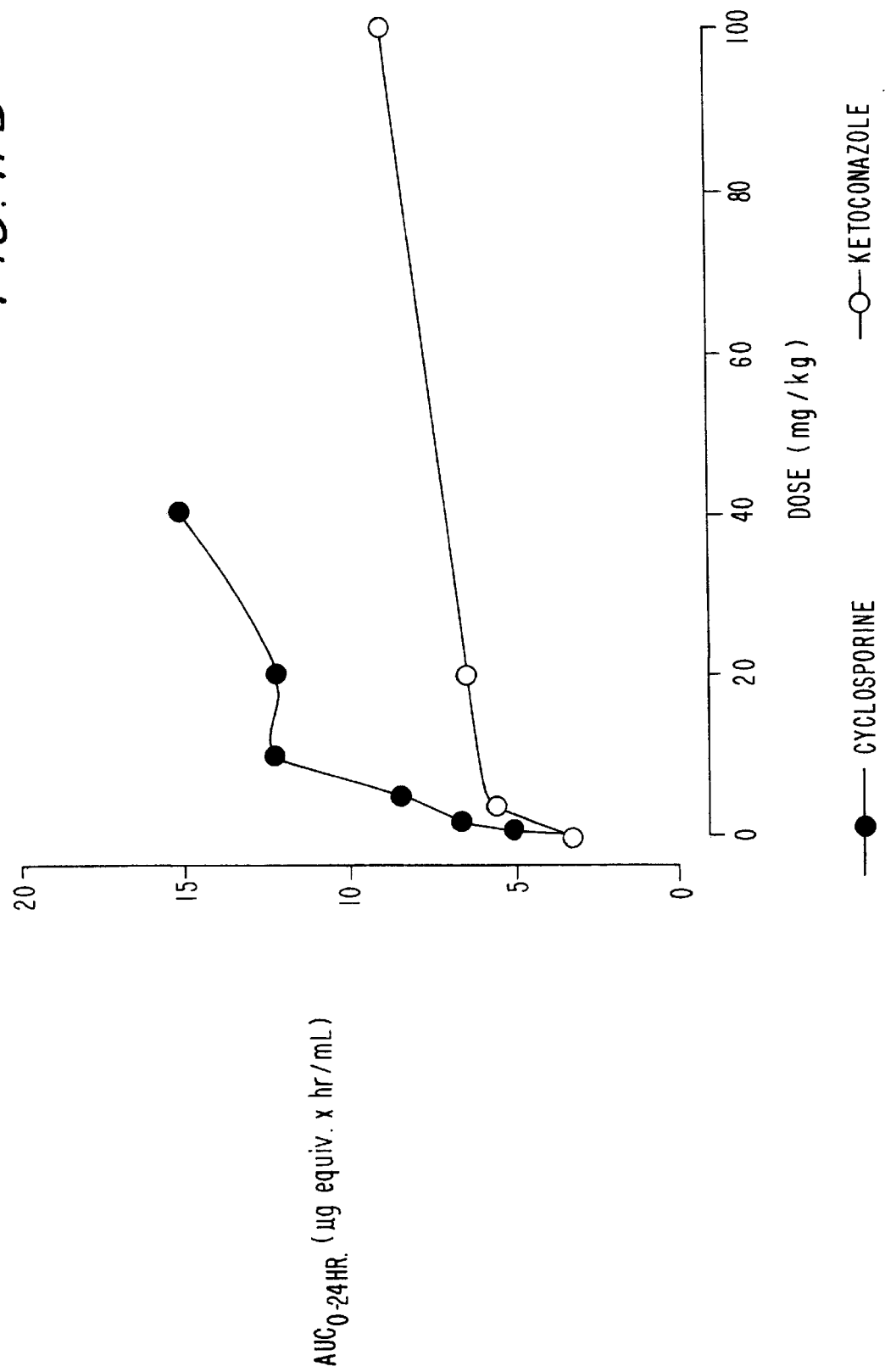

METHOD, COMPOSITIONS AND KITS FOR INCREASING THE ORAL BIOAVAILABILITY OF PHARMACEUTICAL AGENTS

CROSS-REFERENCE TO RELATED APPLICATIONS

This application is a continuation-in-part of application Ser. No. 08/608,776, filed Feb. 29, 1996, now U.S. Pat. No. 5,968,972, which claims the priority of provisional application Ser. No. 60/007,071, filed Oct. 26, 1995.

REFERENCE TO DISCLOSURE DOCUMENTS

This application incorporates material included in Disclosure Document No. 377063, filed Jun. 23, 1995, No. 386504, filed Dec. 11, 1995, No. 391109, filed Feb. 7, 1996, and No. 391228, filed Feb. 7, 1996.

BACKGROUND OF THE INVENTION

1. Field of the Invention

The invention relates to methods, compositions and kits for improving the oral bioavailability of pharmaceutical agents that are poorly absorbed from the gastrointestinal tract, and to methods of treatment of patients through the oral administration of such agents. One aspect of the invention relates to the use of cyclosporins to enhance the oral bioavailability of paclitaxel and related taxanes.

2. Description of the Prior Art

Many valuable pharmacologically active compounds cannot be effectively administered by the oral route because of poor systemic absorption from the gastrointestinal tract. All these pharmaceutical agents are, therefore, generally administered via intravenous or intramuscular routes, requiring intervention by a physician or other health care professional, entailing considerable discomfort and potential local trauma to the patient and even requiring administration in a hospital setting with surgical access in the case of certain IV infusions.

It has been speculated that, in some cases, the poor bioavailability of a drug after oral administration is a result of the activity of a multidrug transporter, a membrane-bound P-glycoprotein, which functions as an energy-dependent transport or efflux pump to decrease intracellular accumulation of drug by extruding xenobiotics from the cell. This P-glycoprotein has been identified in normal tissues of secretory endothelium, such as the biliary lining, brush border of the proximal tubule in the kidney and luminal surface of the intestine, and vascular endothelial cells lining the blood brain barrier, placenta and testis.

It is believed that the P-glycoprotein efflux pump prevents certain pharmaceutical compounds from transversing the mucosal cells of the small intestine and, therefore, from being absorbed into the systemic circulation. A number of known non-cytotoxic pharmacological agents have been shown to inhibit P-glycoprotein, including cyclosporin A (also known as cyclosporine), verapamil, tamoxifen, quinidine and phenothiazines, among others. Many of these studies were aimed at achieving greater accumulation of cytotoxic drugs inside tumor cells. In fact, clinical trials have been conducted to study the effects of cyclosporine on the pharmacokinetics and toxicities of paclitaxel (Fisher et al., *Proc. Am. Soc. Clin. Oncol.*, 13: 143, 1994); doxorubicin (Bartlett et al., *J. Clin. Onc.* 12:835–842, 1994); and etoposide (Lum et al., *J. Clin. Onc.* 10:1635-42, 1992), all of which are anti-cancer agents known to be subject to multidrug resistance (MDR). These trials showed that patients receiving intravenous cyclosporine prior to or together with the anti-cancer drugs had higher blood levels of those drugs, presumably through reduced body clearance, and exhibited the expected toxicity at substantially lower dosage levels. These findings tended to indicate that the concomitant administration of cyclosporine suppressed the MDR action of P-glycoprotein, enabling larger intracellular accumulations of the therapeutic agents. For a general discussion of the pharmacologic implications for the clinical use of P-glycoprotein inhibitors, see Lum et al., *Drug Resist. Clin. Onc. Hemat.*, 9: 319–336 (1995); Schinkel et al., *Eur. J. Cancer*, 31A: 1295–1298 (1995).

In the aforedescribed studies relating to the use of cyclosporine to increase the blood levels of pharmaceutical agents subject to P-glycoprotein mediated resistance, the active agents and the cyclosporine were administered intravenously. No suggestion was made in these publications that cyclosporine or other substances believed to inhibit the P-glycoprotein efflux pump could be orally administered to substantially increase the bioavailability of orally administered anti-cancer drugs and other pharmaceutical agents which are themselves poorly absorbed from the gut without producing highly toxic side effects. Indeed, in the 1995 review paper cited above, Lum et al. showed that concomitant IV administration of MDR inhibitors and chemotherapeutic agents subject to MDR increased toxicity levels and exacerbated the patients' serious side effects. Schinkel et al. briefly adverted to the fact that MDR1 and P-glycoprotein are abundant in the mucosal cells of the intestine, and that this may affect the oral bioavailability of P-glycoprotein substrate drugs, but did not suggest or imply that the oral administration of MDR suppressing agents could improve the bioavailability of the orally unavailable agents. Furthermore, like Lum et al., Schinkel et al. warned that P-glycoprotein inhibitors can dramatically increase toxicity in chemotherapy patients and should, therefore, be used cautiously.

In an earlier publication, Schinkel et al. showed that absorption of orally ingested ivermectin was increased in mice homozygous for a disruption of the MDR1 a gene in comparison with normal mice, demonstrating that P-glycoprotein played a major role in reducing the bioavailability of this agent (*Cell* 77: 491–502, 1994). In addition, this study also showed that the penetration of vinblastine into various tissues was enhanced in the mutant mice.

None of the published studies provided any regimen for implementing the effective oral administration of otherwise poorly bioavailable drugs, e.g., indicating the respective dosage ranges and timing of administration for specific target drugs and bioavailability-enhancing agents or demonstrating which MDR-inhibiting agents are best suited for promoting oral absorption of each target drug or class of drugs.

Methods disclosed in the art for increasing gut absorption of drugs that have until now only been administered parenterally generally focus on the use of permeation and solubility enhancers as promoting agents, or the co-administration by intraluminal perfusion in the small intestine or by the intravenous route of P-glycoprotein inhibitors, e.g., Leu et al., *Cancer Chemother. Pharmacol.*, 35: 432–436, 1995 (perfusion or IV infusion of quinidine suppresses efflux of etoposide into the lumen of the G.I. tract from the blood). But these methods suffer from numerous drawbacks. The solubility and permeability enhancing agents are often either impractical or ineffective for oral administration in the doses required and may interfere with the pharmacological activity of the target drug. Parenteral administration of P-glycoprotein inhibitors in therapeutic (or near-therapeutic) doses into humans can cause severe clinical consequences. In the case of quinidine, for example, IV administration may cause arrhythmias, peripheral vasodilation, gastrointestinal upset and the like.

In published PCT application Ser. No. WO 95/20980 (published Aug. 10, 1995) Benet et al. disclose a purported method for increasing the bioavailability of orally administered hydrophobic pharmaceutical compounds. This method comprises orally administering such compounds to the patient concurrently with a bioenhancer comprising an inhibitor of a cytochrome P450 3A enzyme or an inhibitor of P-glycoprotein-mediated membrane transport. Benet et al., however, provide virtually no means for identifying which bioavailability enhancing agents will improve the availability of specific "target" pharmaceutical compounds, nor do they indicate specific dosage amounts, schedules or regimens for administration of the enhancing or target agents. In fact, although the Benet application lists dozens of potential enhancers (P450 3A inhibitors) and target drugs (P450 3A substrates), the only combination of enhancer and target agent supported by any experimental evidence in the application is ketoconazole as the enhancer and cyclosporin A as the target drug.

When describing the general characteristics of compounds which can be used as bioenhancers by reduction of P-glycoprotein transport activity, Benet et al. indicate that these are hydrophobic compounds which generally, but not necessarily, comprise two co-planar aromatic rings, a positively charged nitrogen group or a carbonyl group—a class that includes an enormous number of compounds, most of which would not provide the desired absorption enhancing activity in the case of specific target agents. Moreover, the classes of target agents disclosed by Benet et al. include the great majority of pharmaceutical agents listed in the *Physicians' Desk Reference*. These inclusion criteria are of no value to medical practitioners seeking safe, practical and effective methods of orally administering specific pharmaceutical agents.

A further deficiency with Benet et al.'s disclosure is the standard applied for determining as to whether bioavailability of a drug that is poorly absorbed upon oral administration has been improved. Benet et al. indicate that any P-glycoprotein inhibiting agent which, when present in the gut at a given concentration, reduces transmembranal transport of Rhodamine 123 by P-glycoprotein in brush border membrane vesicles or P-glycoprotein containing cells by 10% or more may be considered a bioenhancing agent at that concentration and can be used in the practice of their invention. But an increase of only 10% in absorption from the gut of an otherwise not absorable agent is inadequate to render the agent therapeutically valuable for any purpose. Indeed, under guidlines of the Federal Food and Drug Administration, two pharmaceutical formulations containing the same active ingredient, but differing in their bioavailability levels by −20%/+25%, are still considered bioequivalent because for most drugs a −20%/+25% difference in concentration of the active ingredient in the blood is not clinically significant. *Approved Drug Products with Therapeutic Equivalence Evaluations* (Dept. of HHS, 14th ed. 1994). When the FDA rules that two pharmaceutical formulations are bioequivalent, physicians and pharmacists consider them freely substitutable for one another.

In general, Benet et al. provides no teaching that could be followed by persons skilled in the medical and pharmaceutical arts to identify suitable bioenhancer/target drug combinations or to design specific treatment regimens and schedules which would render the target agents therapeutically effective upon oral administration.

Thus, a safe yet effective method for increasing the systemic availability upon oral administration of drugs that are currently administered only parenterally because they are not absorbed sufficiently or consistently when administered by the oral route is required and has not been provided in the prior art.

SUMMARY OF THE INVENTION

Surprisingly, it has now been discovered and experimentally verified that certain agents which apparently inhibit P-glycoprotein drug transport activity, particularly cyclosporins, can be used to increase substantially the oral bioavailability of otherwise poorly available or non-available pharmaceutical agents, e.g., the anti-cancer drugs paclitaxel (formerly known as taxol), as well as its analogs and derivatives, and etoposide.

The present invention relates in one aspect to a method of increasing the oral bioavailability of pharmaceutical agents that are poorly absorbed or not absorbed at all from the gastrointestinal tract or gut by pre-administering and/or simultaneously all from the gastrointestinal tract or gut by pre-administering and/or simultaneously administering to a subject by the oral route one or a combination of agents known to be effective in inhibiting the P-glycoprotein drug transport pump. If pre-administration is used, the bioavailability enhancing agent or agents must be administered in sufficient quantities and within a short enough time period before administration of the drug whose bioavailability is to be increased (the "target drug" or "target agent") so that a sufficient level of the enhancing agent remains at the site of absorption at the time of administration of the target agent to effectively inhibit the activity of the P-glycoprotein or other multi-drug transporter substances.

In a second aspect, the invention pertains to compositions or dosage forms for oral administration of pharmaceutical agents that were heretofore available for parenteral administration only. A third aspect of the invention relates to the administration of such oral dosage forms or a combination thereof to patients for treatment of diseases responsive to the active agents contained therein.

The invention also pertains to pharmaceutical kits comprising one or more oral dosage forms containing a target agent and one or more oral dosage forms containing an enhancing agent.

BRIEF DESCRIPTION OF THE DRAWINGS

FIG. 7A is a graph reflecting the levels of total radioactivity and unchanged paclitaxel detected in whole blood samples taken from a group of 10 rats over a period of 24 hours, said group having been administered radiolabeled paclitaxel (9 mg/kg) orally with oral cyclosporine doses (5 mg/kg) prior to and immediately after the paclitaxel dose.

Figure 12:
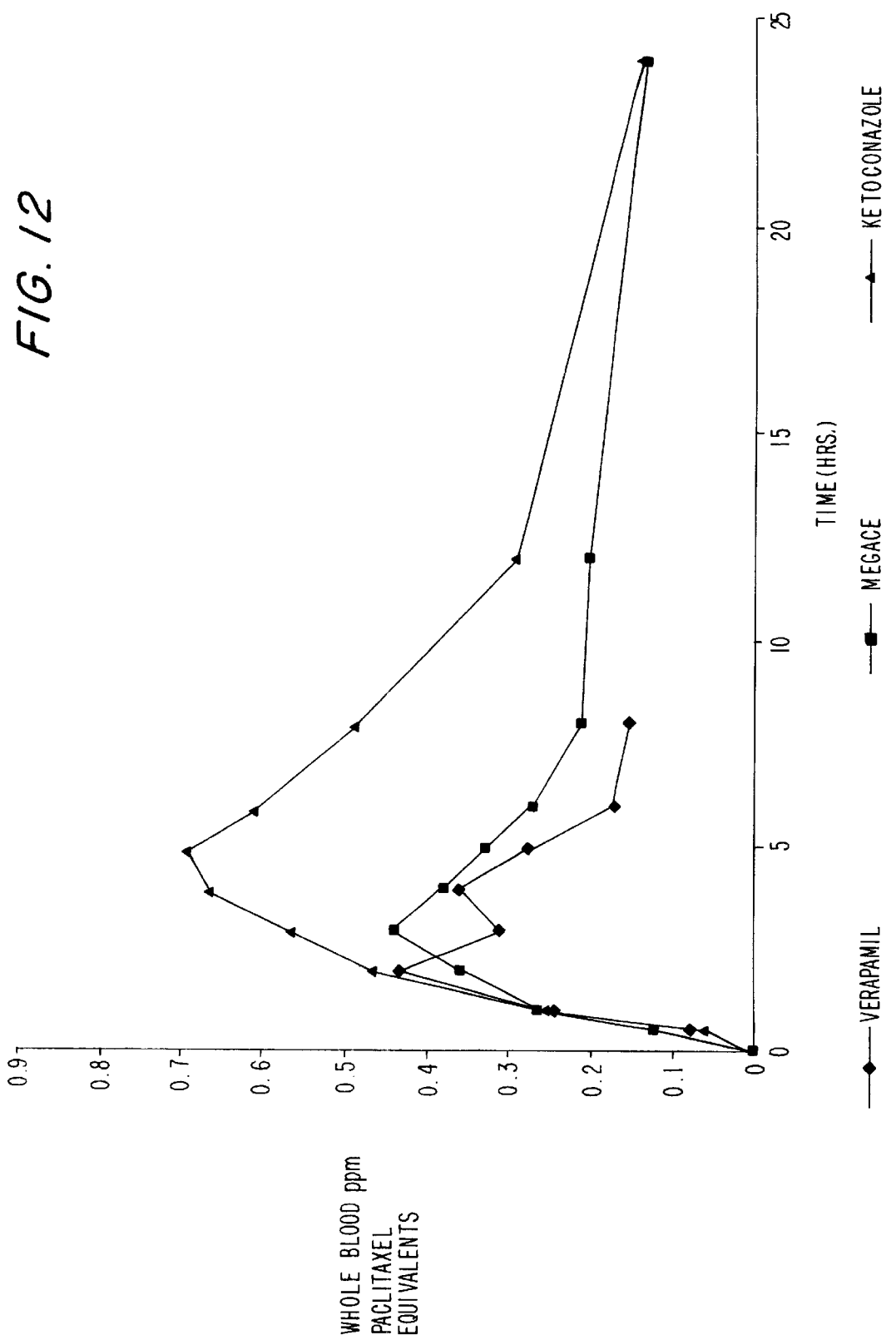
FIG. 12 is a graph reflecting the levels of radioactivity detected in whole blood samples taken from three groups of rats over a period of 24 hours: one group administered 100 mg/kg of verapamil orally[1] as an enhancing agent, a second administered megestrol acetate (marketed as MEGACE® by Bristol-Myers Squibb Oncology) orally as an enhancing agent and a third administered ketoconazole orally as an enhancing agent, with each group being administered the same oral dose of the same enhancing agent one hour later immediately after an oral dose of radiolabeled paclitaxel.

[1] As reflected on FIG. 12 the rats in the group receiving high dose verapamil did not survive beyond about 8 hours.

Figure 13:
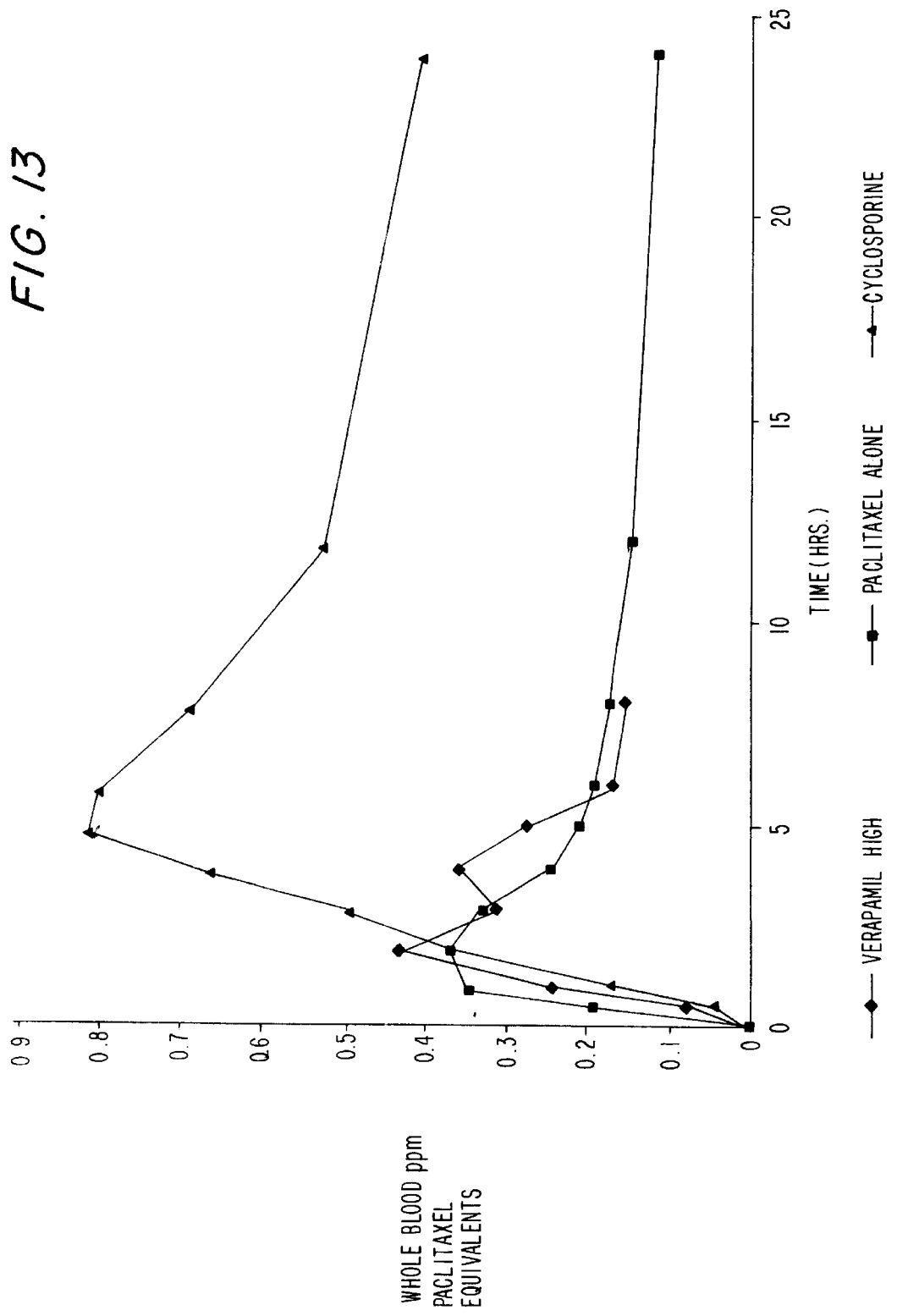

FIG. 13 is a graph reflecting the levels of radioactivity detected in whole blood samples taken over a period of 24 hours from the rats of the first group defined with respect to FIG. 12 (administered 100 mg/kg verapamil orally), a group of rats administered radiolabeled oral paclitaxel alone and a group of rats administered cyclosporine orally one hour prior to and again immediately after radiolabeled oral paclitaxel.

Figure 14:
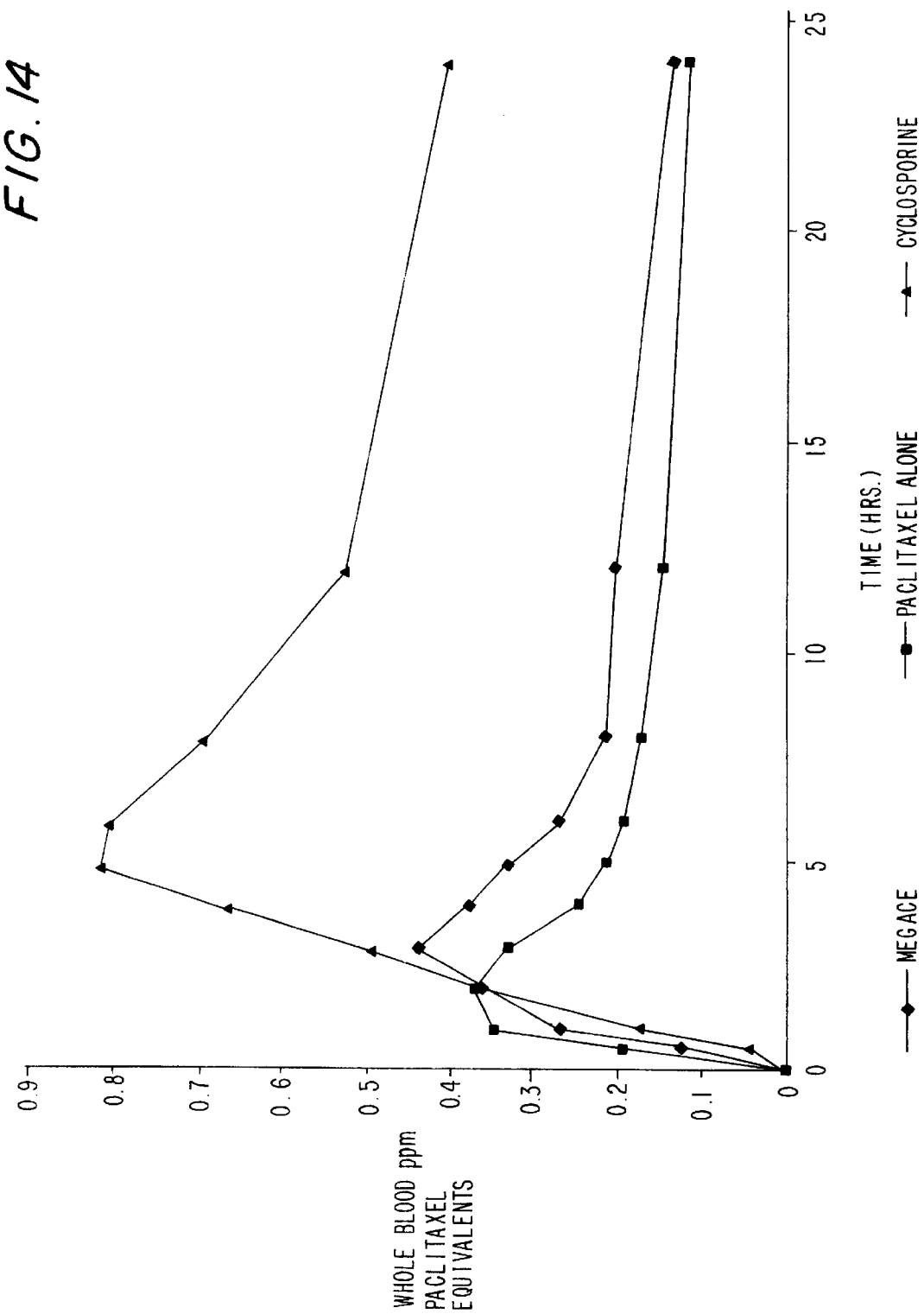

FIG. 14 is a graph reflecting the levels of radioactivity detected in whole blood samples taken over a period of 24 hours from the rats of the second group defined with respect to FIG. 12 (administered megestrol acetate orally), a group of rats administered radiolabeled oral paclitaxel alone and a group of rats administered cyclosporine orally one hour prior to and again immediately after radiolabeled oral paclitaxel.

Figure 15:
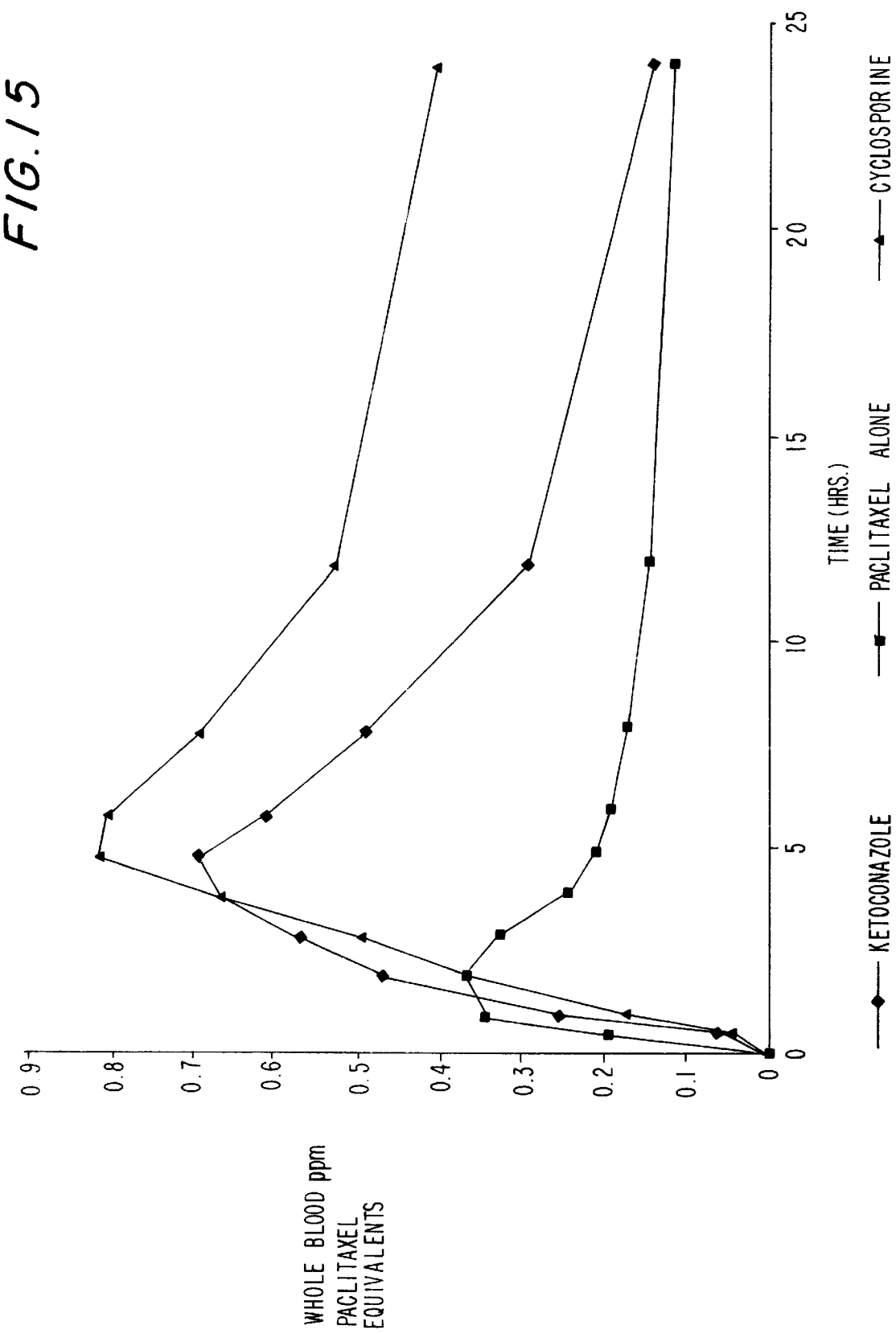

FIG. 15 is a graph reflecting the levels of radioactivity detected in whole blood samples taken over a period of 24 hours from the rats of the third group defined with respect to FIG. 12 (administered ketoconazole orally), a group of rats administered radiolabeled oral paclitaxel alone and a group of rats receiving cyclosporine orally one hour prior to and again immediately after radiolabeled oral paclitaxel.

Figure 8:
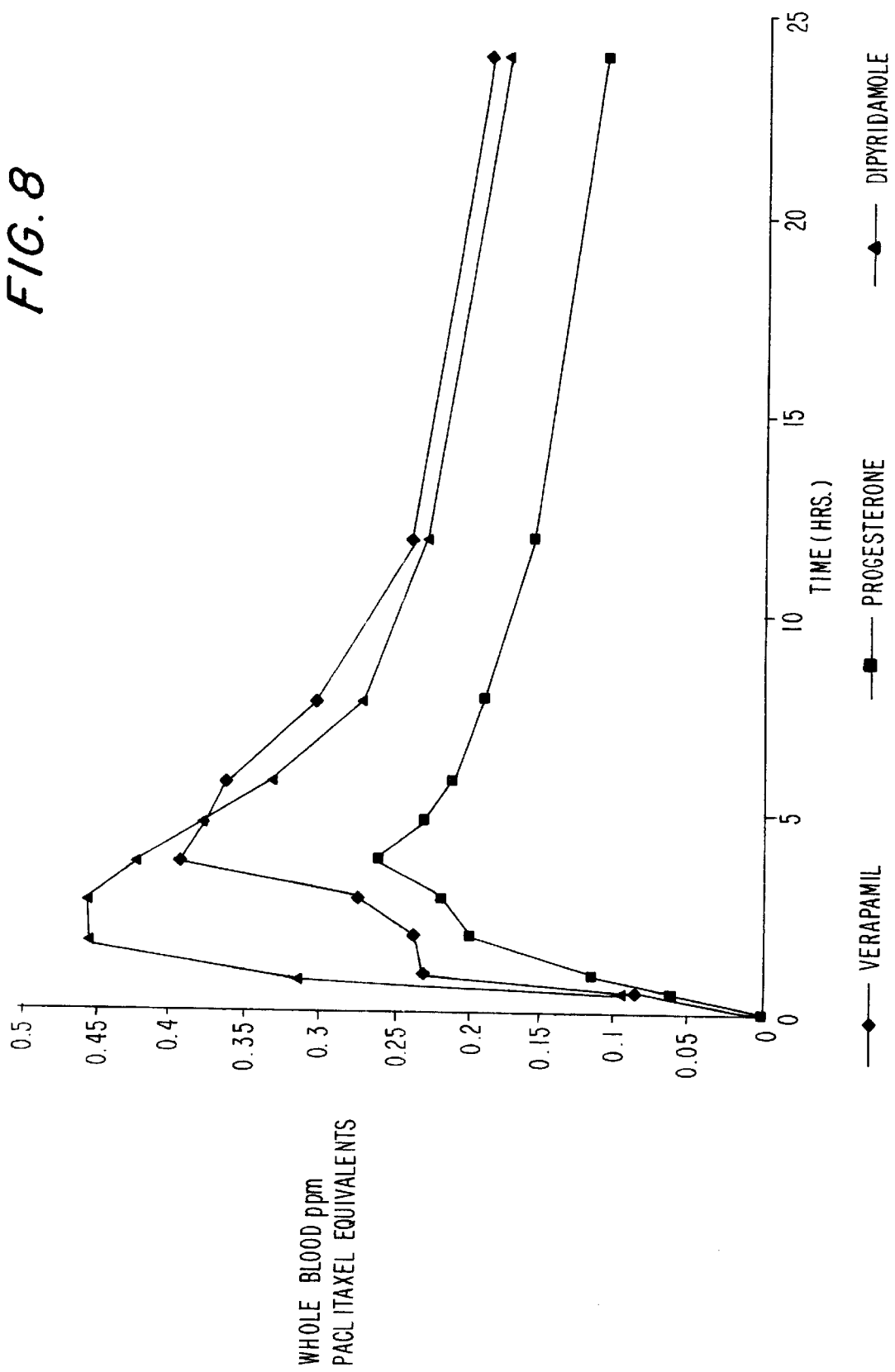
FIG. 8 is a graph reflecting the levels of radioactivity detected in whole blood samples taken from three groups of rats over a period of 24 hours: one group administered 10 mg/kg of verapamil orally as an enhancing agent, a second administered progesterone orally as an enhancing agent and a third administered dipyridamole orally as an enhancing agent, with each group being administered an oral dose of the same enhancing agent one hour later immediately after an oral dose of radiolabeled paclitaxel.
Figure 16:
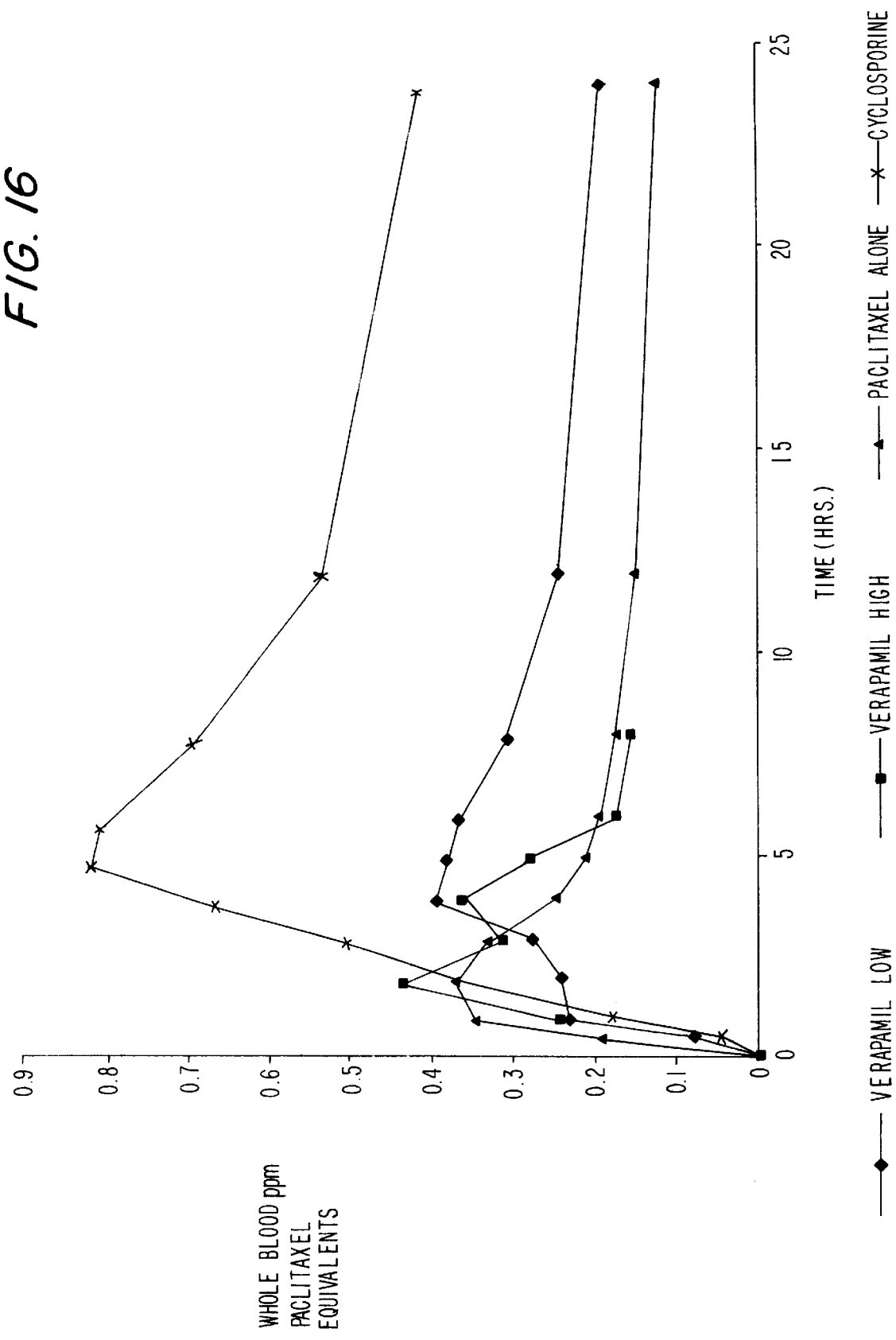

FIG. 16 is a graph reflecting the levels of radioactivity detected in whole blood samples taken over a period of 24 hours from the rats of the first group defined with respect to FIG. 8 (administered 10 mg/kg of verapamil), the first group defined with respect to FIG. 12 (administered 100 mg/kg of verapamil), a group of rats receiving radiolabeled oral paclitaxel alone and a group of rats receiving cyclosporine orally one hour prior to and again immediately after radiolabeled oral paclitaxel.

Figure 17:
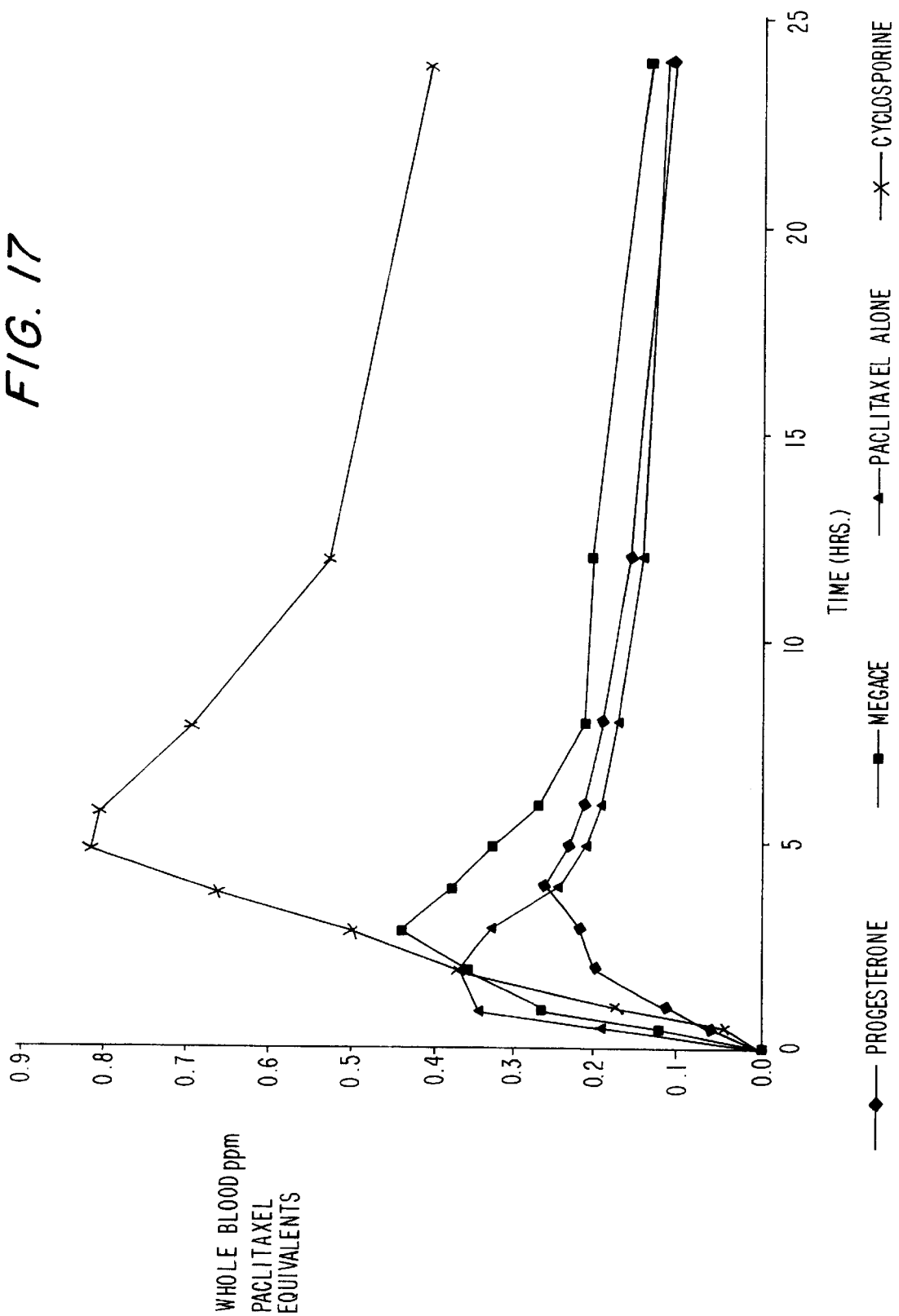

FIG. 17 is a graph reflecting the levels of radioactivity detected in whole blood samples taken over a period of 24 hours from the rats of the second group defined with respect to FIG. 8 (administered progesterone orally), the second group defined with respect to FIG. 12 (administered megestrol acetate orally), a group of rats receiving radiolabeled oral paclitaxel alone and a group of rats receiving cyclosporine orally one hour prior to and again immediately after radiolabeled oral paclitaxel.

FIG. 17A is a graph reflecting a comparison of dose response curves in a group of rats receiving cyclosporine orally one hour prior to and again immediately after radiolabeled oral paclitaxel with a group of rats receiving ketoconazole orally one hour prior to and again immediately after radiolabeled oral paclitaxel. FIG. 17B is a comparison of $AUC_{0-24}$ values determined with respect to the same two groups of rats.

Figure 18:
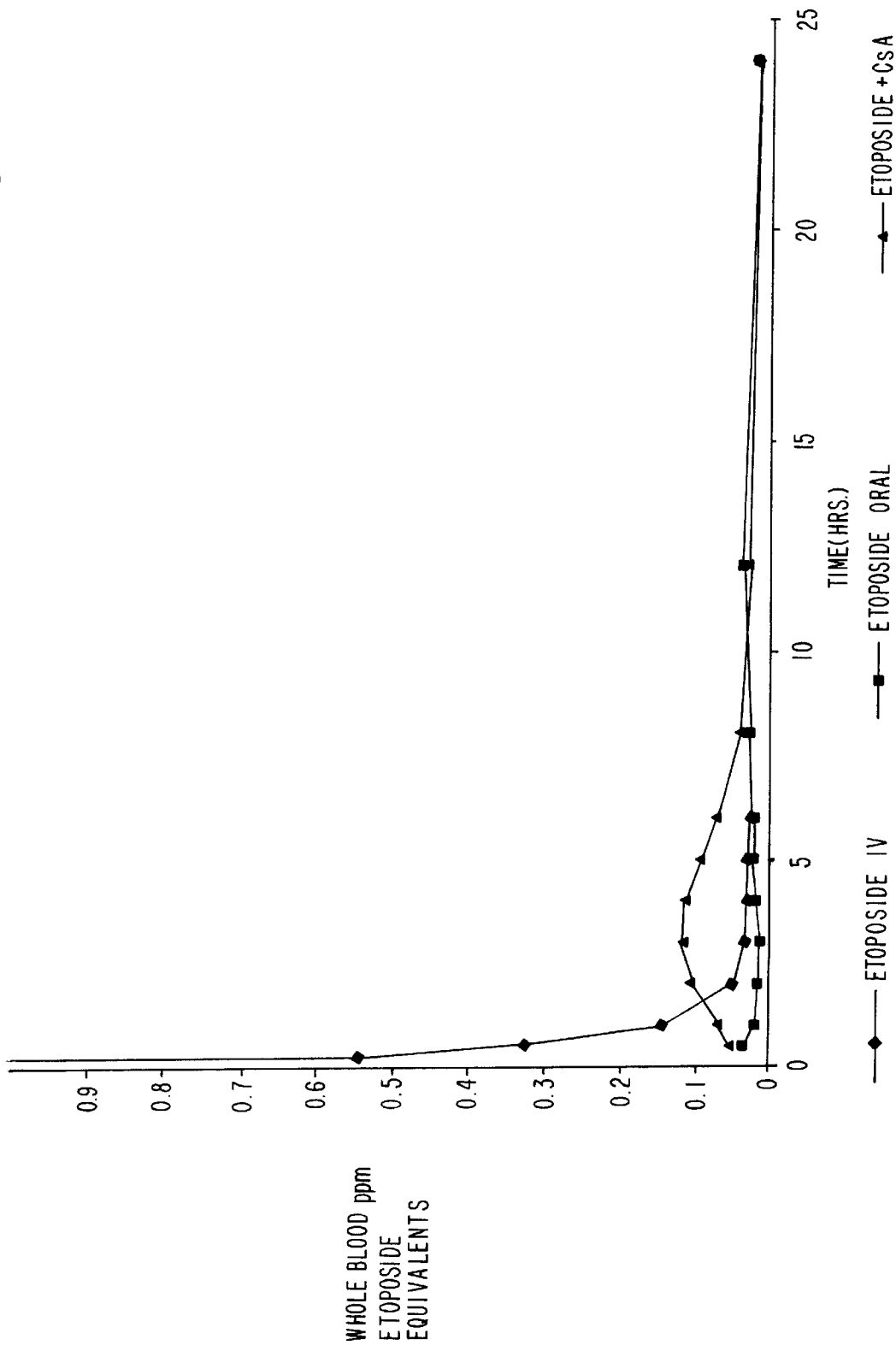

FIG. 18 is a graph reflecting the levels of radioactivity detected in whole blood samples taken from three groups of rats over a period of 24 hours: one group administered only radiolabeled etoposide IV, a second administered only radiolabeled etoposide orally and a third administered radiolabeled etoposide orally with oral cyclosporine doses prior to and immediately after the etoposide dose, with the ordinate scale running from 0 to 1 whole blood ppm etoposide equivalents.

Figure 19:
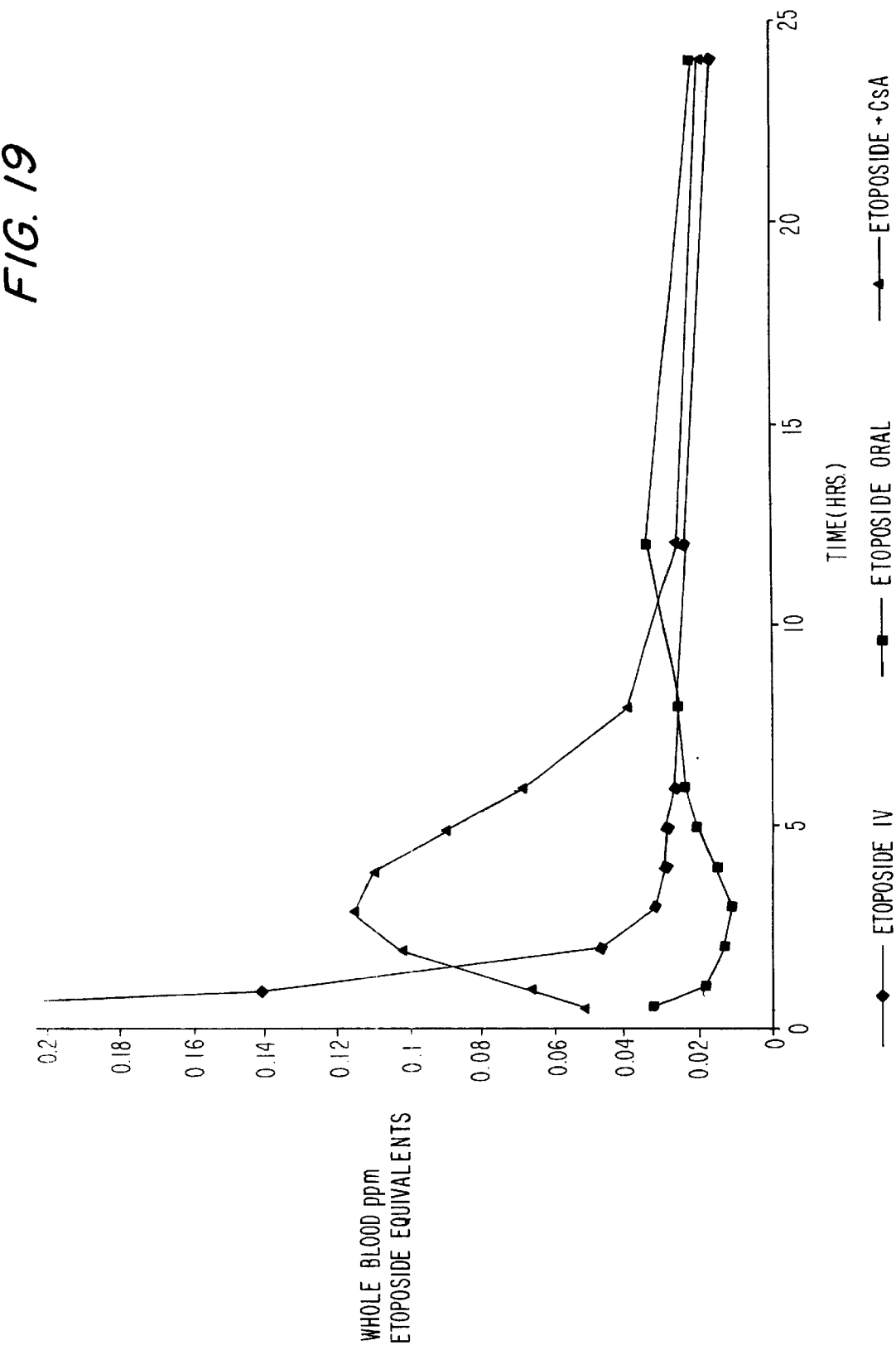

FIG. 19 is a graph reflecting the levels of radioactivity detected in whole blood samples taken from the three groups of rats defined with respect to FIG. 18, with the ordinate scale running from 0 to 0.2 whole blood ppm radiolabeled etoposide equivalents.

Figure 20:
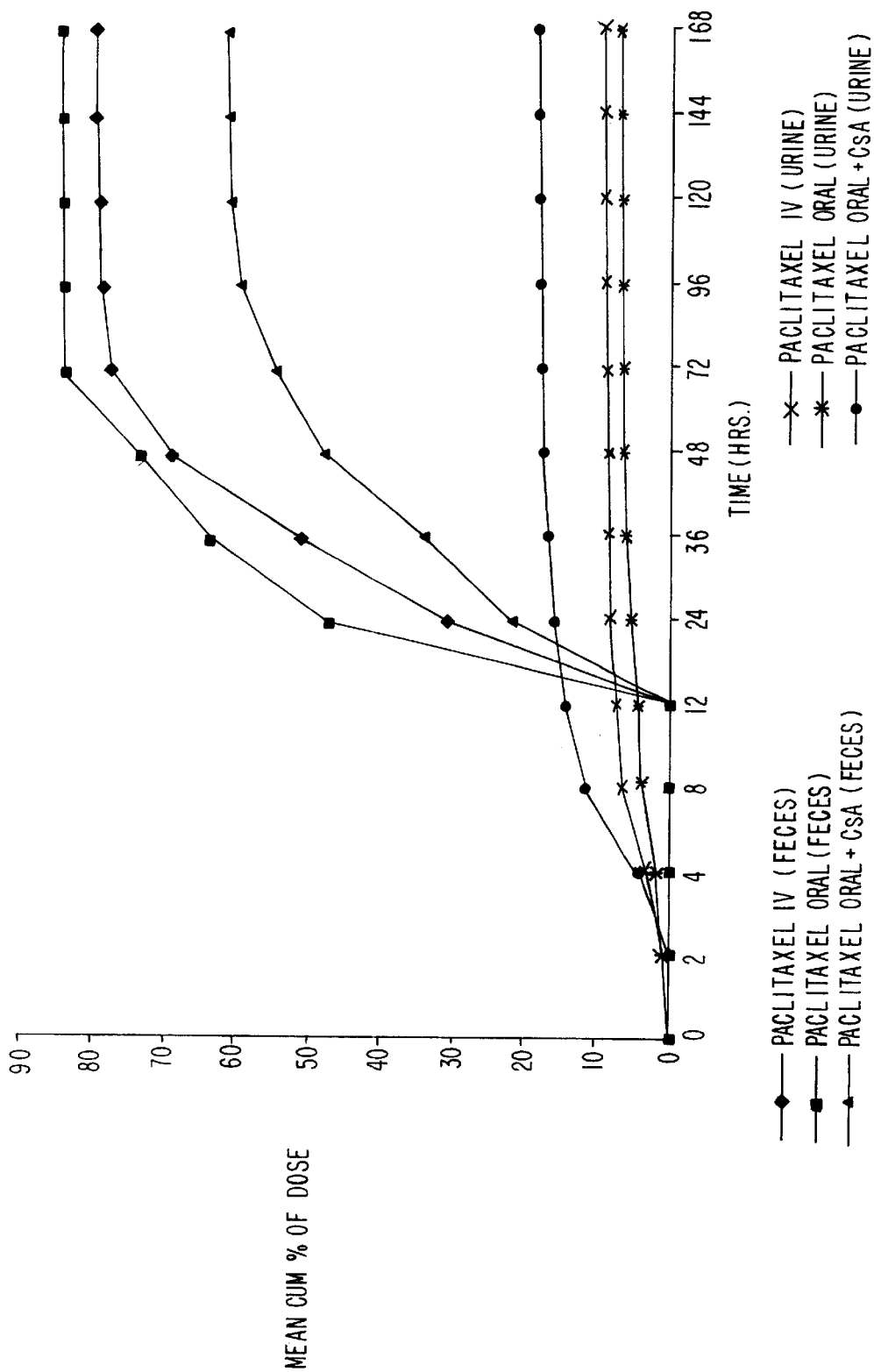

FIG. 20 is a graph reflecting the mean cumulative % of dose of radioactivity detected in the feces and urine of three groups of rats over a period of 168 hours: one group administered only radiolabeled paclitaxel IV, a second administered only radiolabeled paclitaxel orally and a third administered radiolabeled paclitaxel orally with oral cyclosporine doses prior to and immediately after the paclitaxel dose.

Figure 21:
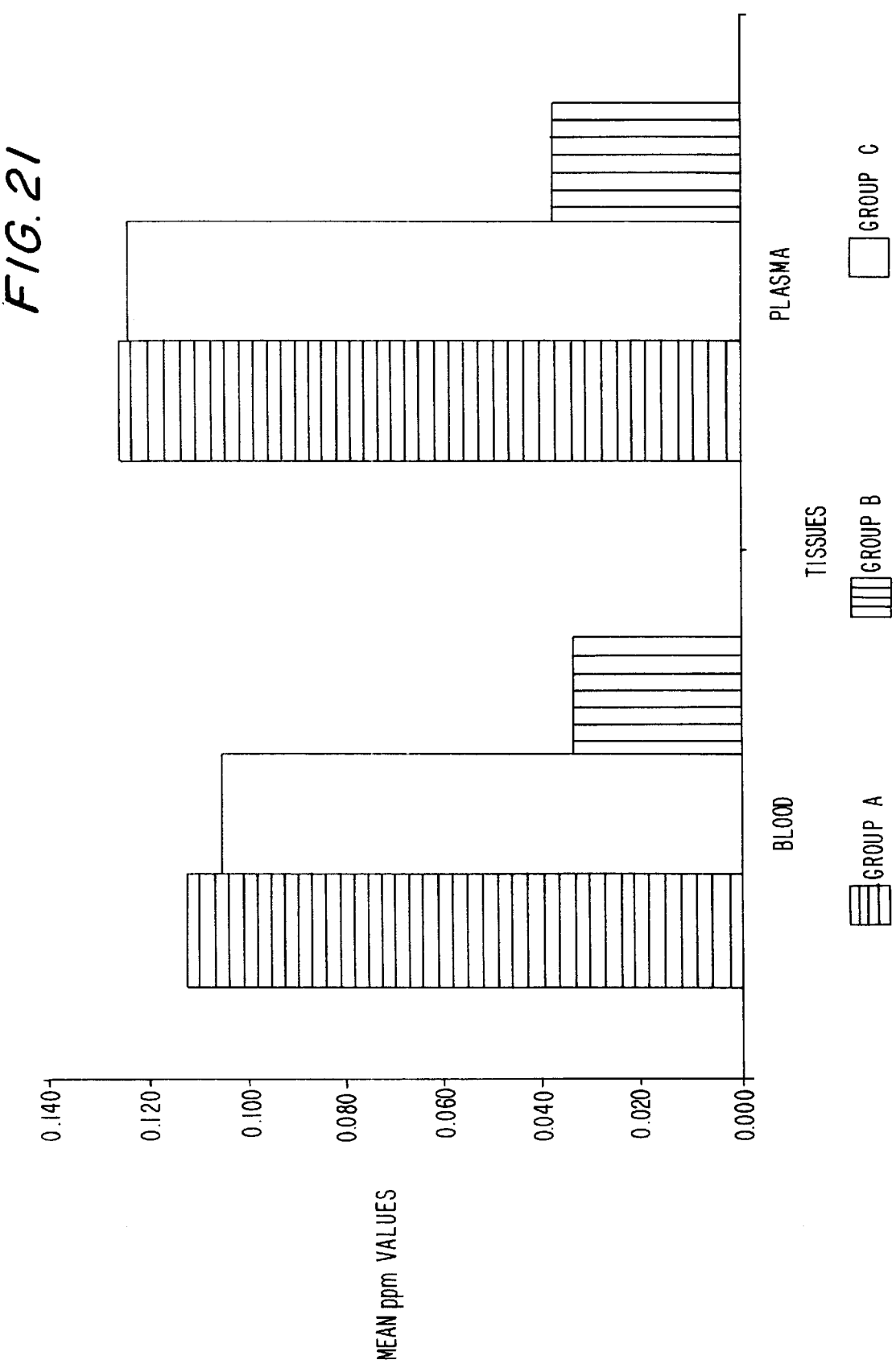

FIG. 21 is a bar graph reflecting the mean ppm values of paclitaxel equivalents detected in blood and plasma from the three groups of rats defined with respect to FIG. 20 168 hours (7 days) after administration of paclitaxel.

Figure 22:
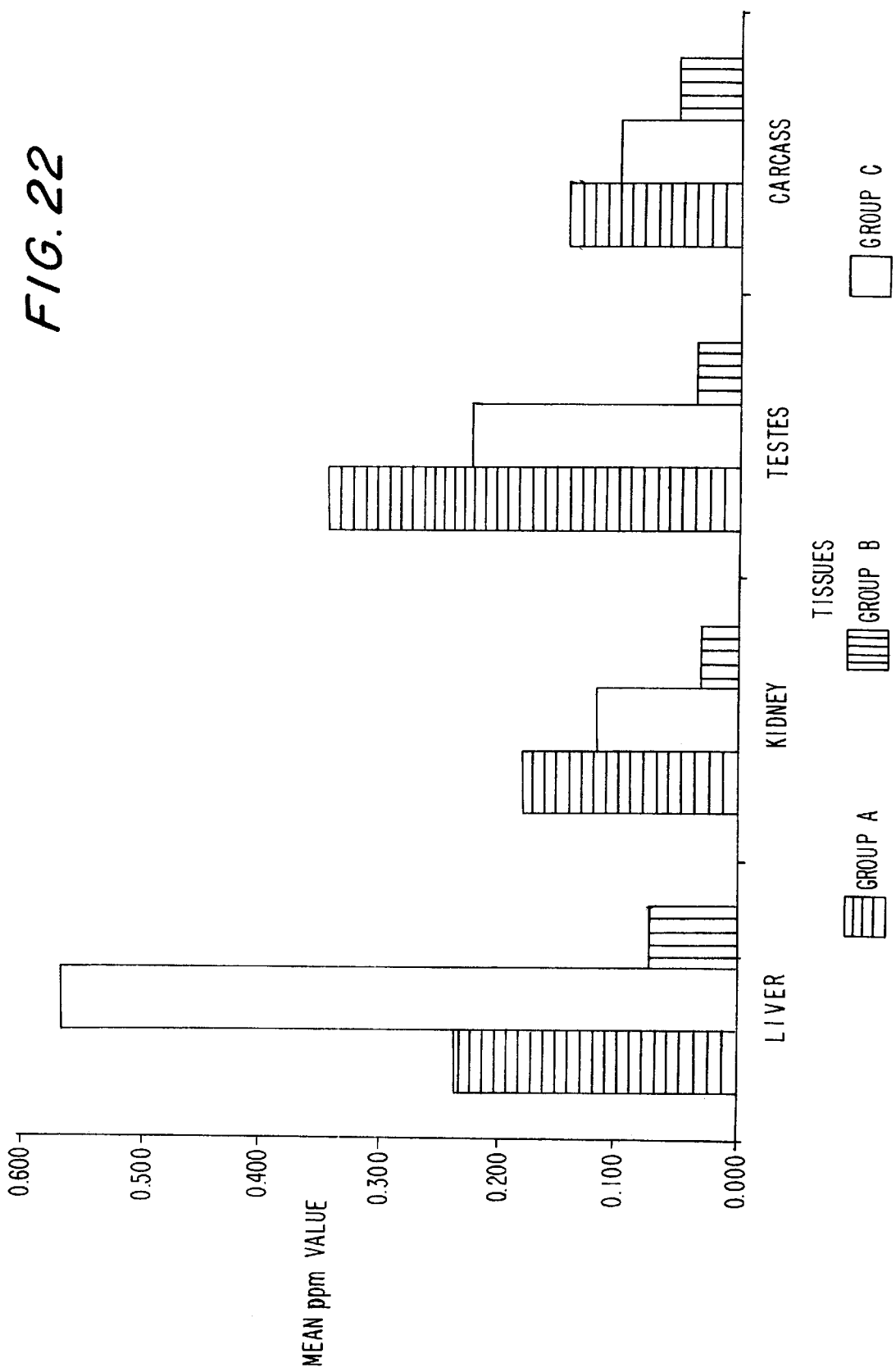

FIG. 22 is a bar graph reflecting the mean ppm values of paclitaxel equivalents detected in various tissues (liver, kidney, testes and carcass) from the three groups of rats defined with respect to FIG. 20 168 hours (7 days) after administration of paclitaxel.

Figure 23:
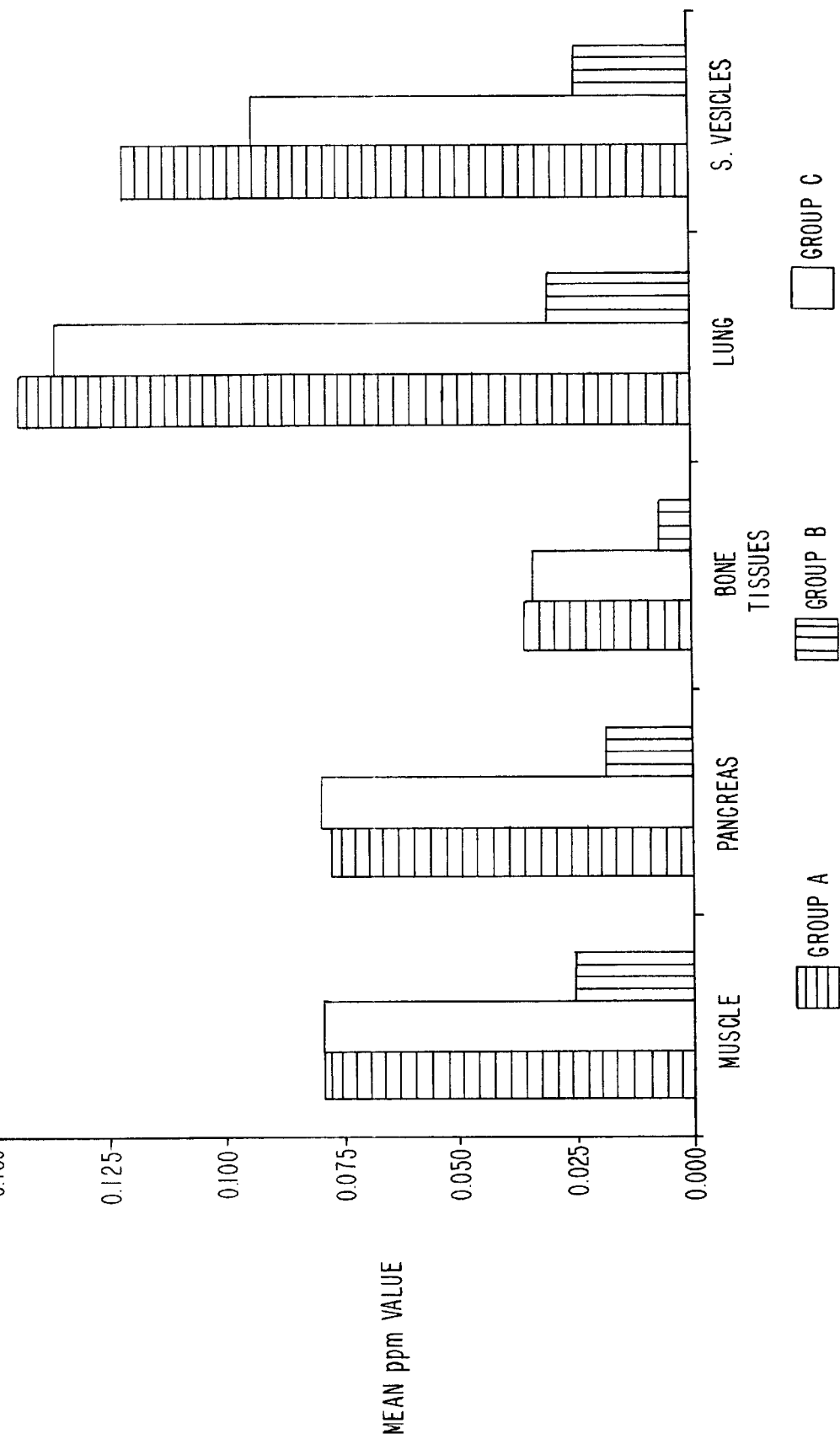

FIG. 23 is a bar graph reflecting the mean ppm values of paclitaxel equivalents detected in various tissues (muscle, pancreas, bone, lung and seminal vesicles) from the three groups of rats defined with respect to FIG. 20 168 hours (7 days) after administration of paclitaxel.

Figure 24:
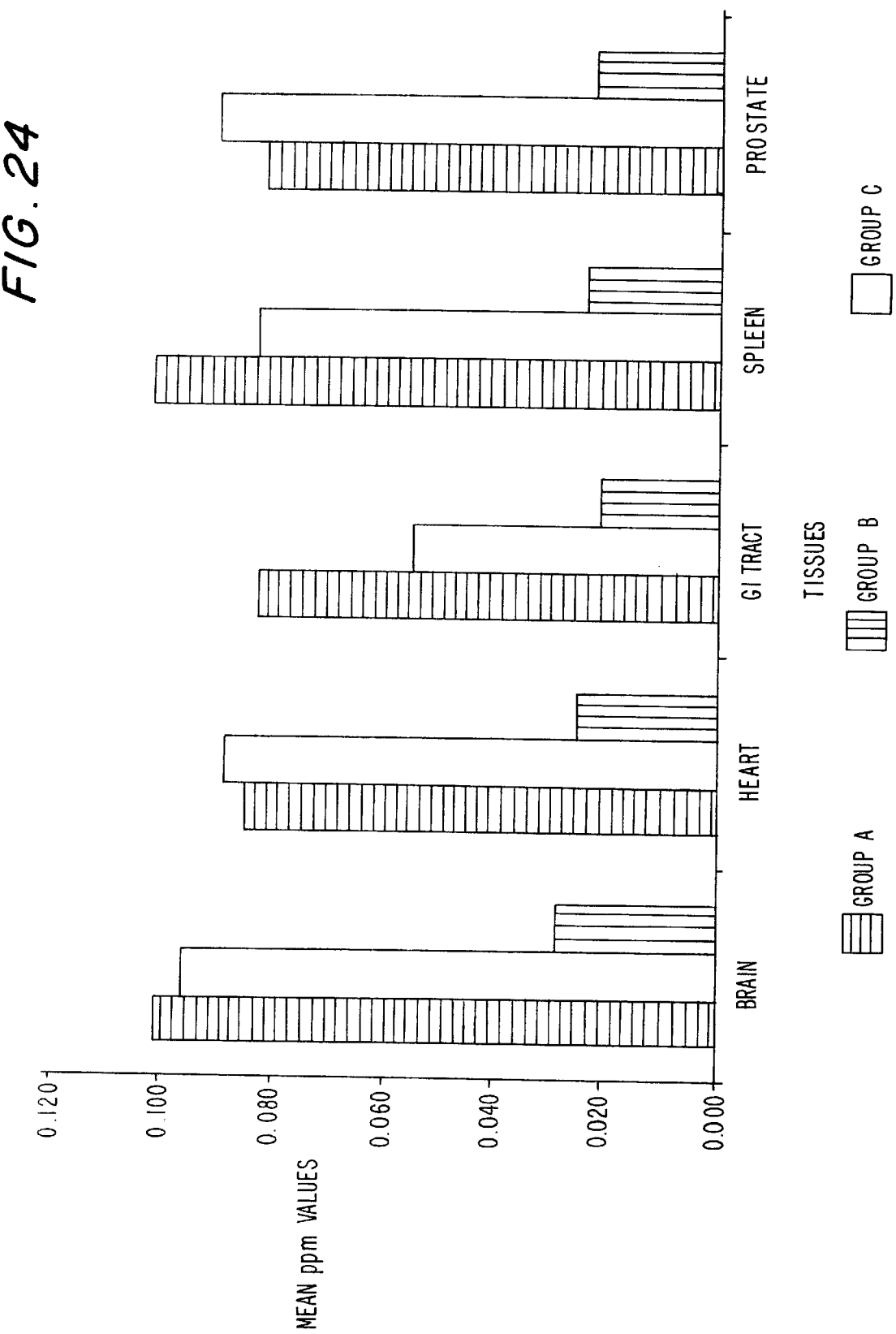

FIG. 24 is a bar graph reflecting the mean ppm values of paclitaxel equivalents detected in various tissues (brain, heart, G.I. tract, spleen and prostate) from the three groups of rats defined with respect to FIG. 20 168 hours (7 days) after administration of paclitaxel.

Figure 25:
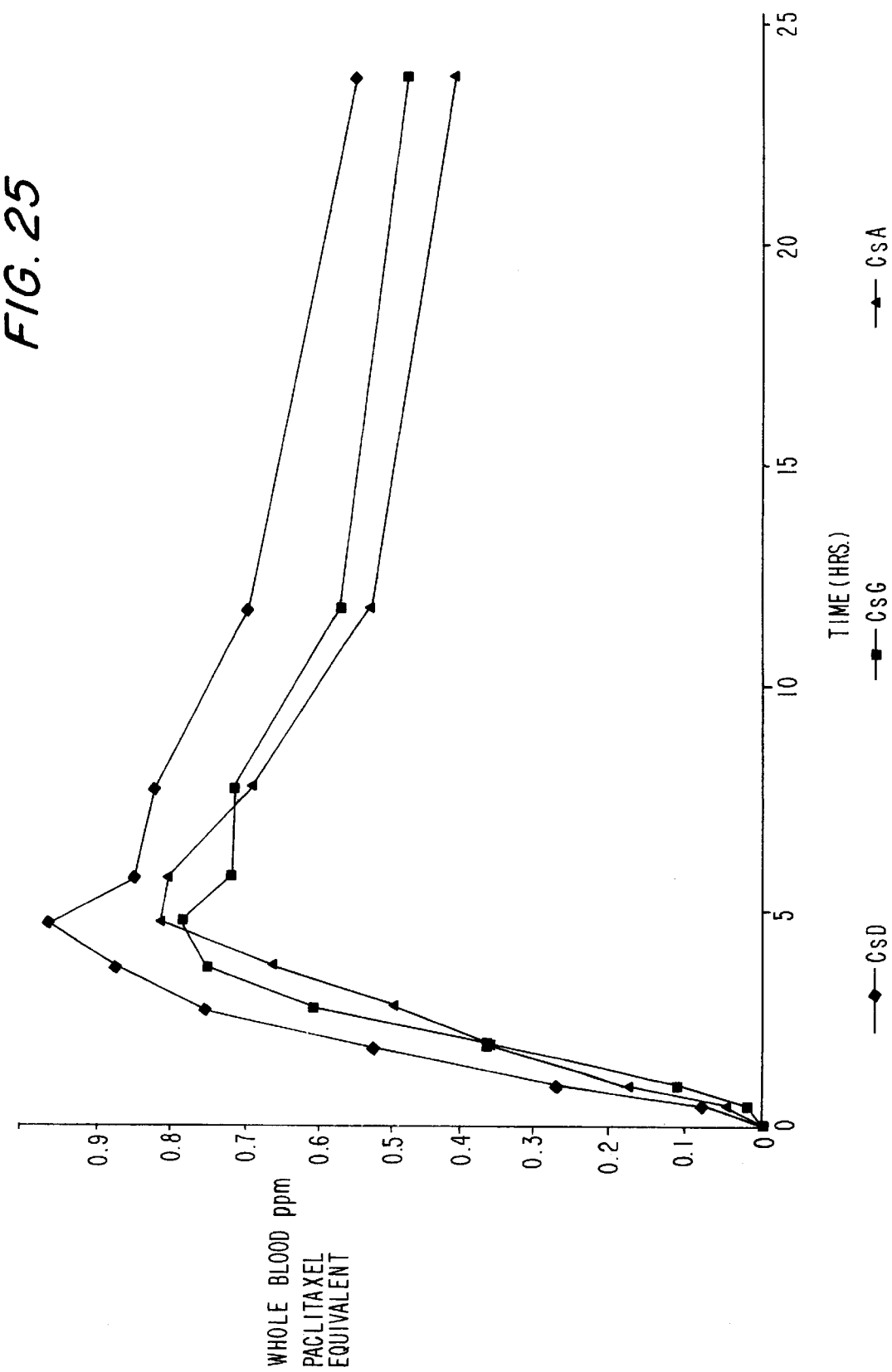

FIG. 25 is a graph reflecting the levels of radioactivity detected in whole blood samples taken from three groups of rats over a period of 24 hours: one group administered cyclosporin D orally both one hour before and immediately after an oral dose of radiolabeled paclitaxel, a second group administered cyclosporin G orally both one hour before and immediately after an oral dose of radiolabeled paclitaxel, and a third group administered cyclosporin A both one hour before and immediately after an oral dose of radiolabeled paclitaxel.

Figure 26:
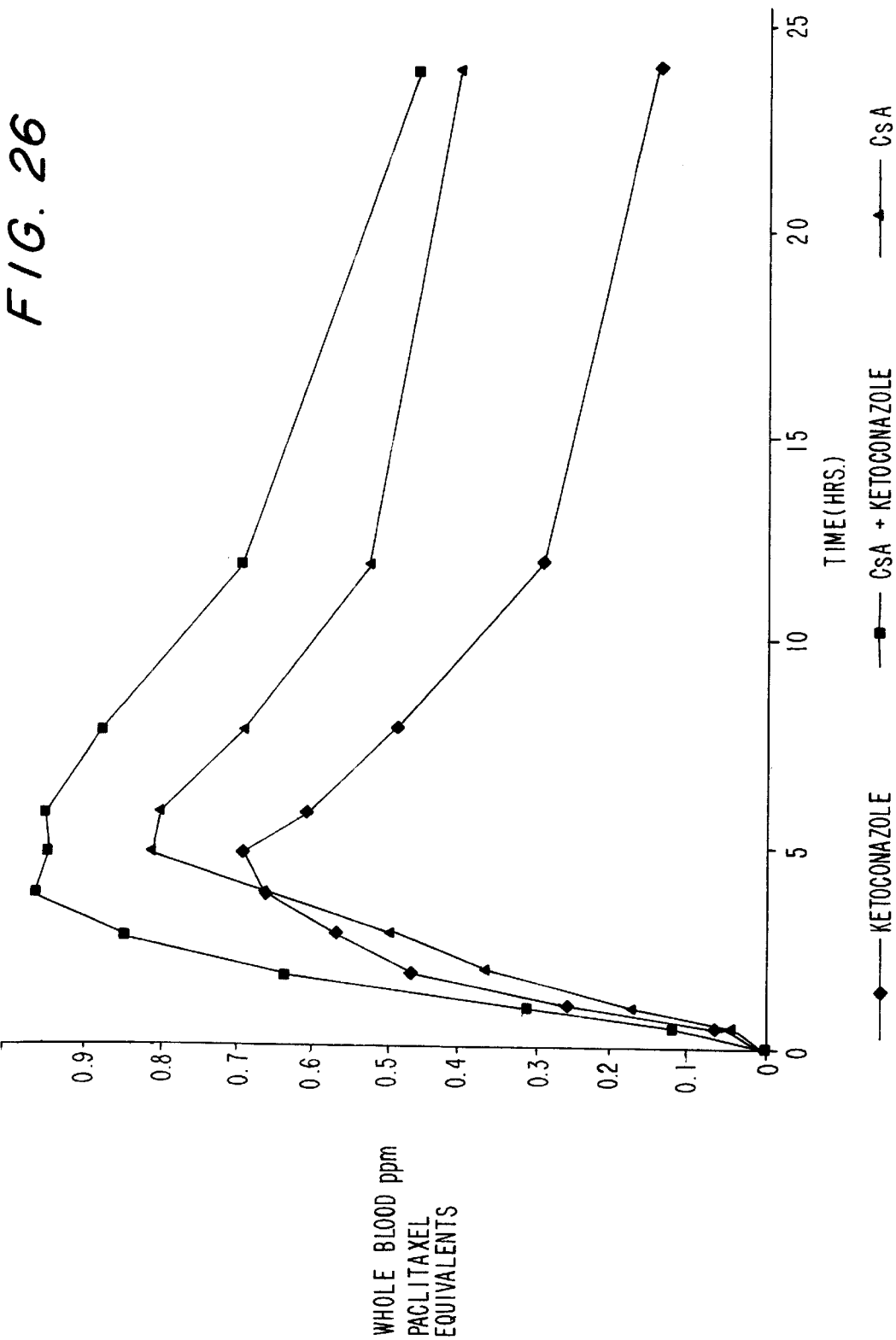

FIG. 26 is a graph reflecting the levels of radioactivity detected in whole blood samples taken from three groups of rats over a period of 24 hours: one group administered ketoconazole orally both one hour before and immediately after an oral dose of radiolabeled paclitaxel, a second group administered a combined oral dose of cyclosporin A and ketoconazole both one hour before and immediately after an oral dose of radiolabeled paclitaxel, and a third group administered cyclosporin A both one hour before and immediately after an oral dose of radiolabeled paclitaxel.

Figure 27:
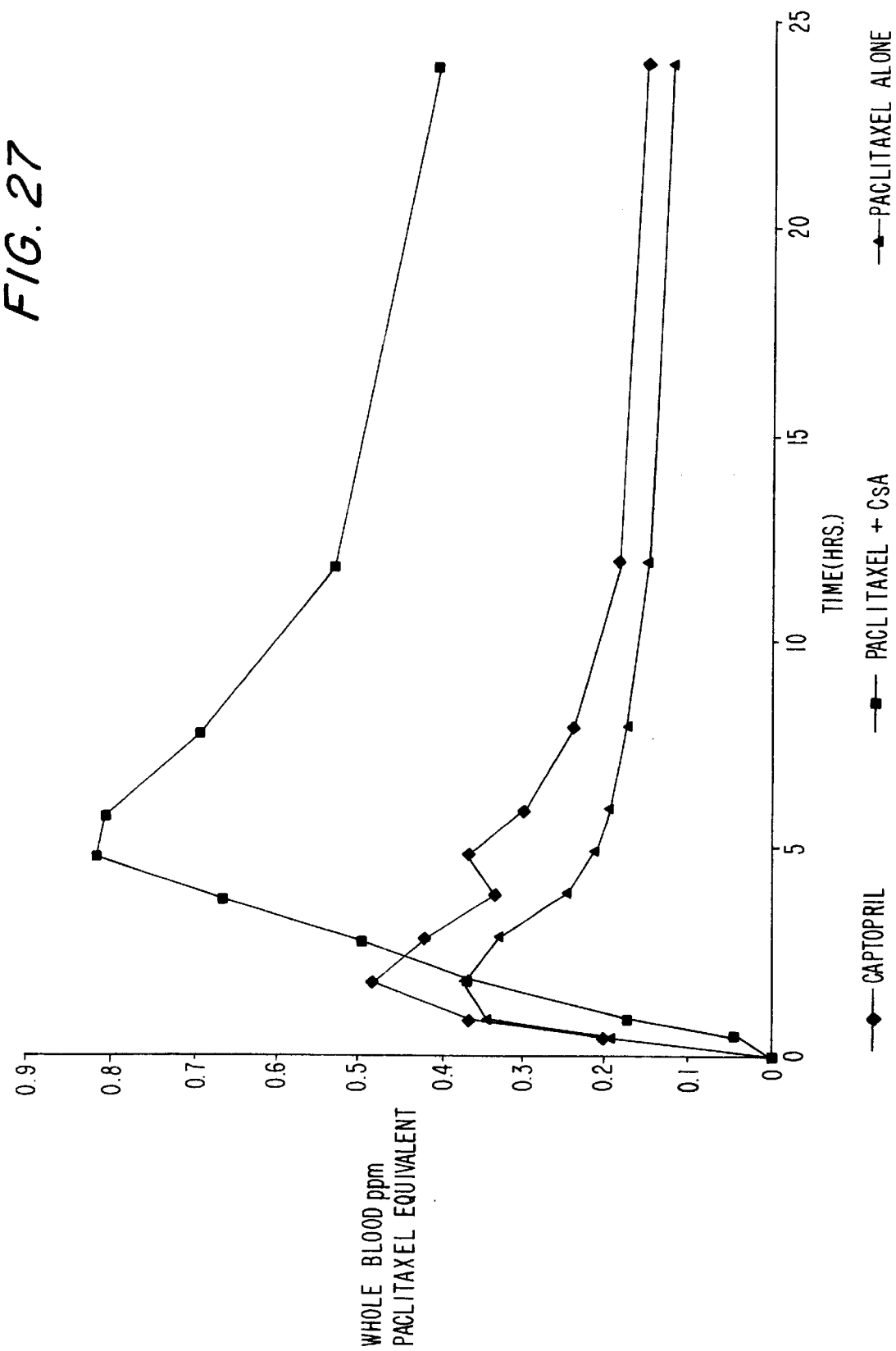

FIG. 27 is a graph reflecting the levels of radioactivity detected in whole blood samples taken from three groups of rats over a period of 24 hours: one group administered captopril orally both two hours before and immediately after an oral dose of radiolabeled paclitaxel, a second group administered cyclosporin A both one hour before and immediately after an oral dose of radiolabeled paclitaxel and a third group administered orally radiolabeled paclitaxel alone.

Figure 5:
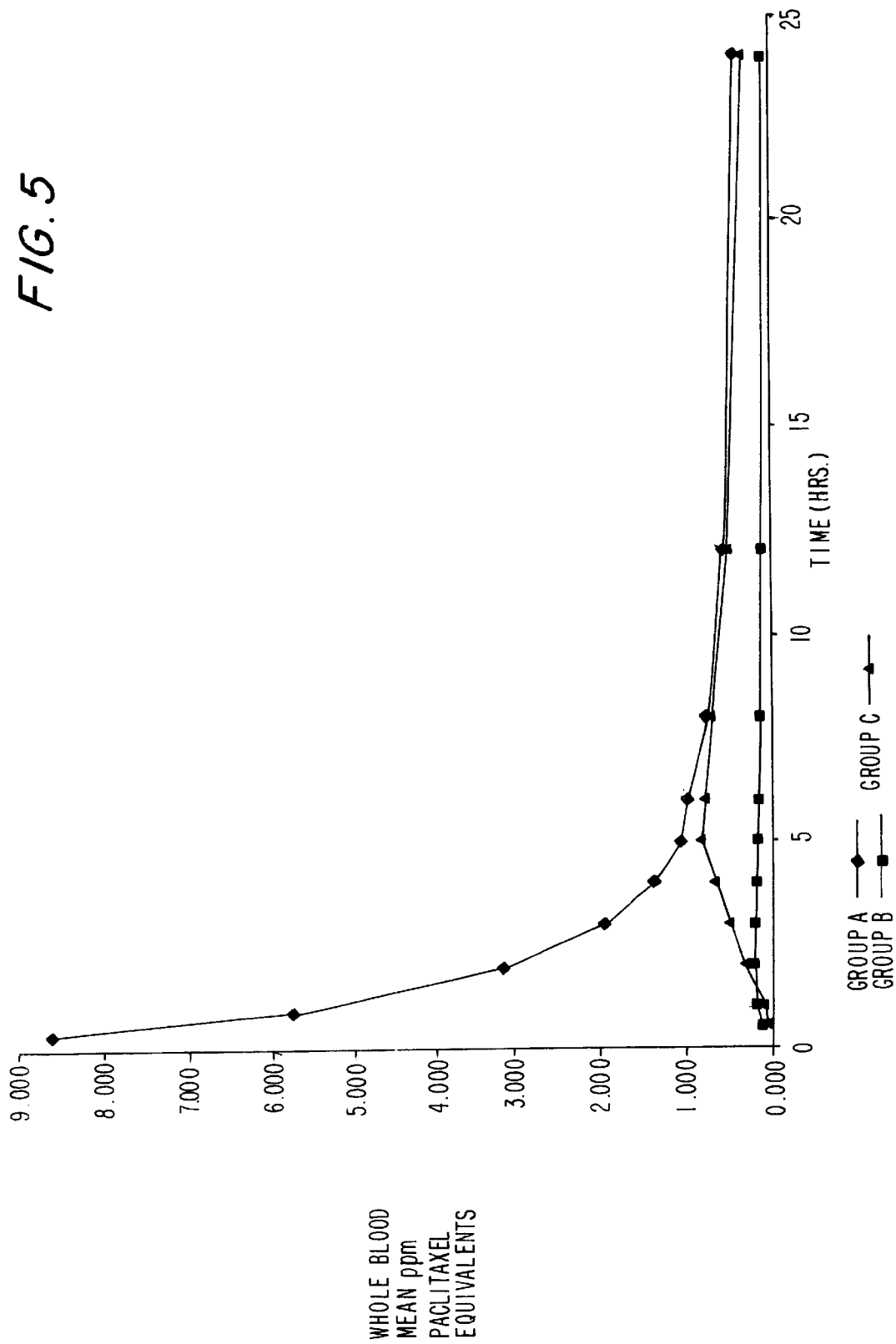
FIG. 5 is a graph reflecting the levels of radioactivity detected in whole blood samples taken from three groups of rats over a period of 24 hours: one (Group A) administered only radiolabeled paclitaxel IV, a second (Group B) administered only radiolabeled paclitaxel orally and a third group (Group C) administered radiolabeled paclitaxel orally with oral cyclosporine doses prior to and immediately after the paclitaxel dose.
Figure 28:
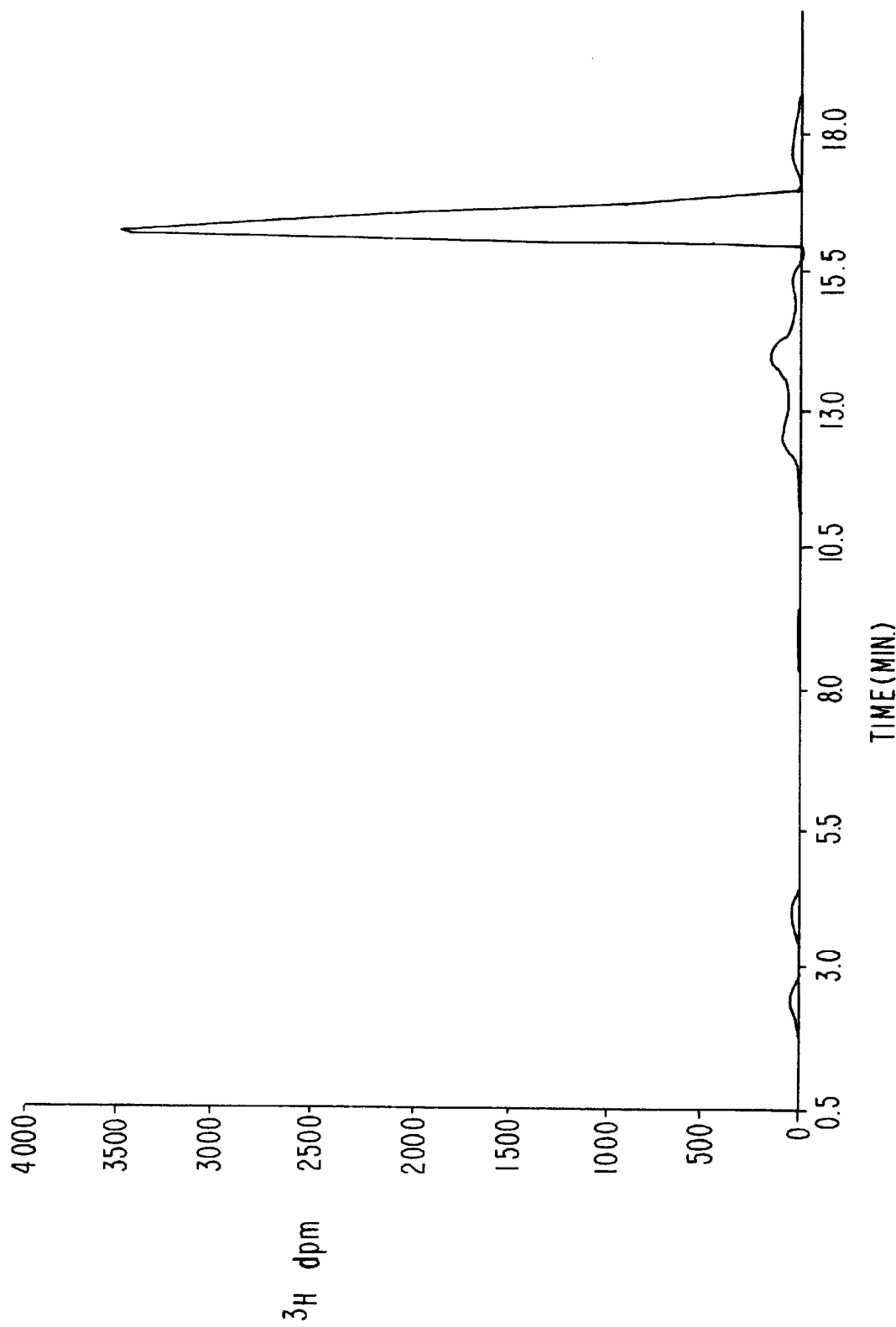

FIG. 28 shows the radioactivity profile from an HPLC-plasma extract from the rats in Group C defined with respect to FIG. 5.

Figure 29:
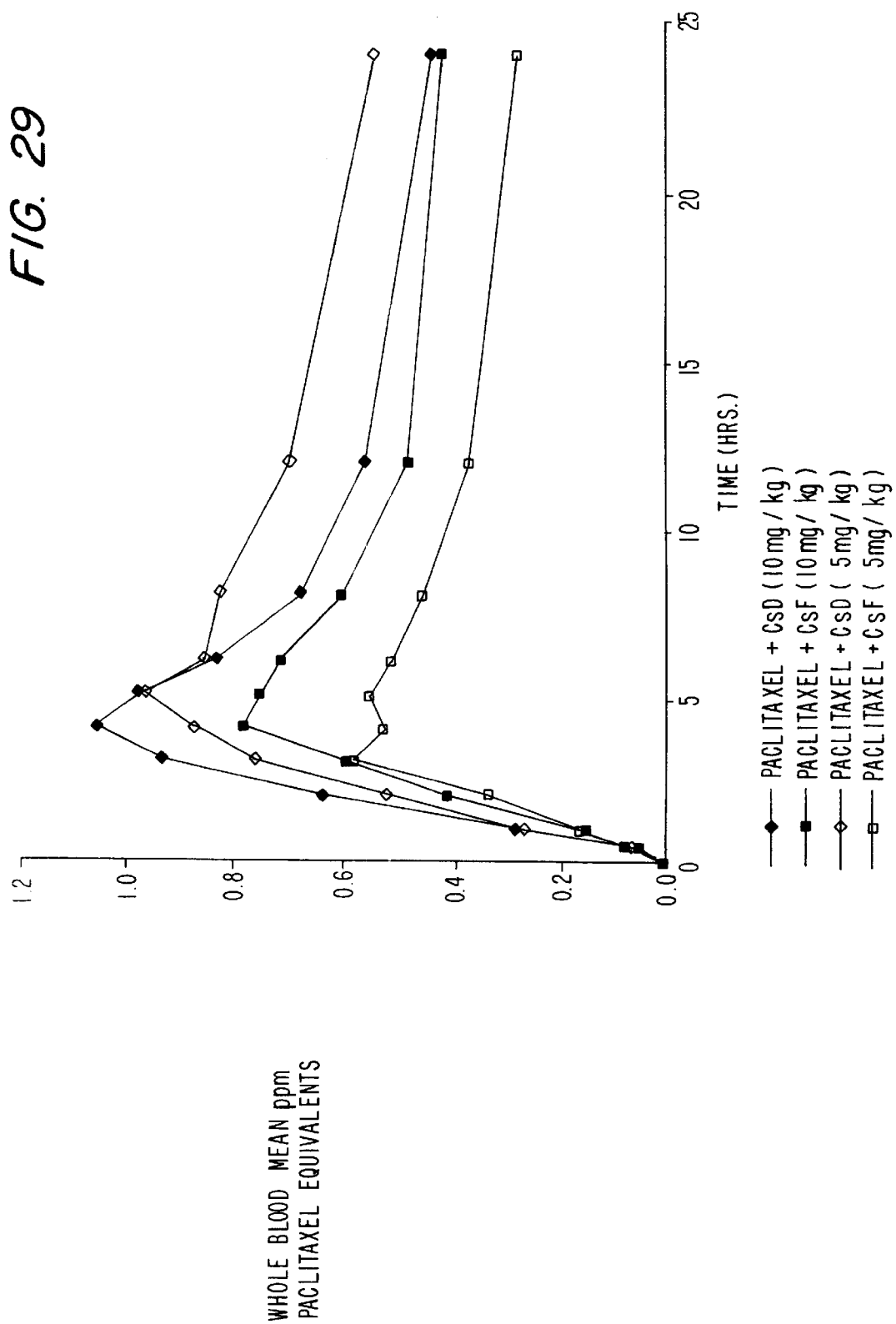

FIG. 29 is a graph reflecting the levels of radioactivity detected in whole blood samples taken from four groups of rats over a period of 24 hours: one group administered 10 mg/kg of cyclosporin D orally both one hour before and immediately after an oral dose of radiolabeled paclitaxel, a second group administered 10 mg/kg of cyclosporin F orally both one hour before and immediately after an oral dose of radiolabeled paclitaxel, a third group administered 5 mg/kg of cyclosporin D both one hour before and immediately after an oral dose of radiolabeled paclitaxel, and a fourth group administered 5 mg/kg of cyclosporin F both one hour before and immediately after an oral dose of radiolabeled paclitaxel.

Figure 30:
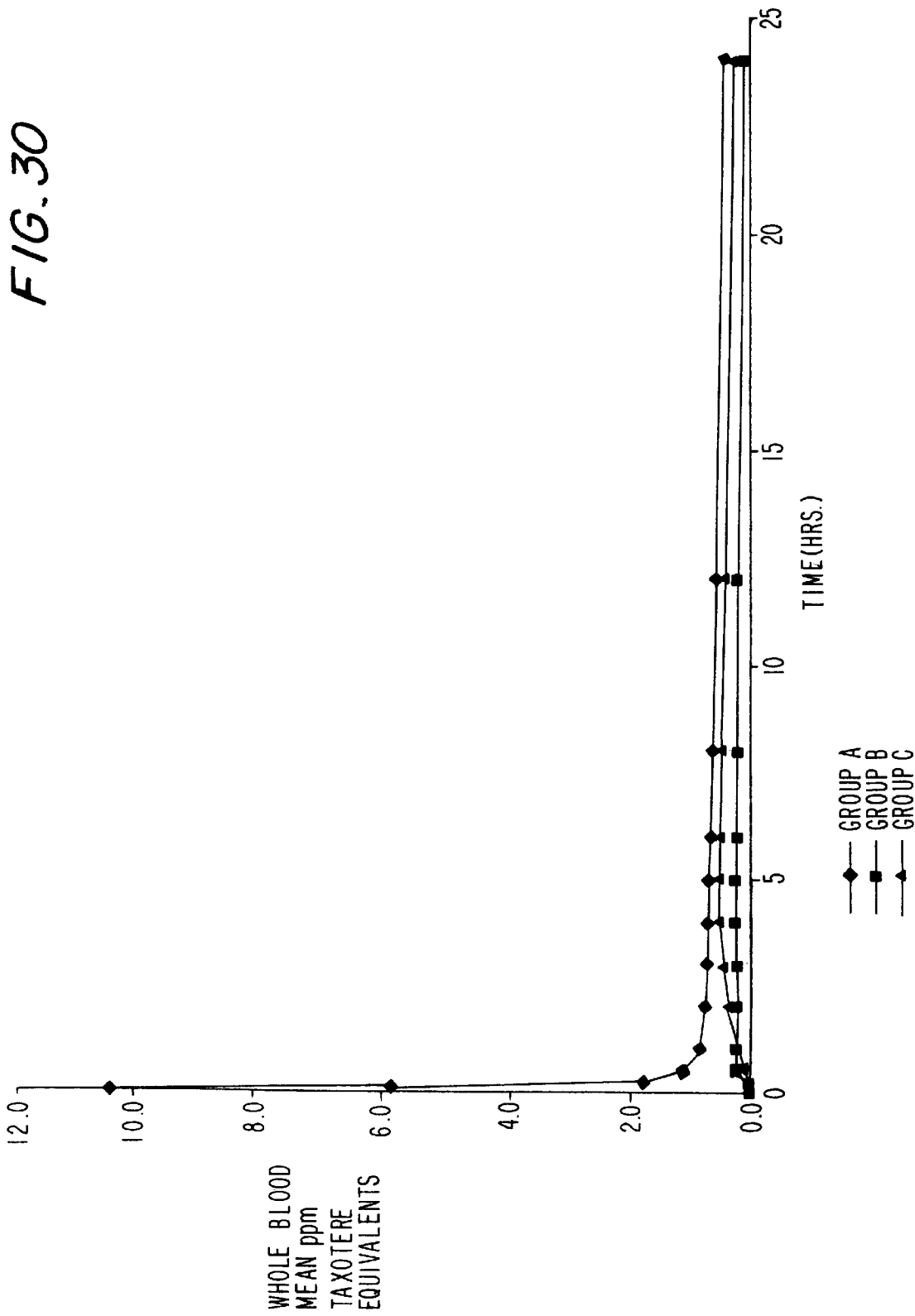

FIG. 30 is a graph reflecting the levels of radioactivity detected in whole blood samples taken from three groups of rats over a period of 24 hours: one (Group A) administered only radiolabeled docetaxel ("Taxotere") IV, a second (Group B) administered only radiolabeled docetaxel orally and a third group (Group C) administered radiolabeled docetaxel orally with oral cyclosporine doses prior to and immediately after the docetaxel dose, the ordinate of said graph running from 0–12.0 mean ppm docetaxel equivalents.

Figure 31:
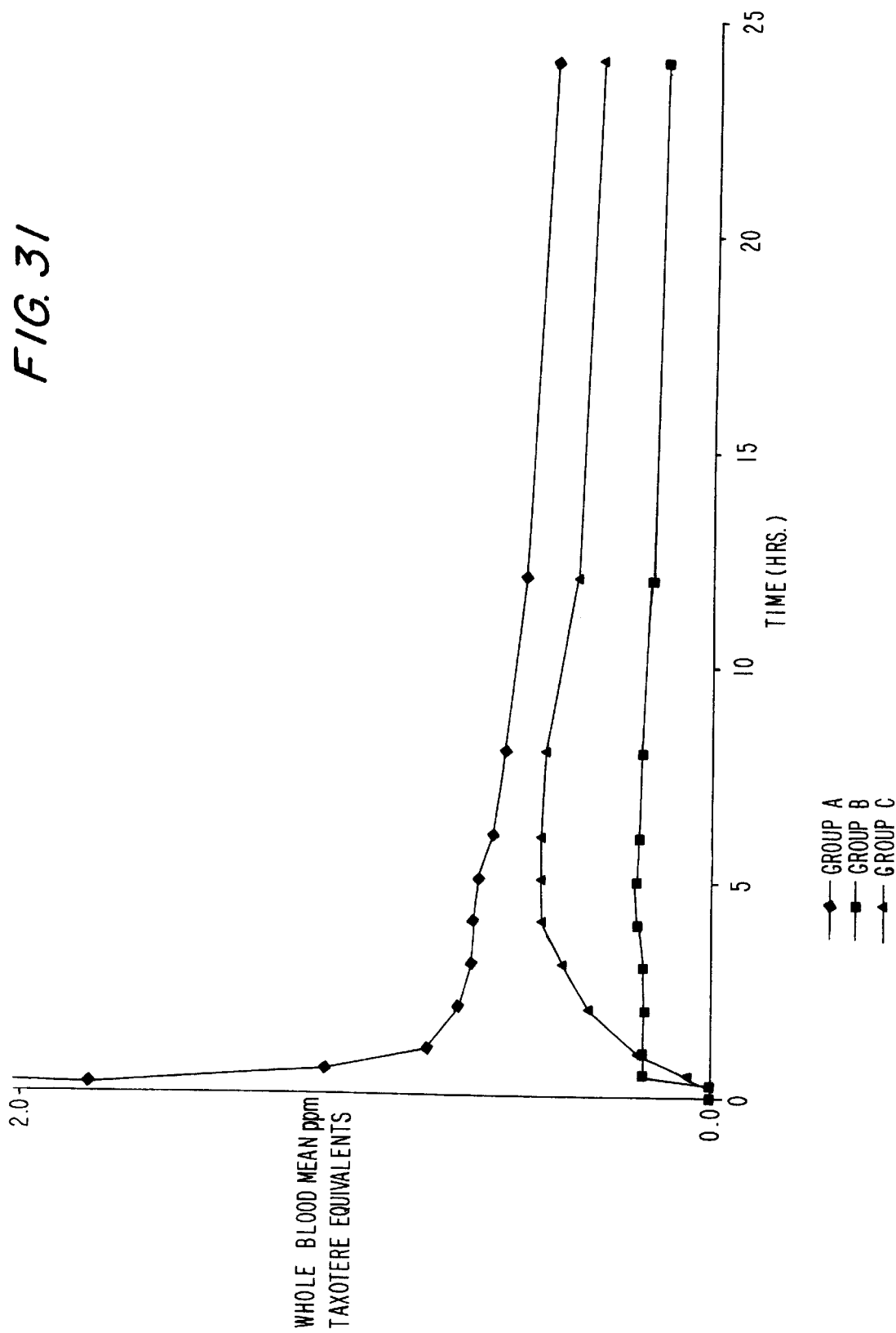

FIG. 31 is a graph reflecting the levels of radioactivity detected in whole blood samples taken from the three groups of rats defined as in FIG. 30 but with the ordinate of said graph running from 0–2.0 mean ppm docetaxel equivalents.

Figure 32:
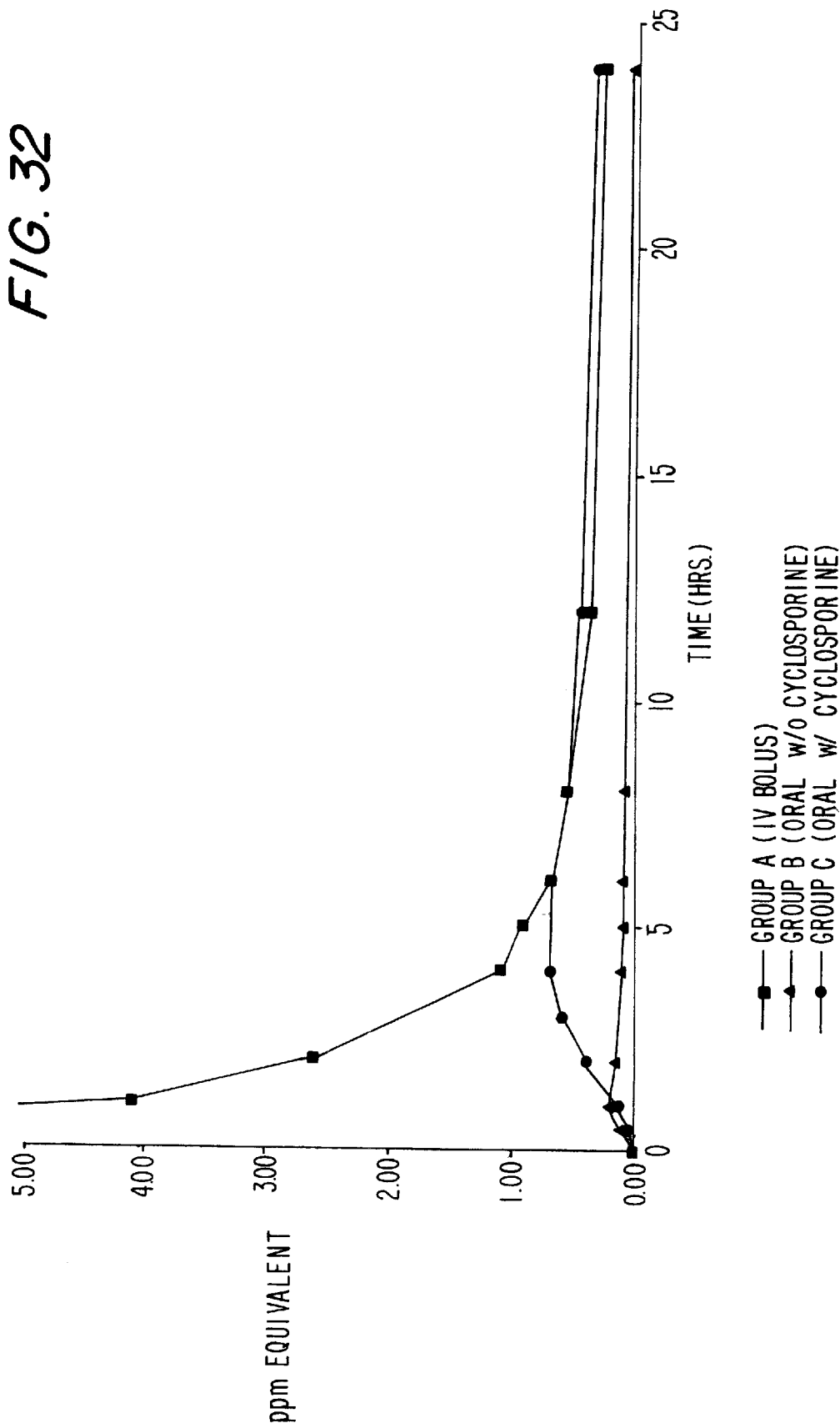

FIG. 32 is a graph reflecting the levels of radioactivity detected in whole blood samples taken from three groups of rats over a period of 24 hours: one (Group A) administered only radiolabeled paclitaxel IV, a second (Group B) administered only radiolabeled paclitaxel orally and a third group (Group C) administered radiolabeled paclitaxel orally with oral cyclosporine doses prior to and immediately after the paclitaxel dose.

Figure 33:
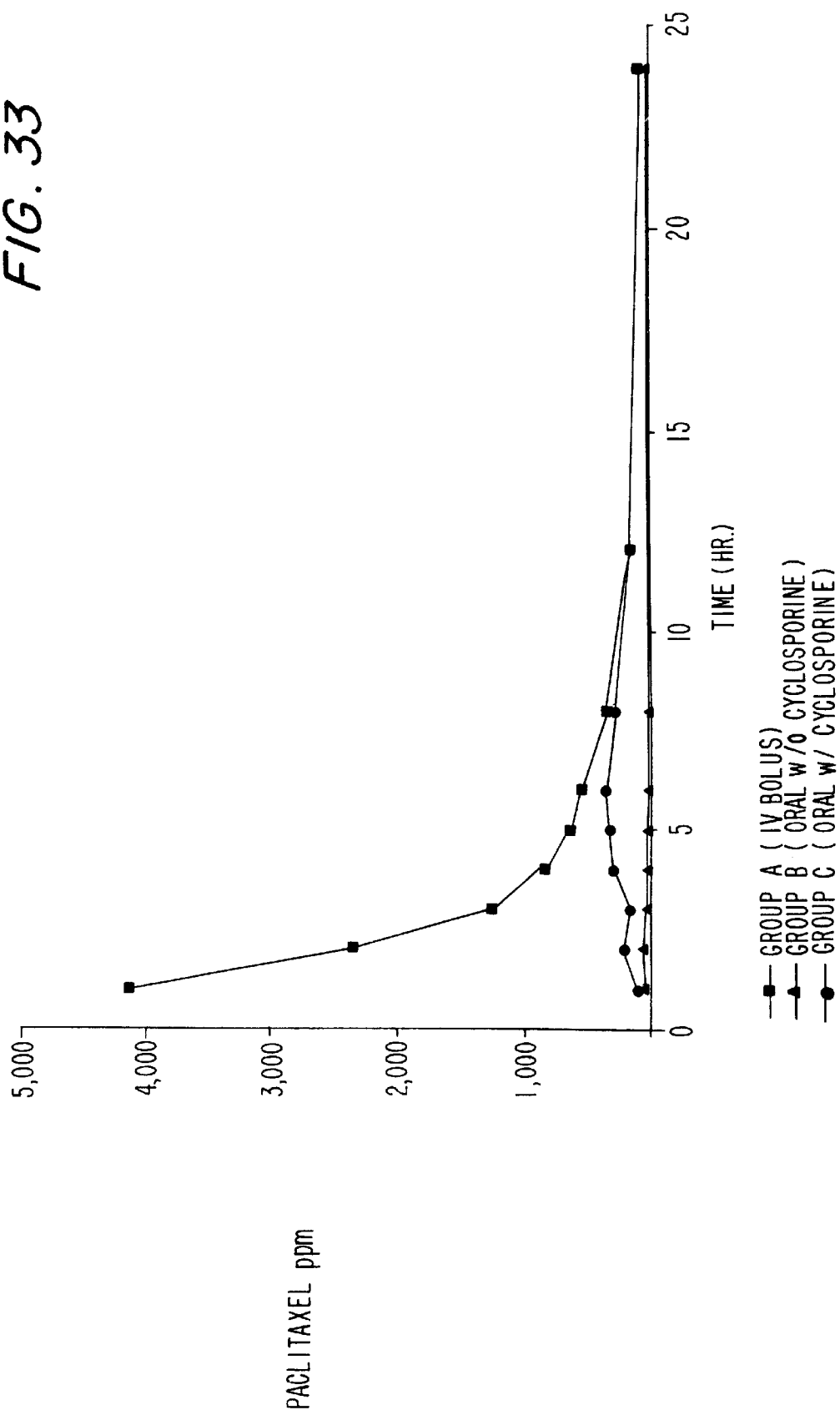

FIG. 33 is a graph reflecting the levels of unchanged radiolabeled paclitaxel detected in whole blood samples taken from the three groups of rats defined with respect to FIG. 32 from 1–24 hrs. post-dose.

Figure 34:
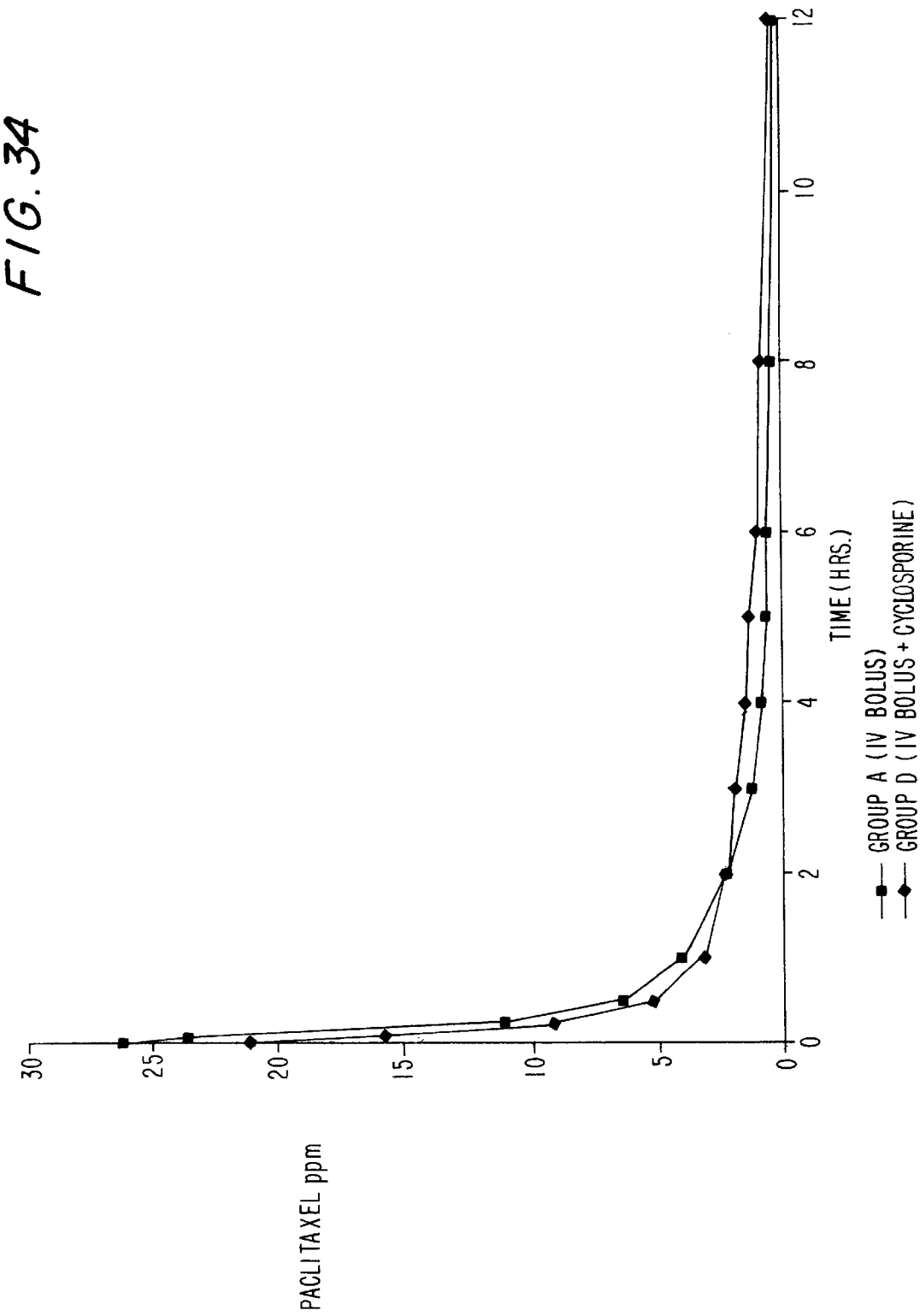

FIG. 34 is a graph reflecting the levels of unchanged radiolabeled paclitaxel detected in whole blood samples taken from 0–12 hrs. post-dose from the rats of Group A defined with respect to FIG. 32 and from a fourth group of rats (Group D) administered radiolabeled paclitaxel IV with oral cyclosporine doses prior to and immediately after the paclitaxel dose, the ordinate of said graph running from 0–30 paclitaxel ppm.

Figure 35:
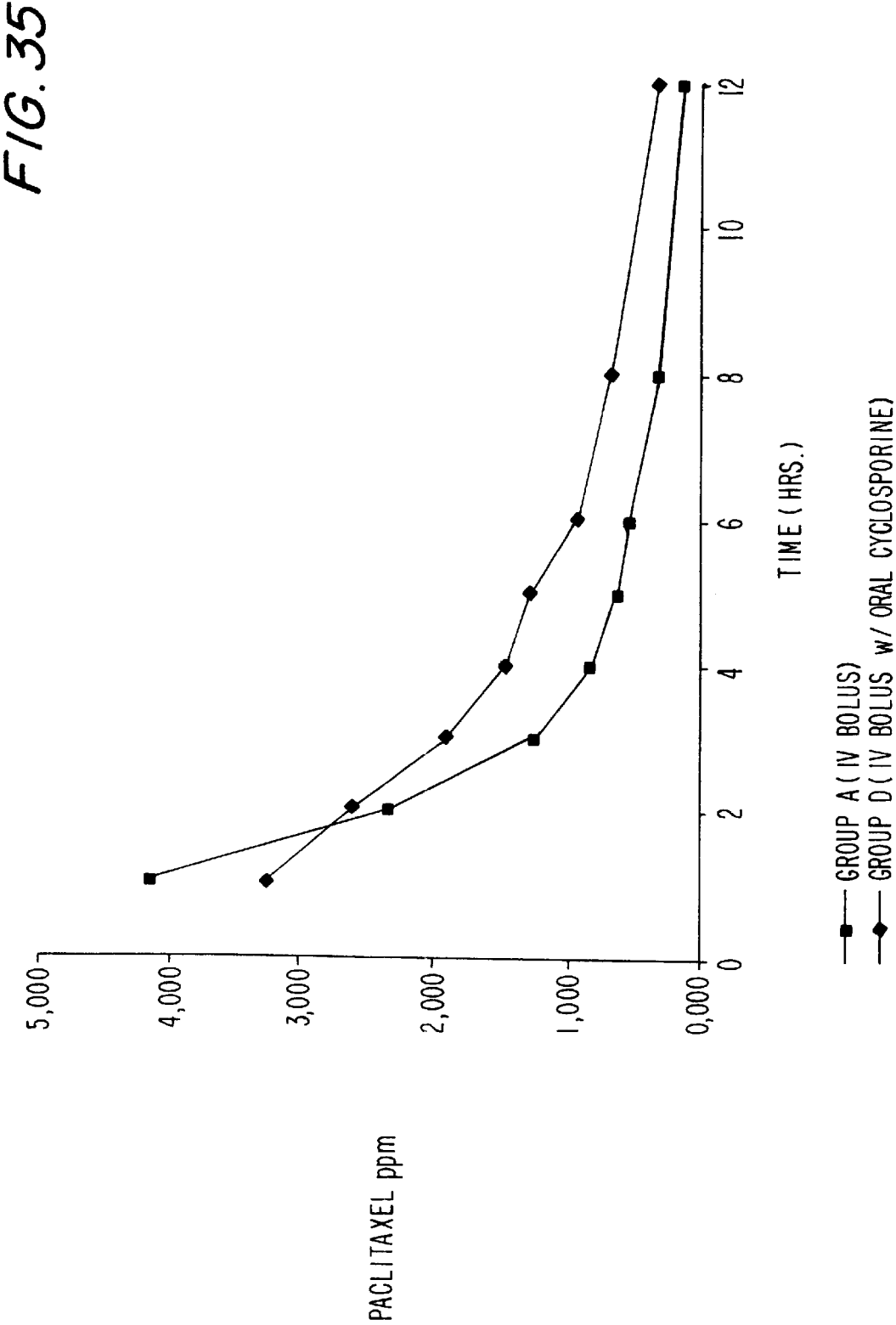
Figure 36:
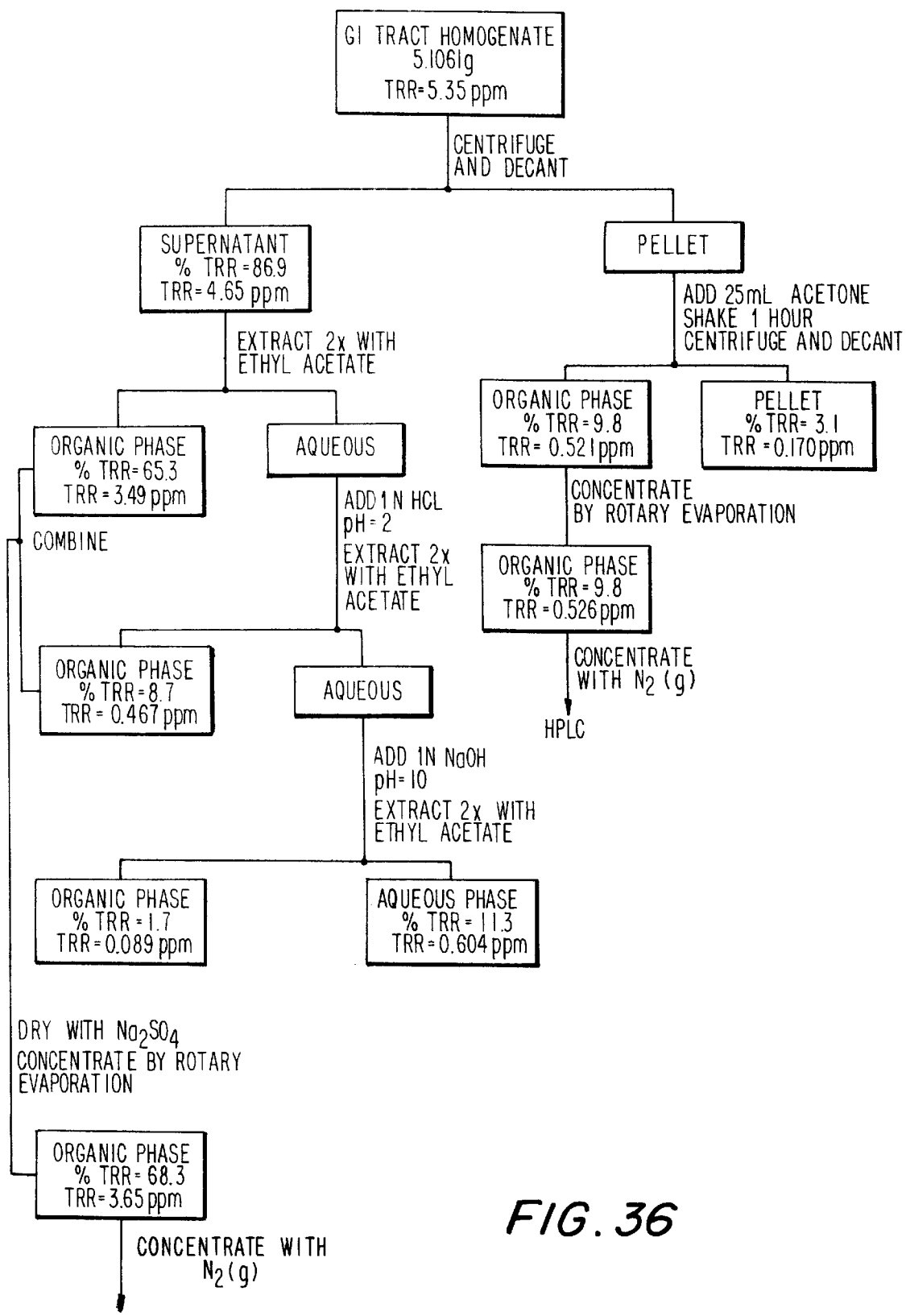
Figure 37:
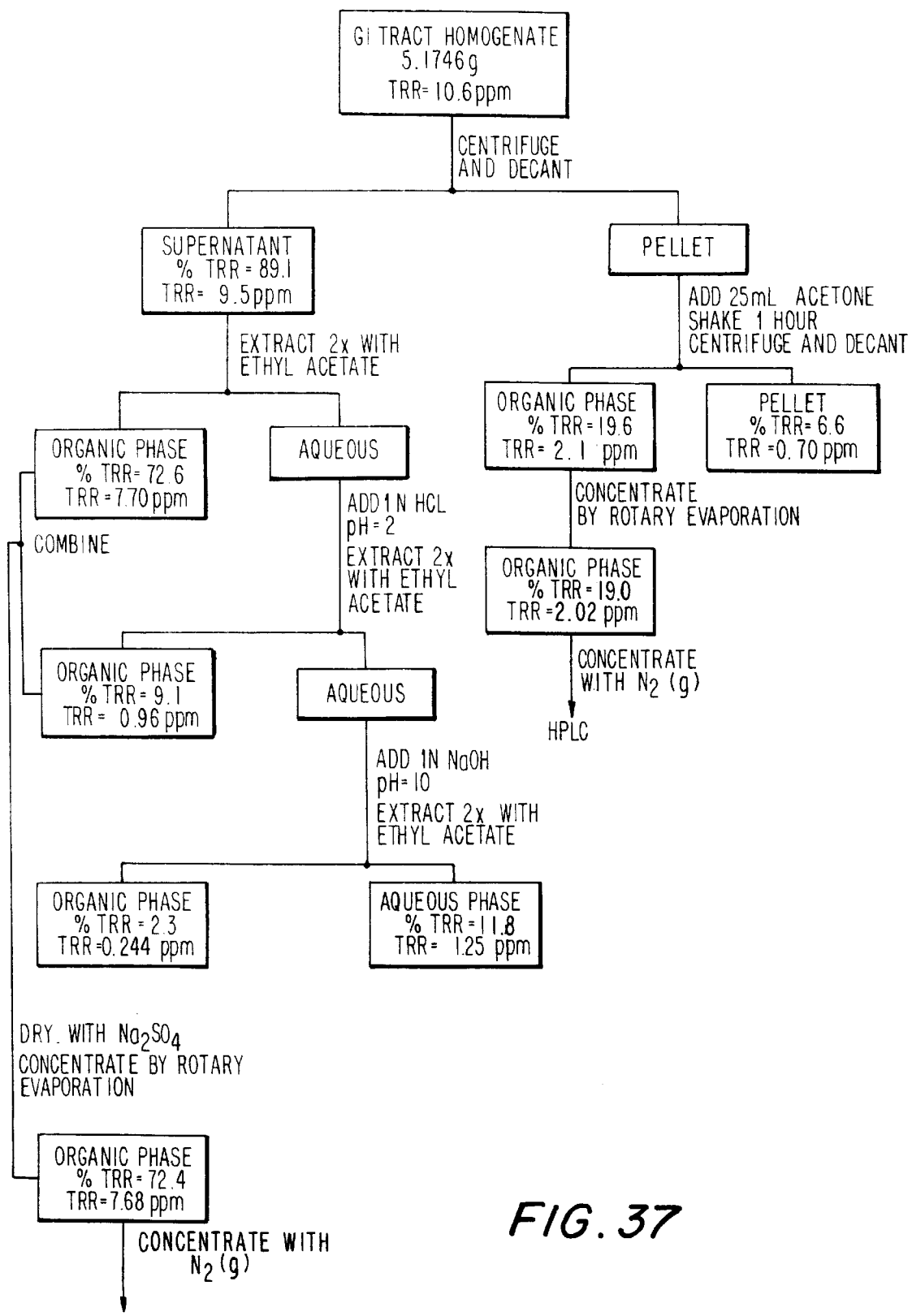
Figure 38:
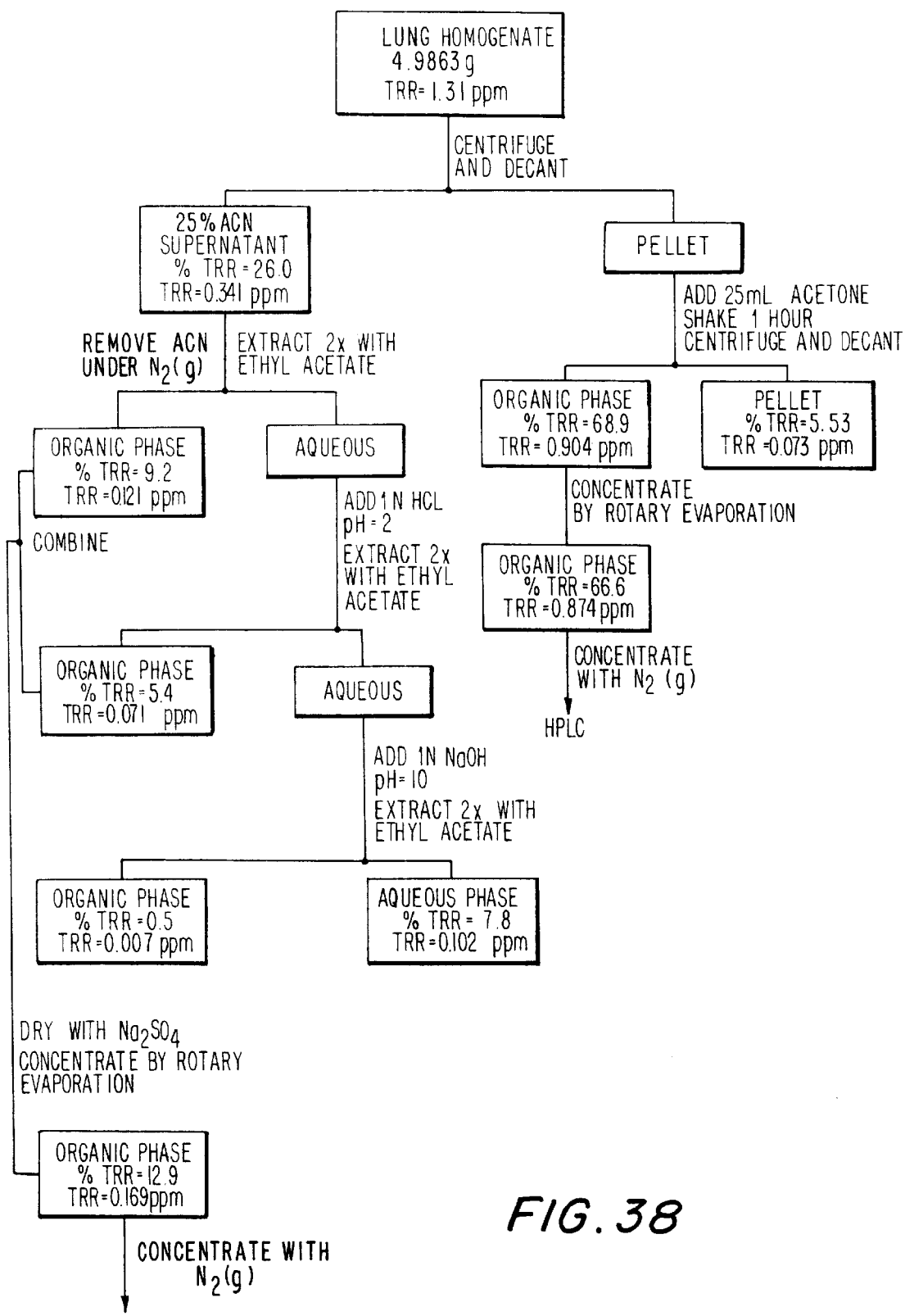
Figure 39:
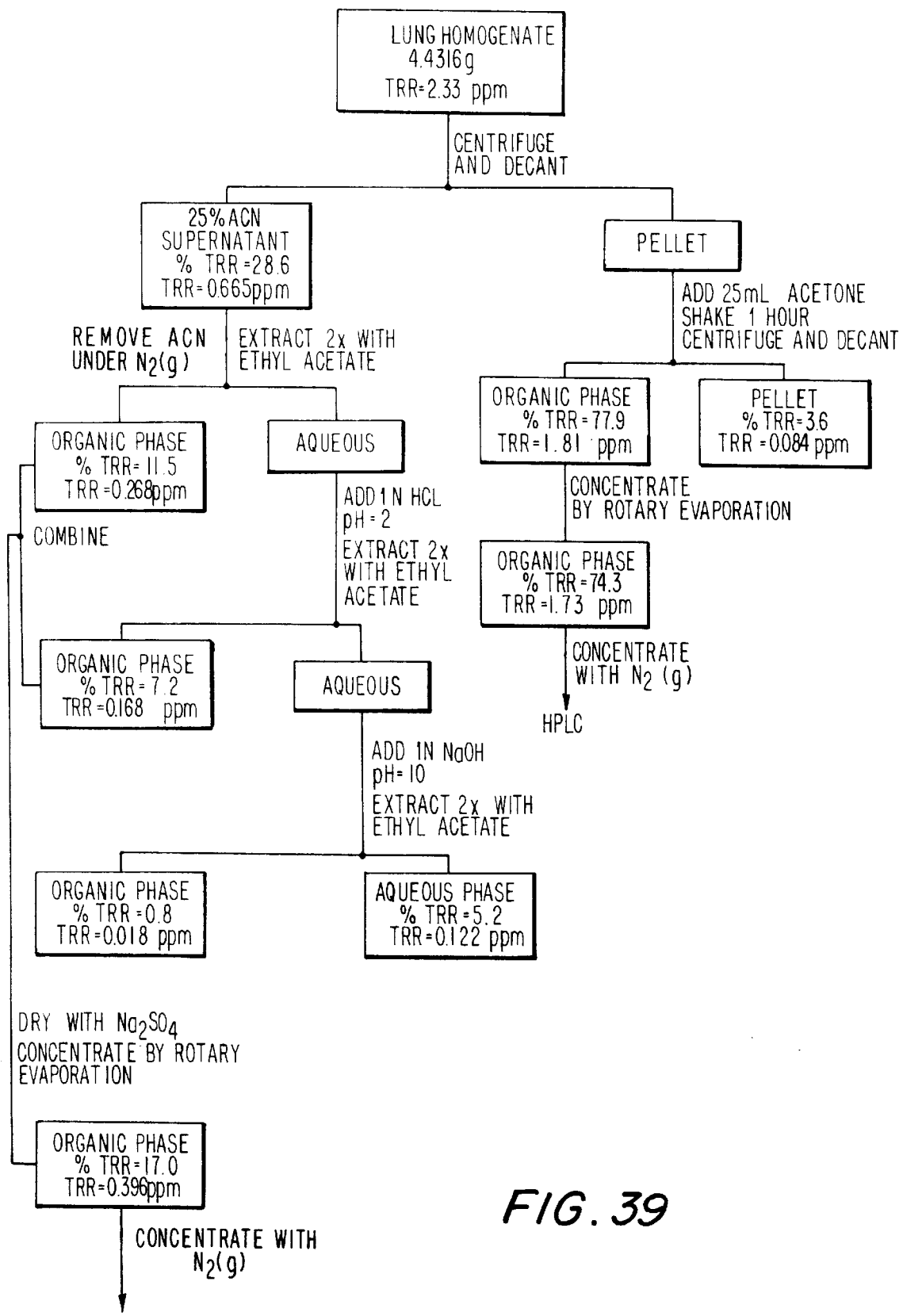
Figure 40:
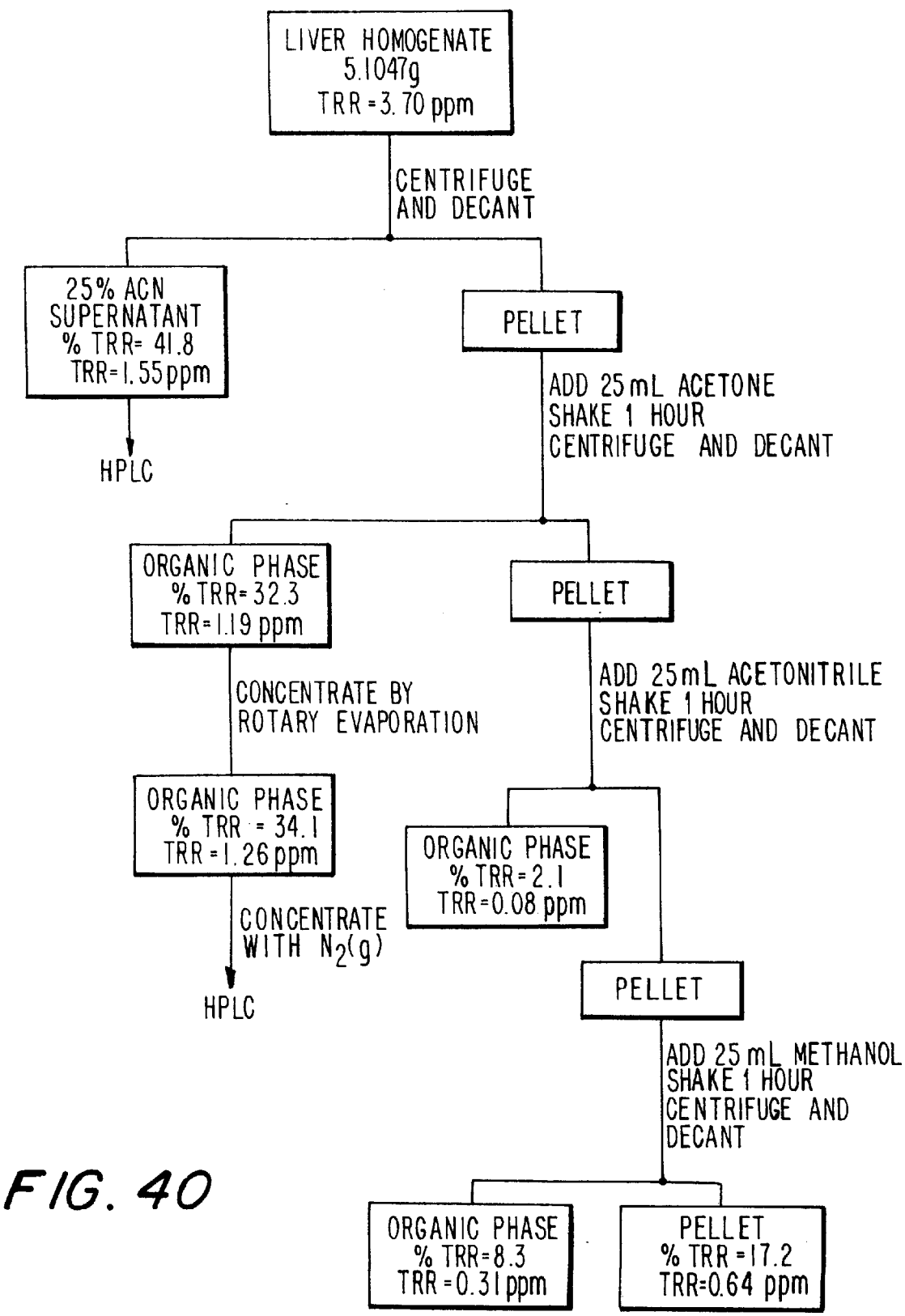
Figure 41:
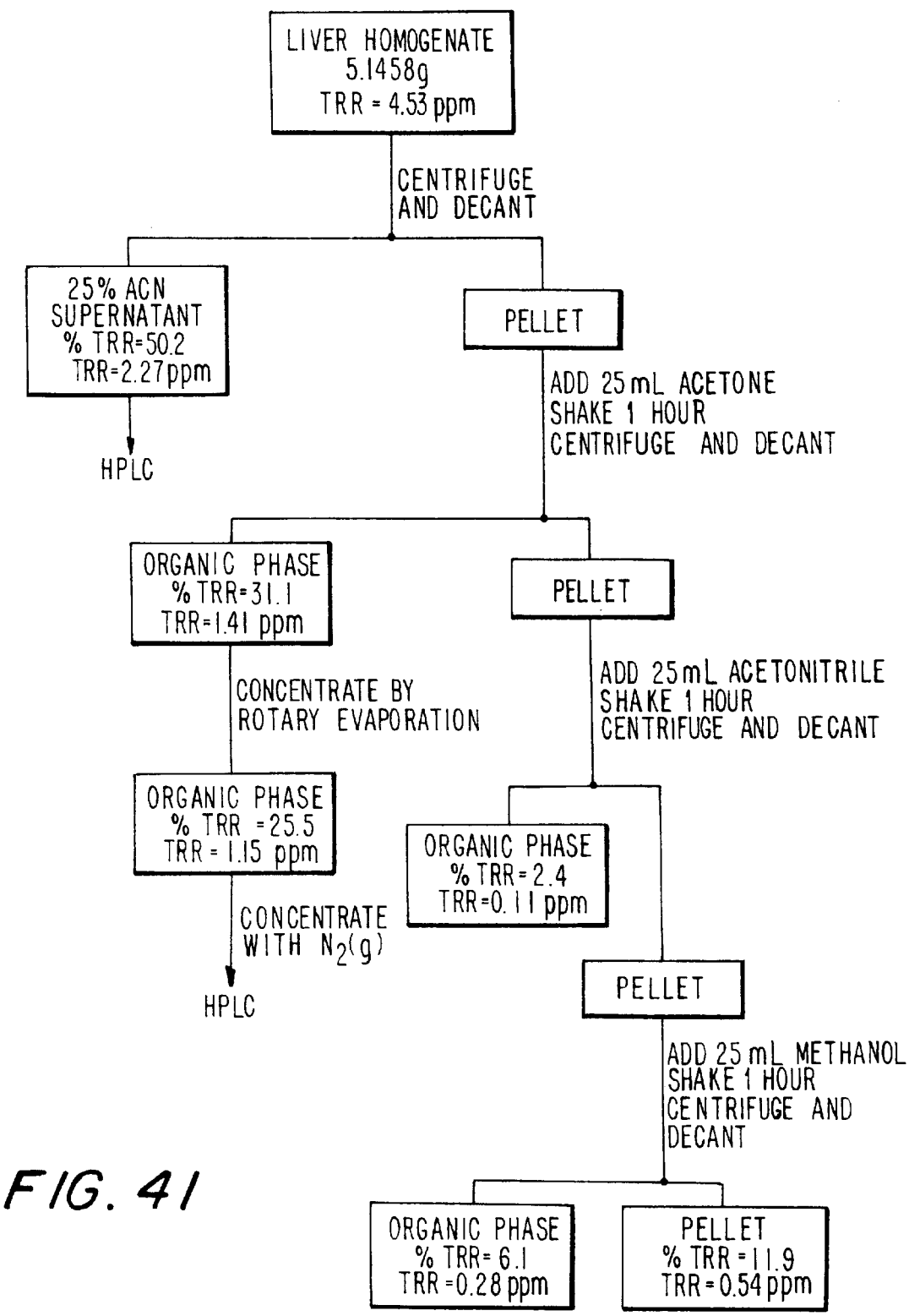

FIG. 35 is a graph reflecting the levels of unchanged radiolabeled paclitaxel detected in whole blood samples taken from 1–12 hrs. post-dose from the rats of Group A defined with respect to FIG. 32 and of Group D defined with respect to FIG. 34, the ordinate of said graph running from 0.000–5.000 paclitaxel ppm.

FIGS. 36–41 are process schemes for the extraction and partitioning of radioactivity from the composite (homogenate) of various organs of the rats of Groups A and C, respectively, as defined with respect to FIG. 32.

Figure 42:
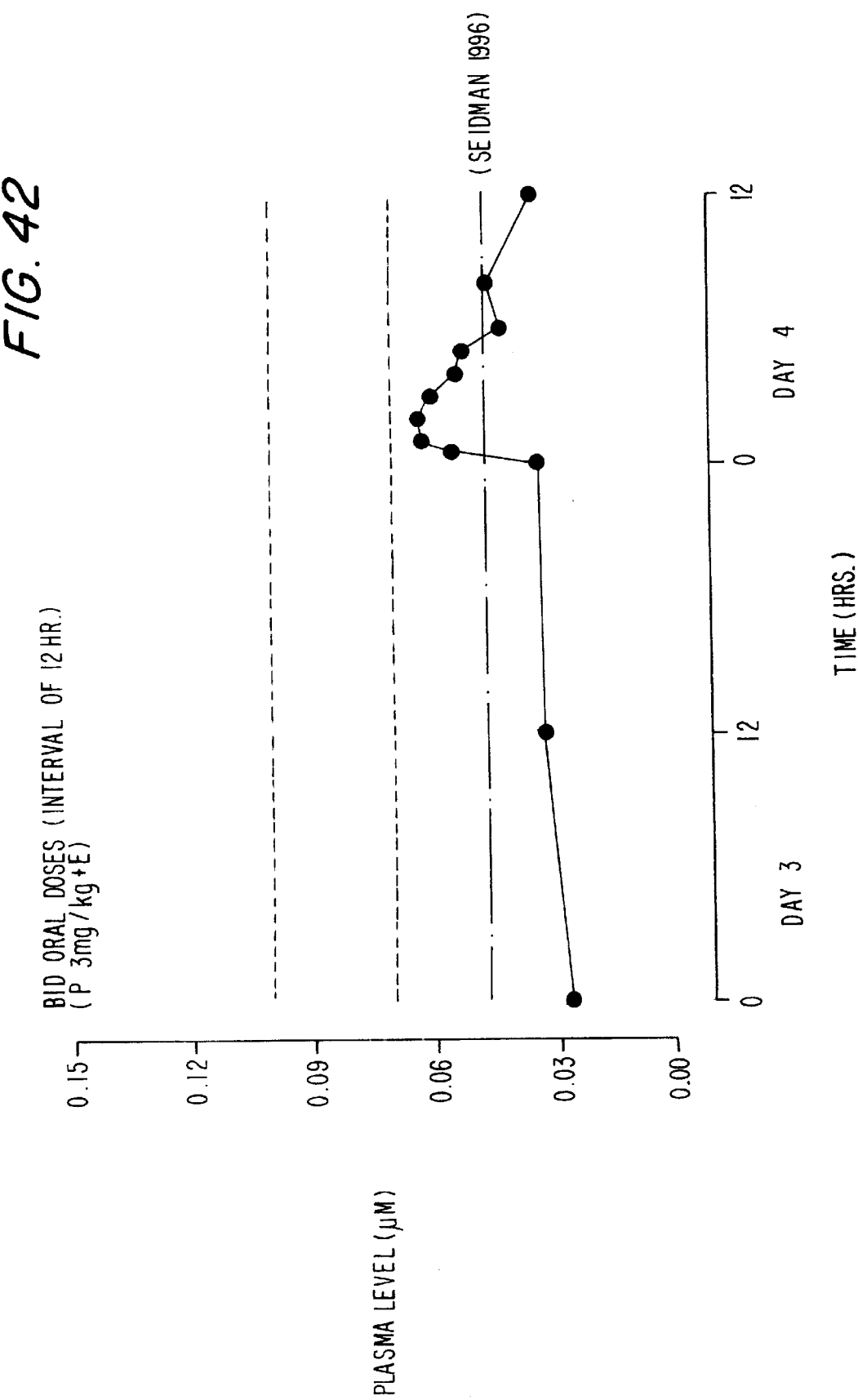

FIG. 42 is a graph reflecting the levels of paclitaxel detected in plasma samples taken at specified time intervals from a group of ten rats on the third and fourth days of a regimen whereby they were administered twice daily an oral dose (5 mg/kg) of cyclosporine and, one hour later, the combination of the same dose of oral cyclosporine plus oral paclitaxel (3 mg/kg).

DETAILED DESCRIPTION OF THE INVENTION

The present invention pertains generally to increasing the oral absorption and bioavailability upon oral administration of pharmacologically active agents, particularly agents that are poorly absorbed or not absorbed at all from the gastrointestinal tract or gut. The preferred embodiments of the invention pertain to (a) a method for increasing the oral bioavailability of antitumor agents, in particular paclitaxel (currently marketed as TAXOL® by Bristol-Myers Squibb Oncology Division) and its derivatives; other taxanes; the semi-synthetic paclitaxel analog docetaxel (N-debenzoyl-N-tert-butoxycarbonyl-10-deacetyl paclitaxel), produced under the trademark TAXOTERE® by Rhone-Poulenc Rorer S.A.; and etoposide; (b) dosage forms and kits for oral administration of antitumor agents and other drugs heretofore administered only parenterally; and (c) methods of treatment of cancer patients with such oral dosage forms or combinations thereof.

The phrases "oral bioavailability" and "bioavailability upon oral administration" as used herein refer to the systemic availability (i.e., blood/plasma levels) of a given amount of drug administered orally to a patient.

Paclitaxel is a natural diterpene product isolated from the Pacific yew tree (*Taxus brevifolia*). It is a member of the taxane family of terpenes. It was first isolated in 1971 by Wani et al. (*J. Am. Chem. Soc.*, 93:2325, 1971), who characterized its structure by chemical and X-ray crystallographic methods. One mechanism for its activity relates to paclitaxel's capacity to bind tubulin, thereby inhibiting cancer cell growth. Schiff et al., *Proc. Natl. Acad. Sci. USA*, 77:1561–1565 (1980); Schiff et al., *Nature*, 277:665–667 (1979); Kumar, *J. Biol. Chem.*, 256: 10435–10441 (1981).

Paclitaxel has been approved for clinical use in the treatment of refractory ovarian cancer in the United States (Markman et al., *Yale Journal of Biology and Medicine*, 64:583, 1991; McGuire et al., *Ann. Intern. Med.*, 111:273, 1989). It is effective for chemotherapy for several types of neoplasms including breast (Holmes et al., *J. Nat. Cancer Inst.*, 83:1797, 1991) and has been approved for treatment of breast cancer as well. It is a potential candidate for treatment of neoplasms in the skin (Einzig et al., *Proc. Am. Soc. Clin. Oncol.*, 20:46) and head and neck carcinomas (Forastire et al. *Sem. Oncol.*, 20:56, 1990). The compound also shows potential for the treatment of polycystic kidney disease (Woo et al., *Nature*, 368:750, 1994), lung cancer and malaria.

Paclitaxel is only slightly soluble in water and this has created significant problems in developing suitable injectable and infusion formulations useful for anticancer chemotherapy. Some formulations of paclitaxel for IV infusion have been developed utilizing CREMOPHOR EL™ (polyethoxylated castor oil) as the drug carrier because of paclitaxel's aqueous insolubility. For example, paclitaxel used in clinical testing under the aegis of the NCI has been formulated in 50% CREMOPHOR EL™ and 50% dehydrated alcohol. CREMOPHOR EL™ however, when administered intravenously, is itself toxic and produces vasodilation, labored breathing, lethargy, hypotension and death in dogs. It is also believed to be responsible for the allergic-type reactions observed during paclitaxel administration.

In an attempt to increase paclitaxel's solubility and to develop more safe clinical formulations, studies have been directed to synthesizing paclitaxel analogs where the 2' and/or 7-position is derivatized with groups that would enhance water solubility. These efforts have yielded prodrug compounds that are more water soluble than the parent compound and that display the cytotoxic properties upon activation. One important group of such prodrugs includes the 2'-onium salts of paclitaxel and docetaxel, particularly the 2'-methylpyridinium mesylate (2'-MPM) salts.

Paclitaxel is very poorly absorbed when administered orally (less than 1%); see Eiseman et al., *Second NCI Workshop on Taxol and Taxus* (Sept. 1992); Stuffness et al. in *Taxol Science and Applications* (CRC Press 1995). Eiseman et al. indicate that paclitaxel has a bioavailability of 0% upon oral administration, and Stuffness et al. report that oral dosing with paclitaxel did not seem possible since no evidence of antitumor activity was found on oral administration up to 160 mg/kg/day. Moreover, no effective method has been developed to enable the effective administration of oral paclitaxel (i.e., a method of increasing the oral bioavailability of paclitaxel) or of other oral taxanes or paclitaxel analogs such as docetaxel which exhibit antitumor activity. For this reason, paclitaxel has not until now been administered orally to human patients, and certainly not in the course of treating paclitaxel-responsive diseases.

Docetaxel has become commercially available as TAXOTERE® in parenteral form for the treatment of breast cancer. To date no reference has been made in the scientific literature to oral absorption of docetaxel in animals or patients.

Etoposide is a semisynthetic derivative of podophyllotoxin and is used in the treatment of certain neoplastic diseases, particularly germ cell cancers (e.g., testicular cancers) and small cell lung cancers (Loehrer, *Sem. Onc.*, 19, no. 6, supp. 14, pp. 48–52, 1992). It is available in oral dosage form (VEPESID® capsules, Bristol-Myers Squibb Oncology) but is not consistently well-absorbed orally (the mean value of oral bioavailability for etoposide capsules is approximately 50%).

Cyclosporins are a group of nonpolar cyclic oligopeptides (some of which have immunosuppressant activity) produced by the genus Topycladium, including, e.g. Topycladium inflatum Gams (formerly designated as *Trichoderma polysporum*), *Topycladium terricola* and other fungi imperfecti. The major component, cyclosporin A (cyclosporine or CsA), has been identified along with several other lesser metabolites, for example, cyclosporins B through Z, some of which exhibit substantially less immunosuppressive activity than cyclosporin A. A number of synthetic and semi-synthetic analogs have also been prepared. See generally Jegorov et al., *Phychemistry*, 38: 403–407 (1995). The present invention comprehends natural, semi-synthetic and synthetic analogs of cyclosporins.

Cyclosporins are neutral, lipophilic, cyclic undecapeptides with molecular weights of about 1200. They are used intravenously or orally as immunosuppressants, primarily for organ transplantation and certain other conditions. Cyclosporins, particularly cyclosporine (cyclosporin A), are known inhibitors of the P-glycoprotein efflux pump, as well as of certain P450 degradative enzymes, but to date no effective regimens for applying this property clinically have been developed to the point of clinical and commercial feasibility or regulatory approval.

From a mechanistic point of view, orally administered cyclosporine has the potential to inhibit the P-glycoprotein pump in the upper small intestine which is the site at which most drugs are absorbed. With intravenous administration of a drug which is highly metabolized like cyclosporine, it is not possible for it to appear intact in that region of the gut where drugs are normally absorbed. After parenteral administration, cyclosporine is extracted by the liver and enters the bile and gut distal to this area of optimal absorption. One of the surprising discoveries of the invention is that the immunosuppression observed with certain cyclosporins is not inextricably linked to improvement in oral bioavailability of therapeutic agents. Thus, cyclosporin F enhances the oral bioavailability of paclitaxel even though, according to reports in the literature, it does not display immunosuppressive activity. Stewart et al., *Transplantation Proceedings*, 20:(Supp. 3) 989–992 (1988); Granelli-Piperno et al., *Transplantation*, 46:53S–60S (1988).

Ketoconazole is a widely used antifungal imidazole derivative which has also been used to some extent in the treatment of prostate carcinoma. Ketoconazole has been shown, as one of its activities, to reverse MDR in highly resistant human KB carcinoma cells (Siegsmund et al., *J. Urology*, 151: 485–491, 1994), but also can inhibit the cytochrome P-450 drug-metabolizing enzymes.

It has now been discovered that many pharmaceutical agents with poor oral absorption profiles can be effectively administered orally with sufficient systemic absorption to exhibit therapeutic activity levels when said agents are co-administered orally with an oral dose of certain cyclosporins or other agents known to inhibit the multidrug resistance, drug transport activity of the P-glycoprotein intracellular pump, as well as certain enhancing agents whose ability to inhibit P-glycoprotein transport has not yet been determined. A further surprising discovery of our invention is that under some conditions, the oral administration leads to a more favorable pharmacokinetic profile, better tissue penetration and higher volume of distribution of the target therapeutic agent.

We have observed in animal studies that certain multidrug resistance suppressing agents such as cyclosporine and ketoconazole, when administered orally immediately after and/or before drugs such as paclitaxel and etoposide, increase absorption of the latter drugs from the gut to an unexpected and surprising degree resulting in therapeutic levels being achieved. It is not at all clear, however, that these observed results are due to the suppression of the P-glycoprotein pump.

Another possible explanation for the observed increased bioavailability of paclitaxel and etoposide is that there may be interaction at the level of the drug metabolizing enzymes for cyclosporine and paclitaxel. It is known that both agents are highly metabolized by the cytochrome P450 system (e.g., P450 3A), which is concentrated in the liver as well as the small intestine. It is conceivable that cyclosporine which was administered first may have inhibited these enzymes so that paclitaxel, which is non-polar and lipophilic, could be absorbed. In the absence of this local inhibition, paclitaxel would be metabolized to more polar metabolites which would not transverse the mucosal cells. The failure to demonstrate a pharmacokinetic interaction between cyclosporin and paclitaxel when cyclosporin was given 3 hr prior to administration of IV paclitaxel suggests that the site of interaction was the gut lumen. Even this theoretical explanation does not account for our surprising discovery that certain P-glycoprotein inhibitors (e.g., cyclosporins and ketoconazole) increase oral bioavailability of specific target drugs to a high degree, whereas other agents known to be active P-glycoprotein inhibitors exhibit little activity as oral absorption enhancers for the same target drugs.

This theorized inhibition of gut metabolism of the target agent would have little or no effect in increasing systemic blood levels when the target agent is administered intravenously. Moreover, since the primary effect of the oral absorption enhancing agent may be a local effect in the gut lumen, subtherapeutic doses should be effective in achieving the desired effect. This is an important consideration in the case of enhancing agents such as cyclosporins which have powerful immunosuppressant activity and can present toxicity problems if administered at high dose levels. Our observation that non-immunosuppressive cyclosporins, such as cyclosporin F, can still function as an oral enhancer is of great clinical value.

It is important to note that while we provide hypotheses as to the mechanisms of action which underlie our invention, we do not actually know the mechanism(s) responsible for the surprising findings discussed herein; and this does not impede one of skill in the art from practicing the invention described.

The method of the invention for increasing the oral bioavailability of a target therapeutic agent with poor oral bioavailability (average or mean bioavailability 50% or less) comprises the oral administration of an oral absorption or bioavailability enhancing agent to a mammalian patient (human or animal) simultaneously with, or prior to, or both simultaneously with and prior to the oral administration to increase the quantity and duration of absorption of the intact target agent into the bloodstream.

The orally administered enhancing agents which may be used in accordance with the invention include, but are not limited to, the following:

Cyclosporins, including cyclosporins A through Z but particularly cyclosporin A (cyclosporine), cyclosporin F, cyclosporin D, dihydro cyclosporin A, dihydro cyclosporin C, acetyl cyclosporin A, PSC-833, SDZ-NIM 811[2] (both from Sandoz Pharmaceutical Corp.), and related oligopeptides produced by species in the genus Topygladium. The structures of cyclosporins A–Z are described in Table 1 below.

[2]SDZ-NIM 811 is (Me-lle-4)-closporin, an antiviral, non-immunosuppressive cyclosporin.

Antifungals—ketoconazole.

Cardiovascular drugs—MS-209 (from BASF), amiodarone, nifedipine, reserpine, quinidine, nicardipine, ethacrynic acid, propafenone, reserpine, amiloride.

Anti-migraine natural products—ergot alkaloids.

Antibiotics—cefoperazone, tetracycline, chloroquine, fosfomycin.

Antiparasitics—ivermectin.

Mufti-drug resistance reversers—VX-710 and VX-853 (Vertex Pharmaceutical Incorporated).

Tyrosine kinase inhibitors—genistein and related isoflavonoids, quercetin.

Protein kinase C inhibitors—calphostin.

Apoptosis inducers—ceramides.

Agents active against endorphin receptors—morphine, morphine congeners, other opioids and opioid antagonists including (but not limited to) naloxone, naltrexone and nalmefene).

The class of orally administered target therapeutic agents whose oral absorption is increased by the enhancing agents includes, but is not limited to, the following:

Paclitaxel, other taxanes, docetaxel and derivatives and prodrugs of all of the foregoing, particularly their 2'-MPM salts and other 2'-methylpyridinium salts.

Other chemotherapeutic agents which have poor or highly variable oral bioavailability including etoposide, camptothecin, CPT-11 (Pharmacia and Upjohn), topetecan (SmithKline Beecham), doxorubicin, vincristine, daunorubicin, mitoxantrone and colchicine, all of which are believed to be affected by the P-glycoprotein efflux.

Other drugs which have not been shown to be handled by P-glycoprotein but which can be made orally absorbable in the presence of an inhibitor of P-glycoprotein in the gut, including ganciclovir, foscarnet, camptothecin and camptothecin derivatives.

the administration of the target agent, or both, i.e., with one or more doses of the same or different enhancing agents given at least 0.5 hr. before and one dose given substantially simultaneously with (either together with or immediately before of after) the target agent. Additionally, "co-

TABLE 1

Cyclosporins A–Z

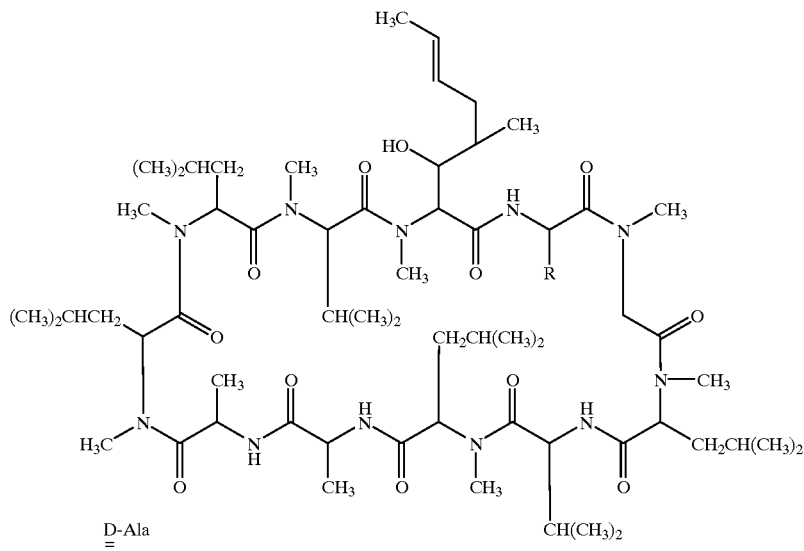

| Cyclosporin | Aminoacids | | | | | | | | | | |
|---|---|---|---|---|---|---|---|---|---|---|---|
| Cy- | 1 | 2 | 3 | 4 | 5 | 6 | 7 | 8 | 9 | 10 | 11 |
| Cy A | Mebmt | Abu | Sar | MeLeu | Val | MeLeu | Ala | D-Ala | MeLeu | MeLeu | MeVal |
| Cy B | Mebmt | Ala | Sar | MeLeu | Val | MeLeu | Ala | D-Ala | MeLeu | MeLeu | MeVal |
| Cy C | Mebmt | Thr | Sar | MeLeu | Val | MeLeu | Ala | D-Ala | MeLeu | MeLeu | MeVal |
| Cy D | Mebmt | Val | Sar | MeLeu | Val | MeLeu | Ala | D-Ala | MeLeu | MeLeu | MeVal |
| Cy E | Mebmt | Abu | Sar | MeLeu | Val | MeLeu | Ala | D-Ala | MeLeu | MeLeu | Val |
| Cy F | Desoxy-Mebmt | Abu | Sar | MeLeu | Val | MeLeu | Ala | D-Ala | MeLeu | MeLeu | MeVal |
| Cy G | Mebmt | Nva | Sar | MeLeu | Val | MeLeu | Ala | D-Ala | MeLeu | MeLeu | MeVal |
| Cy H | Mebmt | Abu | Sar | MeLeu | Val | MeLeu | Ala | D-Ala | MeLeu | MeLeu | D-Mev |
| Cy I | Mebmt | Val | Sar | MeLeu | Val | MeLeu | Ala | D-Ala | MeLeu | Leu | MeVal |
| Cy K | Desoxy-Mebmt | Val | Sar | MeLeu | Val | MeLeu | Ala | D-Ala | MeLeu | MeLeu | MeVal |
| Cy L | Bmt | Abu | Sar | MeLeu | Val | MeLeu | Ala | D-Ala | MeLeu | MeLeu | MeVal |
| Cy M | Mebmt | Nva | Sar | MeLeu | Val | MeLeu | Ala | D-Ala | MeLeu | MeLeu | MeVal |
| Cy N | Mebmt | Nva | Sar | MeLeu | Val | MeLeu | Ala | D-Ala | MeLeu | Leu | MeVal |
| Cy O | MeLeu | Nva | Sar | MeLeu | Val | MeLeu | Ala | D-Ala | MeLeu | MeLeu | MeVal |
| Cy P | Bmt | Thr | Sar | MeLeu | Val | MeLeu | Ala | D-Ala | MeLeu | MeLeu | MeVal |
| Cy Q | Mebmt | Abu | Sar | Val | Val | MeLeu | Ala | D-Ala | MeLeu | MeLeu | MeVal |
| Cy R | Mebmt | Abu | Sar | MeLeu | Val | Leu | Ala | D-Ala | MeLeu | Leu | MeVal |
| Cy S | Mebmt | Thr | Sar | Val | Val | MeLeu | Ala | D-Ala | MeLeu | MeLeu | MeVal |
| Cy T | Mebmt | Abu | Sar | MeLeu | Val | MeLeu | Ala | D-Ala | MeLeu | Leu | MeVal |
| Cy U | Mebmt | Abu | Sar | MeLeu | Val | Leu | Ala | D-Ala | MeLeu | MeLeu | MeVal |
| Cy V | Mebmt | Abu | Sar | MeLeu | Val | MeLeu | Ala | D-Ala | MeLeu | MeLeu | MeVal |
| Cy W | Mebmt | Thr | Sar | MeLeu | Val | MeLeu | Ala | D-Ala | MeLeu | MeLeu | Val |
| Cy X | Mebmt | Nva | Sar | MeLeu | Val | MeLeu | Ala | D-Ala | Leu | MeLeu | MeVal |
| Cy Y | Mebmt | Nva | Sar | MeLeu | Val | Leu | Ala | D-Ala | MeLeu | MeLeu | MeVal |
| Cy Z | MeAminooctylacid | Abu | Sar | MeLeu | Val | MeLeu | Ala | D-Ala | MeLeu | MeLeu | MeVal |

The dosage range of the enhancing agent to be co-administered with the target agent in accordance with the invention is about 0.1 to about 15 mg/kg of patient body weight. "Co-administration" of the enhancing agent comprehends administration substantially simultaneously with the target agent (either less than 0.5 hr. before, less than 0.5 hr. after or together), from about 0.5 to about 24 hr. before administration" comprehends administering more than one dose of target agent within 24 hrs after a dose of enhancing agent, in other words, the enhancing agent(s) need not be administered again before or with every administration of target agent, but may be administered intermittently during the course of treatment.

The dosage range of orally administered target agents will vary from drug to drug based on its therapeutic index, the requirements of the condition being treated, the status of the subject and so forth. The method of the invention makes it possible to administer paclitaxel orally ranging from about 20 mg/m$^2$ to about 1000 mg/m$^2$ (based on patient body surface area) or about 2–30 mg/kg (based on patient body weight) as single or divided (2–3) daily doses, and maintain the plasma levels of paclitaxel in humans in the range of 50–500 mg/ml for extended periods of time (e.g., 8–12 hours) after each oral dose. These levels are at least comparable to those achieved with 96-hour IV infusion taxol therapy (which causes the patient great inconvenience, discomfort, loss of time, infection potential, etc.). Moreover, such plasma levels of paclitaxel are more than sufficient to provide the desired pharmacological activities of the target drug, e.g., inhibition of tubulin disassembly (which occurs at levels of about 0.1 $\mu$M, or about 85 ng/ml) and inhibition of protein isoprenylation (which occurs at levels of about 0.03 $\mu$M, or about 25 ng/ml) which are directly related to its antitumor effects by inhibiting oncogene functions and other signal-transducing proteins that play a pivotal role in cell growth regulation.

It may be suitable in some instances to administer to the subject a higher initial loading dose of the target agent to achieve peak blood levels, followed by lower maintenance doses.

Two or more different enhancing agents and/or two or more different target agents may be administered together, alternately or intermittently in all of the various aspects of the method of the invention.

The present invention also comprehends methods of treating mammalian patients afflicted with cancers, tumors, Kaposi's sarcoma, malignancies, uncontrolled tissue or cellular proliferation secondary to tissue injury, and any other disease conditions responsive to paclitaxel, taxanes, docetaxel, etoposide, prodrugs and derivatives of all the foregoing, paclitaxel 2'-MPM, and docetaxel 2'-MPM with orally administered dosage forms comprising one or more of those agents. Among the types of carcinoma which may be treated particularly effectively with oral paclitaxel, docetaxel, other taxanes, and their prodrugs and derivatives, are hepatocellular carcinoma and liver metastases, and cancers of the gastrointestinal tract, pancreas and lung. Examples of non-cancerous disease conditions which may be effectively treated with these active agents administered orally in accordance with the present invention are uncontrolled tissue or cellular proliferation secondary to tissue injury, polycystic kidney disease and malaria, including chloroquine- and pyrimethamine-resistant malaria parasites (Pouvelle et al., *J. Clin. Invest.*, 44: 413–417, 1994).

The antitumor agents which heretofore were administered only parenterally can now be administered in accordance with the invention by the oral route with sufficient bioavailability to provide pharmacologically active blood concentrations which will be particularly effective in the treatment of patients with primary tumors and metastases. The active ingredients will penetrate the gut wall as a result of the prior and/or concomitant administration of the MDR inhibitors or other enhancers and will be taken up by the portal circulation rapidly, providing a higher local initial concentration of the chemotherapeutic agents in the liver (a far higher local concentration than is currently achieved with IV infusion therapy) than in the general systemic circulation or in most other organs at seven days. Furthermore, it should be noted that the higher levels of paclitaxel in the liver after oral administration may not be reflected in increased plasma levels because of the high first pass effect of the liver. The method of the invention, in selectively producing high blood concentrations of antitumor agents, is particularly valuable in the treatment of liver cancers (e.g., hepatocellular carcinoma and liver metastases), gastrointestinal cancers (e.g., colon, rectal) and lung cancers.

Similarly, after oral administration in accordance with the present invention higher levels of paclitaxel after twenty-four hours are found (upon tissue distribution analysis) in the gastrointestinal tract, pancreas and lung in comparison with the systemic circulation and most other organs. This fact makes orally administered paclitaxel of great value in the treatment of cancers of the G.I. tract, pancreas and lung.

FIGS. 21–24 are especially noteworthy and surprising. Our invention, in certain cases, provides a method for achieving comparable and sometimes higher local tissue concentrations of pacitaxel via the oral route than the intravenous route. This is consistent with a higher volume of distribution of the therapeutic agent. Furthermore, oral administration of an enhancing agent before and immediately after a target agent has been shown (in the case of cyclosporine and paclitaxel, see FIG. 20) to produce a higher concentration of the target agent in the urine than even IV administration. This should make the oral co-administration of enhancing agent with target agent a treatment of choice in the case of patients with tumors or metastases in the genito-urinary tract.

Apart from the higher than previously achieved local concentration of the active ingredients in the liver, the plasma and tissue distribution of the active target agents administered orally with the appropriate enhancing agents as provided in the present invention is remarkably and surprisingly similar to that observed upon IV administration. A series of studies with experimental animals showed that steady state plasma levels of paclitaxel were achieved upon oral co-administration with CsA by the third day of the regimen. The levels of the target agent achieved at steady state were comparable to those achieved in patients by a 96-hour IV infusion of paclitaxel. A 27% response rate was found in taxane-failure patients with metastatic breast cancer treated with a continuous 96-hour infusion every three weeks (Seidman et al., *J. Clin. Oncol.*, 14:1877, 1996). It is believed that similar results can be achieved with the treatment methods of the present invention, without the discomfort, inconvenience and risks of prolonged IV infusions.

Furthermore, and quite significantly, the elimination-phase concentration in the blood of paclitaxel and the other antitumor agents listed above, when administered orally as provided herein, is approximately equal to that achieved with IV administration, and these high, therapeutically effective levels, can be maintained for as long as 8–12 hours after each administration. The increase in urinary excretion of drug after oral administration in the presence of CsA not only supports the enhanced oral absorption of paclitaxel but also provides more drug being delivered to the genito-urinary tract for the treatment of cancers.

Oral dosage forms of the target agents whose bioavailability is increased by the co-administration of the enhancing agents may be in the form of conventional tablets, capsules, caplets, gelcaps, pills, liquids (e.g., solutions, suspensions or elixirs), lozenges and any other oral dosage forms known in the pharmaceutical arts. The liquid preparations may include, for example, paclitaxel or other taxane in a vehicle comprising CREMOPHOR EL or other polyethoxylated castor oil, alcohol and/or a polyoxyethylated sorbitan mono-oleate (e.g., TWEEN® 80, ICI Americas, Inc.). Each dosage form includes an effective amount of a target agent (for example, effective antitumor or antineoplastic amounts of an antitumor or antineoplastic agent) and pharmaceutically inert ingredients, e.g., conventional excipients, vehicles, fillers, binders, disentegrants, solvents, solubilizing agents, sweeteners, coloring agents and any other inactive ingredients which are regularly included in pharmaceutical dosage forms for oral administration. Many such dosage forms and oral vehicles immediately after listings of inactive ingredients therefor are set forth in *Remington's Pharmaceutical Sciences,* 17th edition (1985). Each dosage form also contains a pharmacologically effective amount, for example, an effective antineoplastic or tumor-reducing amount, of one of the target drugs.

Precise amounts of each of the target drugs in the oral dosage forms will vary depending on the age, weight, disease and condition of the patient. For example, paclitaxel dosage forms may contain sufficient quantities of paclitaxel to provide a daily dosage of about 20–1000 mg/m$^2$ (based on patient body surface area) or about 2–30 mg/kg (based on patient body weight) as single or divided (2–3) daily doses. Etoposide oral dosage forms may contain sufficient quantities of etoposide to provide a daily dosage of about 20–200 mg/m$^2$ (based on average or median patient body surface area) as single or divided (2–3) daily doses.

As already indicated, certain of the target agents are commercially available in oral dosage forms, despite their relatively poor or inconsistent oral bioavailability. For example, VEPESID® capsules are available containing 50 mg each of etoposide.

In establishing a treatment regimen for a particular patient treated with the oral, target drug-containing dosage forms of the invention, it is necessary to take into account the increased bioavailability provided by the concomitant and/or prior oral administration of the enhancing agents. For example, although the manufacturer-recommended dosage amount of VEPESID® capsules in the treatment of small cell lung cancer is two times the IV dose rounded to the nearest 50 mg, the increased bioavailability of etoposide provided by pre-and/or substantially simultaneous administration of enhancing agents such as cyclosporins, allows a considerably lower dosage of oral etoposide to be used to provide the same effective blood levels of the drug, with greater duration and stability of action and no increase (and perhaps a decrease) in toxic side effects. With oral administration one can avoid the high peak blood levels which are responsible for some of the toxicities. Based on our experimental data (see FIGS. 18 and 19 and Table 6), which indicate that the oral absorption of etoposide is essentially complete (about 96%) in the presence of cyclosporine, the oral daily dosage range for etoposide in the treatment of testicular cancer should be about 50–100 mg/m$^2$ and in the treatment of small cell lung cancer about 35–50 mg/m$^2$, based on patient body surface area.

Dosing schedules for the treatment method of the present invention, for example, the treatment of paclitaxel-responsive diseases with oral paclitaxel dosage forms co-administered with enhancing agents, can likewise be adjusted to account for the patient's characteristics and disease status. Preferred dosing schedules for administration of oral paclitaxel are (a) the daily administration to a patient in need thereof of 1–3 equally divided doses providing about 20–1000 mg/m$^2$ (based on body surface area), with said daily administration being continued for 1–4 consecutive days each 2–3 weeks, or (b) administration for about one day each week. The former schedule is comparable to use of a 96-hour paclitaxel infusion every 2–3 weeks, which is considered by some a preferred IV treatment regimen. A preferred dosing schedule for oral administration of etoposide co-administered with enhancing agents is the daily administration to a patient in need thereof of 1–3 equally divided doses providing about 50–100 mg/m$^2$ (based on body surface area) in the treatment of patients with testicular cancer and about 35–50 mg/m$^2$ as a daily dose in the treatment of small cell lung cancer, with the daily administration being continued for 5–21 days in each case and with a period of about 2–3 weeks in between each course of treatment.

Oral administration of powerful chemotherapeutic agents in accordance with the invention may actually decrease toxic side effects in many cases as compared with currently utilized IV therapy. Rather than producing a sudden and rapid high concentration in blood levels as is usually the case with an IV infusion, absorption of the active agent through the gut wall (promoted by the enhancing agents), provides a more gradual appearance in the blood levels and a stable, steady-state maintenance of those levels at or close to the ideal range for a long period of time.

Pursuant to another aspect of the invention, combination oral dosage forms are provided which contain fixed quantities of at least one enhancing agent and at least one target agent. For example, such dosage forms can consist of tablets, capsules, caplets, gelcaps, pills, liquids, lozenges and any other conventional oral dosage forms containing as active ingredients an effective oral bioavailability enhancing amount of an antitumor or anti-neoplastic agent, as well as suitable inactive ingredients. One such combination product includes from about 0.1 to about 15 mg/kg of one or more of cyclosporins A, D, C, F and G, dihydro CsA, dihydro CsC and acetyl CsA together with about 20 to about 1000 mg/m$^2$ (based on average patient body surface area) of paclitaxel, docetaxel, other taxanes or paclitaxel or docetaxel derivatives such as paclitaxel 2'-MPM or docetaxel 2'-MPM. Another such dosage form includes about 0.1 to about 15 mg/kg of cyclosporine or cyclosporin D or F together with about 20 mg/m$^2$ to 200 mg/m$^2$ of etoposide.

The co-administration of enhancing agents with the target drugs promotes not only the oral bioavailability of those agents but also enables their use in the treatment of tumors at sites highly protected by MDR, e.g., the testes and the brain. Another aspect of the present invention is, thus, a method of delivering antitumor drugs to tumor sites protected by MDR through the oral co-administration of enhancing agents and the antitumor agents, making it possible to treat brain tumors such as glioblastoma multiforme.

Yet another aspect of the present invention is a method of delivering an active paclitaxel metabolite to a disease site at therapeutic levels to treat paclitaxel-responsive diseases. The major in vivo metabolites of paclitaxel have been identified, particularly the following hydroxylated paclitaxel metabolites A, B and C:

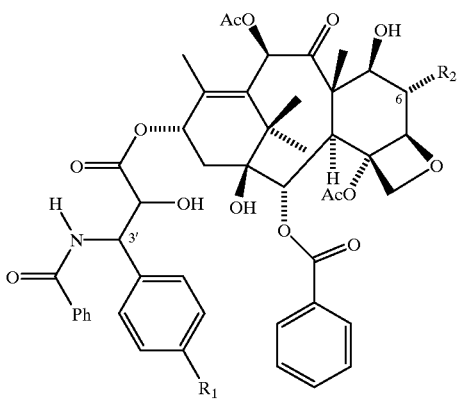

A: $R_1 = H$, $R_2 = OH$; B: $R_1 = OH$, $R_2 = H$; C: $R_1 = OH$, $R_2 = OH$
(Paclitaxel: $R_1 = H$, $R_2 = H$)

In certain in vitro tests metabolite B shown above (also referred to in the literature as metabolite M4) has been found to have a higher therapeutic index (ratio of toxic concentration level to effective concentration level) than paclitaxel in some human tumor cell lines. The invention possibly enables delivery of enhanced amounts of metabolite B and other active metabolites of paclitaxel to tumor sites because upon oral administration all of the administered paclitaxel will pass through the liver and undergo metabolism by liver microsomes, yielding more of each metabolite in the systemic circulation than is achieved with IV administration.

An additional aspect of the invention relates to kits to be used in the treatment of mammalian patients suffering from conditions responsive to any pharmacologically active target agents whose oral absorption and bioavailability is increased by an enhancing agent. These kits include one or more oral dosage forms of at least one enhancing agent and one or more oral dosage forms of at least one target agent, or one or more dosage forms which comprise both.

By way of illustration, a kit of the invention may include one or more tablets, capsules, caplets, gelcaps or liquid formulations containing cyclosporine or ketoconazole, and one or more tablets, capsules, caplets, gelcaps or liquid formulations containing paclitaxel or etoposide in dosage amounts within the ranges described above. Such kits may be used in hospitals, clinics, physician's offices or in patients' homes to facilitate the co-administration of the enhancing and target agents. The kits should also include as an insert printed dosing information for the co-administration of the enhancing and target agents.

The subject kits may also include combinations of different enhancing agents and/or combinations of target agents. For example, a kit may include oral dosage forms respectively containing a cyclosporin and ketoconazole as enhancing agents, with paclitaxel alone as the target agent or with a combination of paclitaxel and another antitumor drug. The second target agent should be (like paclitaxel) a drug that exhibits poor oral bioavailability but with co-administration of enhancing agents can achieve therapeutically effective blood levels upon oral administration. The target agent may co-exist with the enhancing agent in the same dosage form or may be in a separate dosage form.

The following examples illustrate various aspects of the invention and demonstrate the unexpected, very substantial increases in the oral absorption of target agents achieved. These examples are not intended, however, to limit the invention in any way or to set forth specific enhancing or target agents, dosage ranges, testing procedures or other parameters which must be used exclusively to practice the invention.

EXAMPLE 1

Eighteen (18) healthy Sprague Dawley rats, all weighing from 225–275 grams and approximately six to eight weeks old, were randomly divided into three groups of six animals. The first group of six rats received a single IV administration of paclitaxel at a dose of 9 mg/kg. The second group received a single oral dose of paclitaxel at 9 mg/kg. The third group received a single oral dose of cyclosporine at 5 mg/kg, and one hour later the same group received an oral dose of 5 mg/kg cyclosporine and 9 mg/kg paclitaxel.

Blood samples were collected from the tail vein of each rat at 0.5, 1, 2, 3, 4 and 6 hours after the paclitaxel dose. In the case of the IV-treated rats of the first group, an additional blood sample was taken at eight hours after the paclitaxel dose. The individual samples were centrifuged and the serum was separated. For each time interval, the six samples per group were composited to produce a single representative sample. All samples were assayed for unchanged paclitaxel by LC/MS with a lower limit of quantitation of 50 pg/ml.

Figure 1:
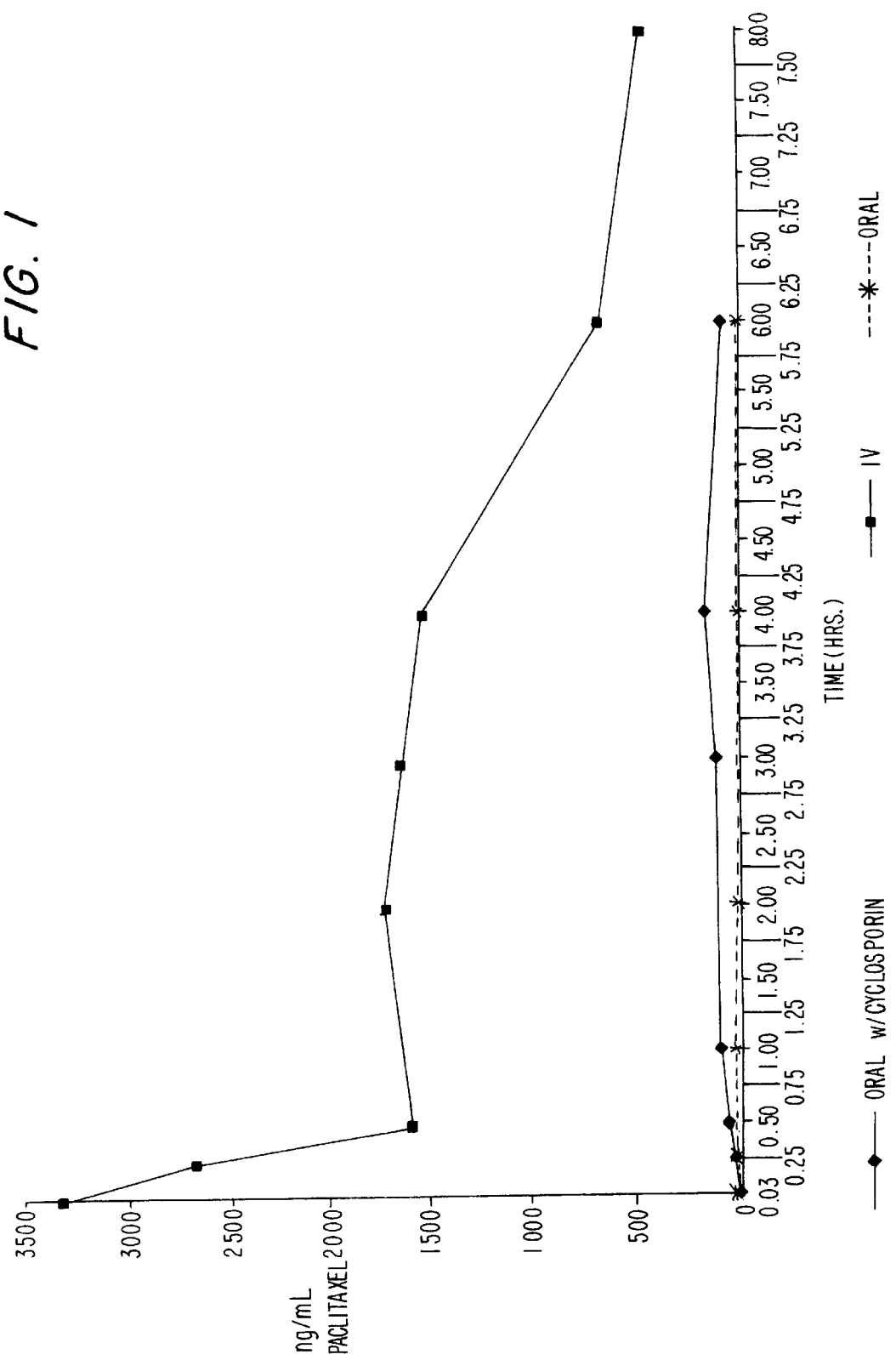
FIG. 1 is a graph reflecting the levels of paclitaxel in serum samples taken over a period of 6–8 hours from three groups of rats: one group administered only paclitaxel by intravenous administration, a second group administered only oral paclitaxel and a third group administered oral paclitaxel with oral cyclosporin A (hereinafter referred to as cyclosporine or CsA) doses prior to and immediately after the paclitaxel dose.
Figure 2:
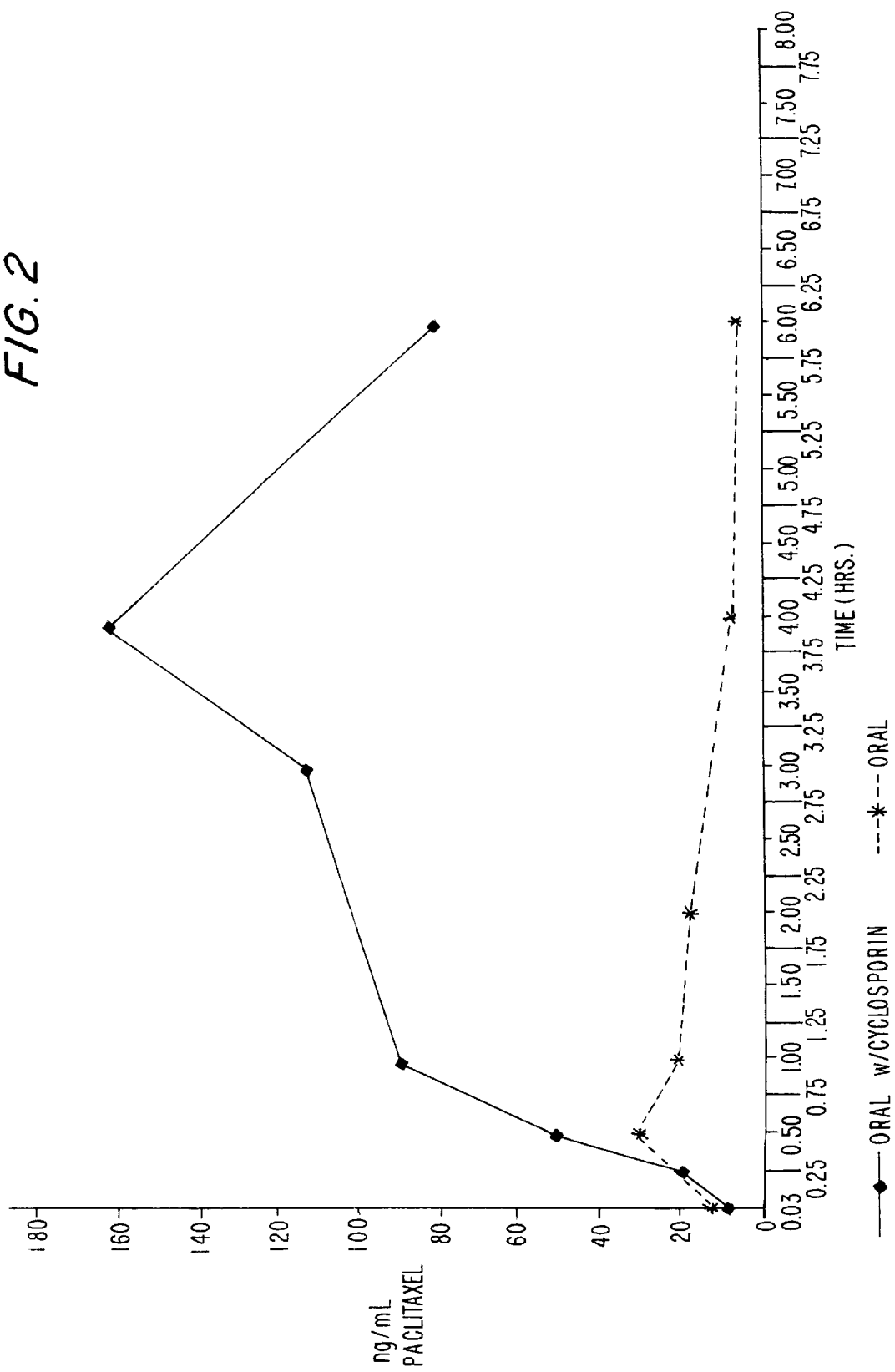
FIG. 2 is a graph comparing the levels of paclitaxel in serum taken from two of the three groups of rats reflected in FIG. 1: the group administered oral paclitaxel alone and the group administered oral paclitaxel with prior and concomitant doses of oral cyclosporine.

The results of the study are graphically illustrated in FIGS. 1 and 2. FIG. 1 compares all three groups of rats while FIG. 2 compares only the second and third groups which received oral paclitaxel. It may be seen that in the absence of cyclosporine, the bioavailability of the paclitaxel in serum was less than 1% but it rose to 6–7% in the third group which received cyclosporine one hour prior to a cyclosporine/paclitaxel combined dose.

The following Table 2 sets forth data regarding the area under the curve (AUC) values determined for the three groups of rats. These data indicate that the AUC value over six hours in the case of the third group of rats receiving both cyclosporine and paclitaxel was almost eight times the AUC for the second group of rats receiving only oral paclitaxel.

TABLE 2

| Paclitaxel Absolute Bioavailability | | |
|---|---|---|
| $AUC_{0-6hr}$ IV (ng.hr/mL) | $AUC_{0-6hr}$ PO (ng.hr/mL) | Absolute F |
| 9230* | 80 | 0.9% |
| Paclitaxel Interaction with Cyclosporin | | |
| $AUC_{0-6hr}$ PO (ng.hr/mL) | $AUC_{01\ 6hr}$ PO with Cyclosporin (ng.hr/mL) | Relative F*** |
| 80 | 629 | 786% |

*AUC value which does not include 1-hr sample point
**F = $[AUC_{PO}/AUC_{IV}] \times 100$
***F = $[AUC_{PO\ with\ Cyclosporin}/AUC_{PO}] \times 100$

EXAMPLE 2

Forty (40) healthy Sprague Dawley rats with the same characteristics as those used in the study described in Example 1 were randomly divided into four groups of ten each labeled Groups A, F, G and H. The following Table 3 indicates the treatment provided to each of the test groups and the time intervals for each dosage administration.

TABLE 3

| Group | No. of Rats | Time (Hour) | Treatment | Dose (mg/kg) | Route of Administration |
|---|---|---|---|---|---|
| A | 10 | 0 | cyclosporine | 5 | oral |
|   |    | 1 | paclitaxel | 9 | oral |
|   |    | 1 | cyclosporine | 5 | oral |
| F | 10 | 0 | cyclosporine | 5 | oral |
|   |    | 1 | paclitaxel | 9 | oral |
| G | 10 | 0 | cyclosporine | 5 |   |
|   |    | 3 | paclitaxel | 9 | IV |
| H | 10 | 0 | paclitaxel | 9 | IV |

Blood samples were collected from the tail vein of each rat at 0.25, 0.5, 1, 2, 3, 4, 5, 6, 8, 12 and 24 hours after paclitaxel administration. After appropriate treatment of the samples and the creation of one composite sample for each group, the plasma from each sample was assayed for unchanged paclitaxel.

Figure 3:
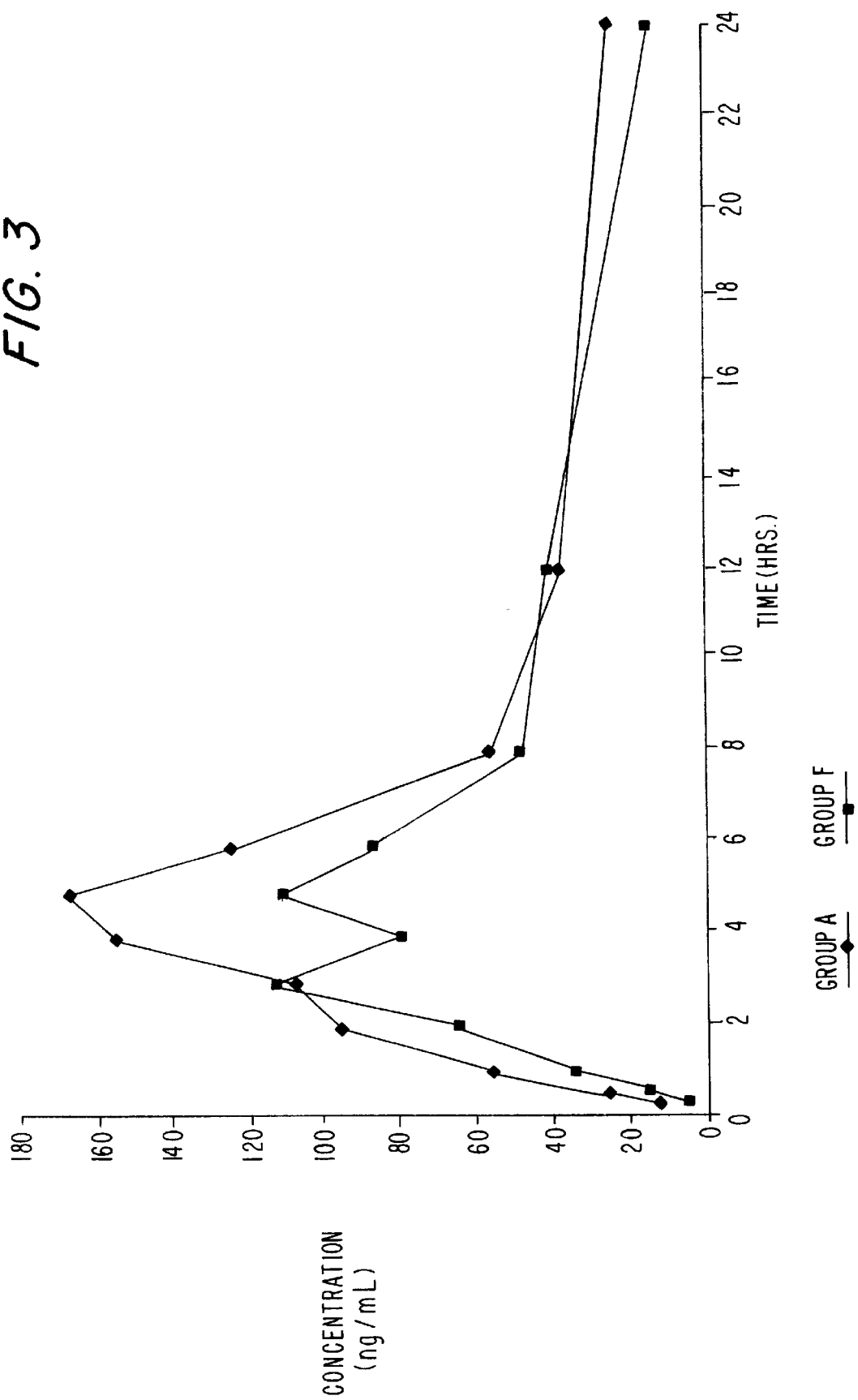
FIG. 3 is a graph reflecting the levels of paclitaxel in plasma samples taken over a period of 24 hours from two groups of rats: one group (A) administered cyclosporine orally one hour prior to the combination of cyclosporine plus oral paclitaxel and the second group (F) administered oral cyclosporine alone one hour prior to oral paclitaxel.
Figure 4:
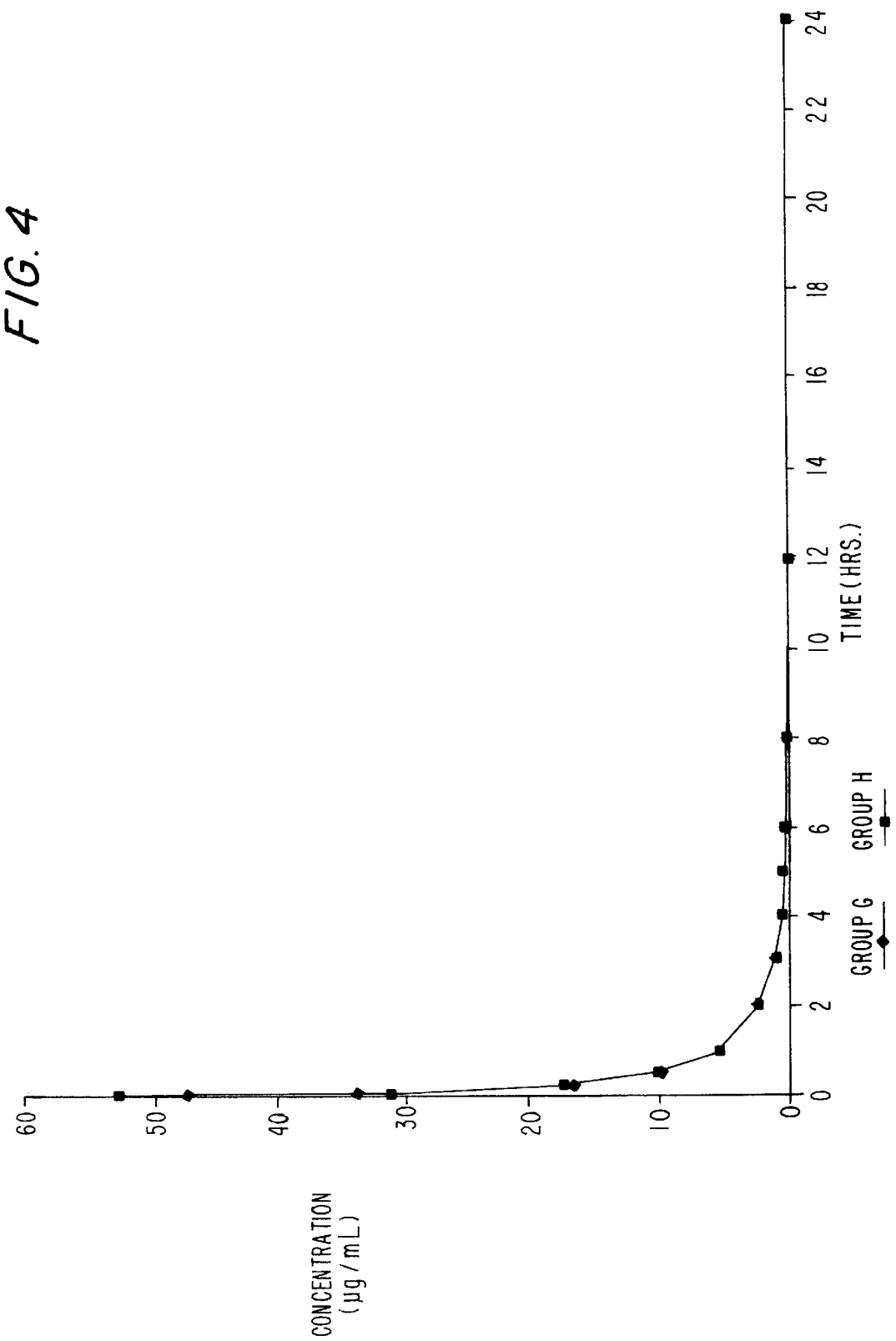
FIG. 4 is a graph reflecting the levels of paclitaxel in plasma samples from two groups of rats: one group (G) administered paclitaxel IV 3 hours after an oral dose of cyclosporine and the second group (H) administered only paclitaxel IV.

FIGS. 3 and 4 graphically illustrate the results of this study. In FIG. 3 a comparison is shown between the concentration levels achieved over time in Group A, which received a cyclosporine pre-dose and a combined paclitaxel-cyclosporine dose one hour later, and Group F, which received a cyclosporine pre-dose and then only oral paclitaxel one hour later. FIG. 4 reflects a comparison between the results achieved with Groups G and H, both of which received paclitaxel IV but with Group G receiving a pre-dose of oral cyclosporine three hours before the paclitaxel. As indicated in FIG. 4, the two groups exhibited essentially the identical levels of paclitaxel in plasma at the same time intervals.

Table 4 sets forth the AUC data for the four groups of rats in this study. While the AUC values for Groups G and H were essentially the same, the AUC value for Group A was 25–30% higher than that for Group F, indicating the value of providing both cyclosporine pre-treatment and co-administration of cyclosporine with paclitaxel.

TABLE 4

Bioavailability of Paclitaxel in Plasma

| Treatment | $AUC_{0-t}$ | F (%) |
|---|---|---|
| IV (Group H) | 24280 |  |
| IV + CsA Oral[a] (Group G) | 24137 | 99.4 |
| Oral + CsA* (Group F) | 1097 | 4.5 |
| Oral + CsA** (Group A) | 1393 | 5.7 |

[a] 3 hr prior to paclitaxel
*1 hr pretreatment with CsA
**1 hr pretreatment and simultaneously with paclitaxel

EXAMPLE 3

Eighteen (18) healthy Sprague Dawley rats with the same characteristics as those used in the study described in Example 1 were randomly divided into three groups of six rats, Groups A, B and C. Group A was administered radio-labeled paclitaxel IV; Group B received $^3$H-radiolabeled paclitaxel orally; and Group C received an oral dose of cyclosporine followed one hour later by a combined oral dose of cyclosporine and radiolabeled oral paclitaxel.

Blood samples were collected from the tail veins of each rat at the same time intervals as described in Example 2. The samples were kept in the form of whole blood. In addition, urine samples were taken from each rat 4–24 hours post-paclitaxel dose. The blood and urine samples were analyzed for radioactivity.

Figure 6:
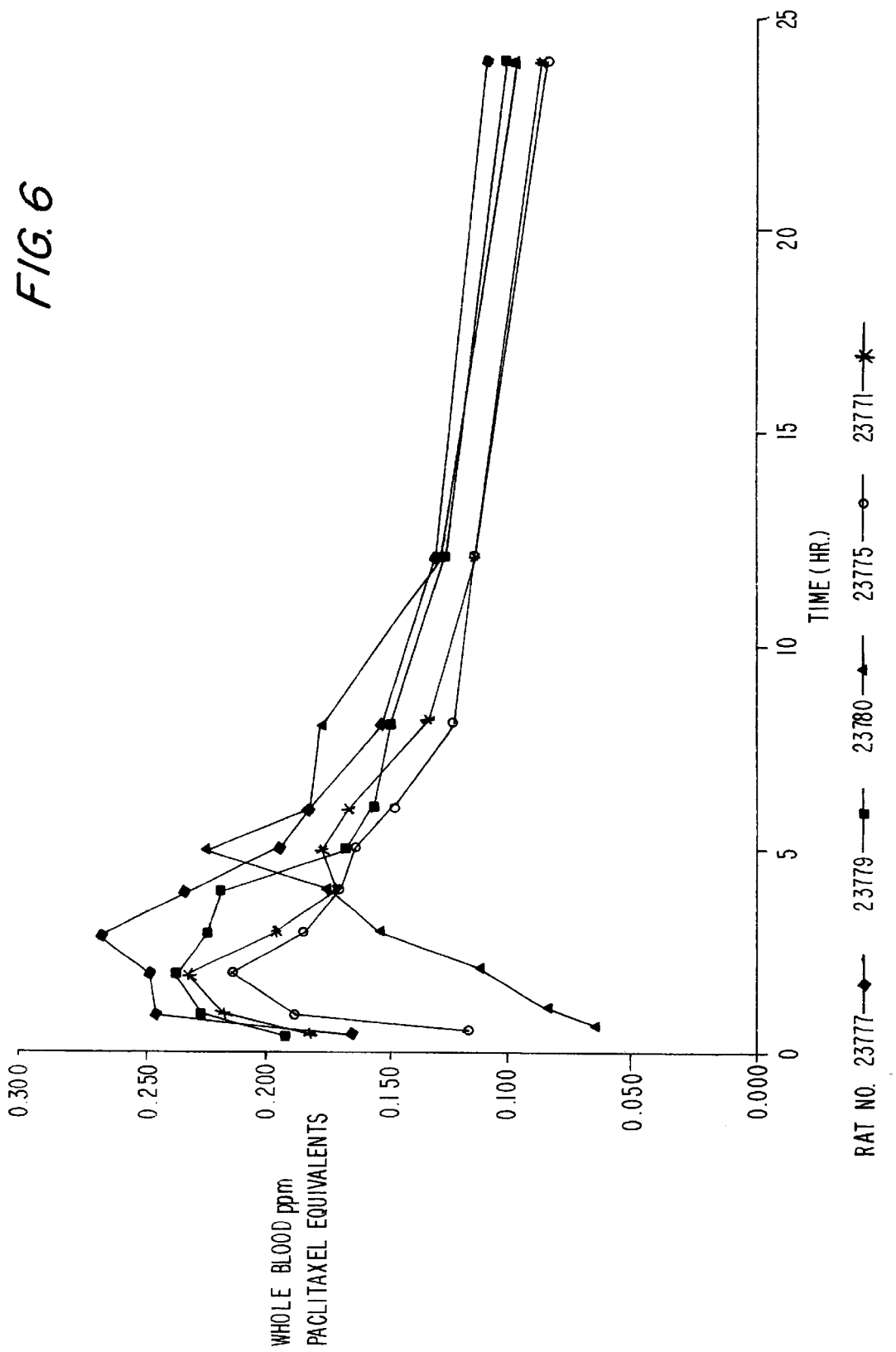
FIG. 6 is a graph reflecting the levels of radioactivity detected in whole blood samples taken from the individual rats in Group B (defined with respect to FIG. 5).
Figure 7:
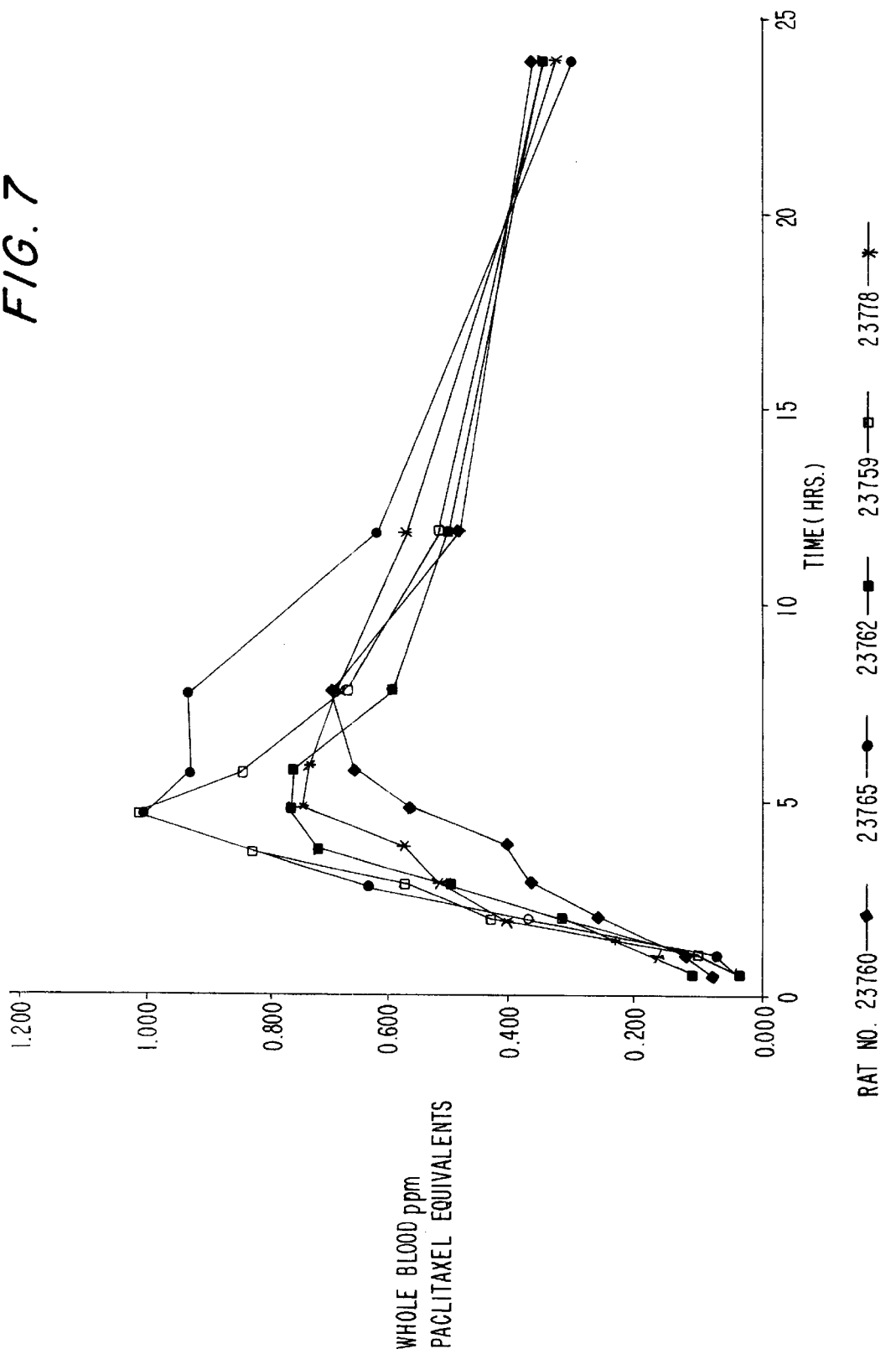
FIG. 7 is a graph reflecting the levels of radioactivity detected in whole blood samples taken from the individual rats in Group C (defined with respect to FIG. 5).
Figure 7B:
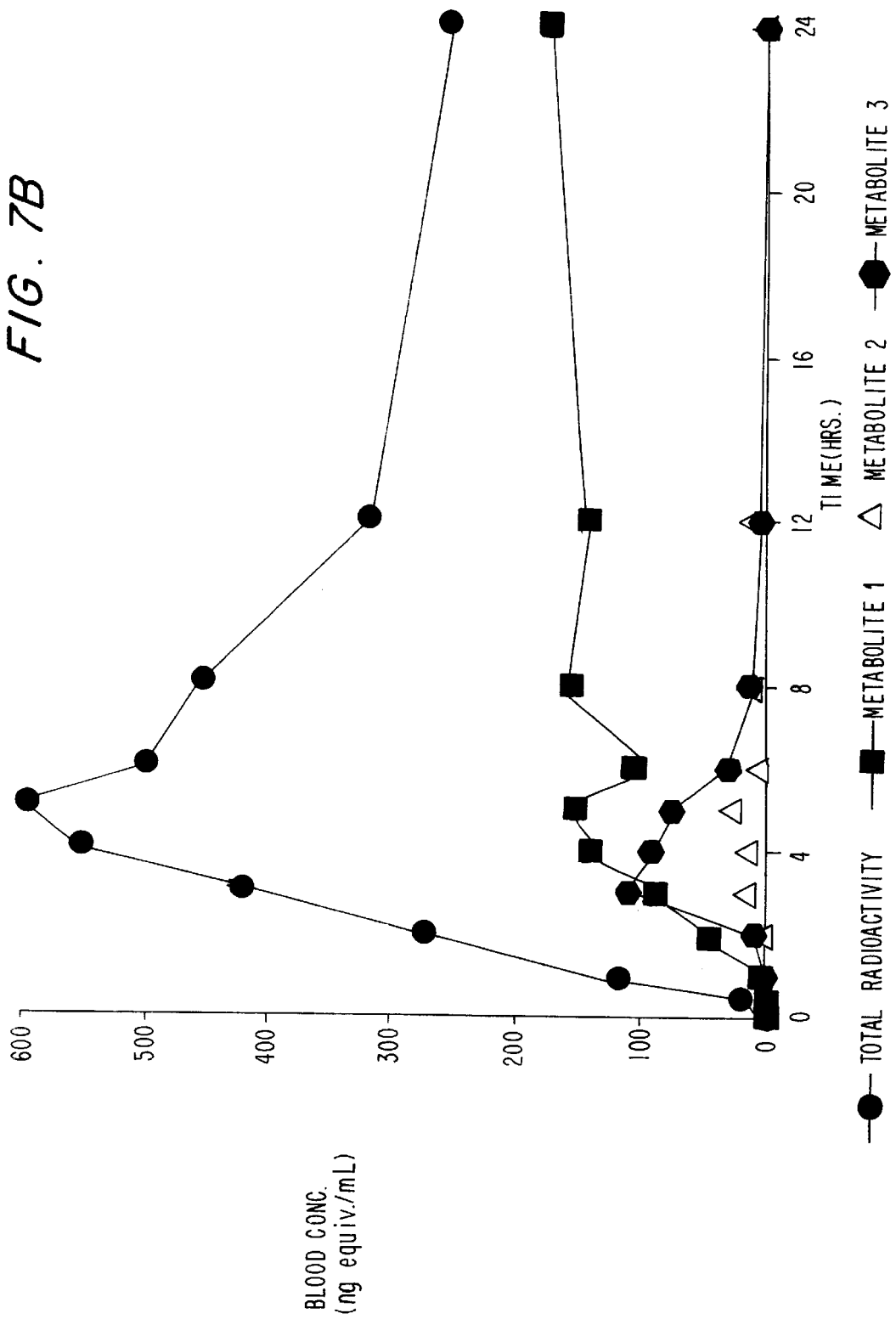
FIG. 7B is a graph reflecting the levels of total radioactivity and paclitaxel metabolites 1, 2 and 3 detected in whole blood samples taken from the group of 10 rats defined with respect to FIG. 7A over a period of 24 hours.

A comparison of the paclitaxel levels in the whole blood samples from Groups A, B and C is set forth in FIG. 5. Comparisons of the levels for the individual members of Groups B and C are set forth in FIGS. 6 and 7, respectively.

In this study, the oral absorption of radioactivity (expressed as paclitaxel equivalents) in whole blood was about 10% in the absence of cyclosporine (Group B) and about 40% with concomitant cyclosporine administration (Group C). This was determined by measuring the AUC of blood radioactivity after intravenous and oral radiolabeled paclitaxel. The bioavailability of paclitaxel was not determined formally in this study because that would require assaying for unchanged drug at each time point. At one time point, though, the radioactivity was extracted from plasma and after standard HPLC it appeared that at least 32% of the radioactivity in the plasma was unchanged paclitaxel. The radioactivity profile from the HPLC-plasma extract of Group C animals, demonstrating predominantly one peak (which is paclitaxel), is shown in FIG. 28. Set forth below in Table 5 are AUC, $C_{max}$, $T_{max}$, and other data generated by this study.

TABLE 5

Total Radioactivity for Paclitaxel in Blood/Urine and % of Radioactivity Extracted as Paclitaxel in Blood

| PK Parameter | IV (A) | PO (B) | PO + CSA** (C) |
|---|---|---|---|
| $AUC_{0-24}$ (μg eq × hr/ml) | 32.8 | 3.2 | 12.1 |
| $C_{max}$ (μg eq/ml) | ND | 0.21 | 0.82 |
| $T_{max}$ (hr) | — | 2 | 5 |
| % Dose in urine (4–24 hr) | 2.2 | 1.9 | 8.3 |
| % Paclitaxel* | ND | 7.8*** | 32*** |

*% as paclitaxel from extracted RA at 4-hr sample.
**CsA given 1 hr prior to and simultaneously with paclitaxel.
***These numbers are lower estimates based upon the incomplete extraction procedure.

TABLE 5A

Absorption of total radioactivity after oral administration of $^3$H-Paclitaxel with/without Cyclosporin (CsA) in rats (n =10)

| PK Parameters | Paclitaxel IV | Paclitaxel Oral | Paclitaxel Oral + CsA |
|---|---|---|---|
| $AUC_{0-24hr}$ (μg equiv.hr/mL) | 23.8 | 1.4 | 8.1 |
| $AUC_{0-\infty}$ (μg equiv.hr/mL) | 27.4 | 4.5 | 15.0 |
| F (%) based on $AUC_{0-24hr}$ |  | 5.9 | 34.0 |
| F (%) Based on $AUC_{0-\infty}$ |  | 16.4 | 54.7 |

Paclitaxel Dose = 9 mg/kg
CsA (5 mg/kg 1 hr prior to and concomitantly with paclitaxel)
F = $AUC_{oral}/AUC_{iv}$

TABLE 5B

Pharmacokinetic Parameters of Paclitaxel after Oral Administration with/without Cyclopsorine in Rats (n = 10)

| PK Parameters | IV Dose | PO Dose | PO + CsA |
|---|---|---|---|
| $AUC_{0-24hr}$ (μg.hr/mL) | 20.43 | 0.314 | 4.27 |
| $AUC_{0-\infty}$ (μg.hr/mL) | 21.02 | 0.349 | 5.41 |
| F (%) |  | 1.7 | 25.7 |
| CL (mL/hr/Kg) | 429 | 440 | 430 |
| V (mL/Kg) | 4236 | 5029 | 5958 |
| $t_{1/2}$ (hr) | 6.8 ($r^2$ = 0.95) | 8.1 ($r^2$ = 0.78) | 9.6 ($r^2$ = 0.96) |

CL = F * Dose/AUC; Dose = 9 mg/kg; F = $AUC_{oral}/AUC_{iv}$

In rats that were treated in the manner described in Example 3, AUC for total radioactivity was determined.

Based on the ratio of AUCoral/AUCiv to infinity, oral absorption in the presence of cyclosporine rose to 54.7% compared to 16.4% in the absence of cyclosporine (Table 5a). Using a similar analysis for unchanged paclitaxel in blood, bioavailability of paclitaxel was 25.7% in the presence of cyclosporine and 1.7% in the absence of cyclosporine (Table 5b). Body clearance was surprisingly similar among the three treatment groups. Volume of distribution of paclitaxel was enhanced about 50% more in the group that received cyclosporine and oral paclitaxel compared to the IV paclitaxel group.

In Examples 4–5 the following study design was utilized: Sprague-Dawley rats with the same characteristics as those used in the study described in Example 1 were divided into three groups of three male rats each. All of the rats were fasted 12–14 hours prior to dosing. At the end of the fasting period, those rats receiving enhancing agents were administered those agents, and one hour later received a dose of radiolabeled ($^3$H) paclitaxel (9 mg/kg) with concomitant doses of enhancing agent. The rats not receiving enhancing agents were administered the radiolabeled paclitaxel after fasting.

Blood was collected from each animal at 0.5, 1, 2, 3, 4, 5, 6, 7, 8, 12 and 24 hours following the paclitaxel dosing. Urine was collected from 4–24 hours post dose. Total radioactivity in blood and urine was then determined for each rat and mean values were calculated for each group.

EXAMPLE 4

Three groups of rats were administered, respectively, 10 mg/kg of verapamil orally, 5 mg/kg of progesterone orally and 10 mg/kg of dipyridamole orally as enhancing agents, both alone and one hour later with an oral dose of paclitaxel. A graphical comparison of the whole blood concentration-time profile (measured as concentration equivalents versus time) determined for the three groups is set forth in FIG. 8. The data reflect roughly similar results with the use of verapamil and dipyridamole as enhancing agents, with markedly lower bioavailability achieved with progesterone.

Figure 9:
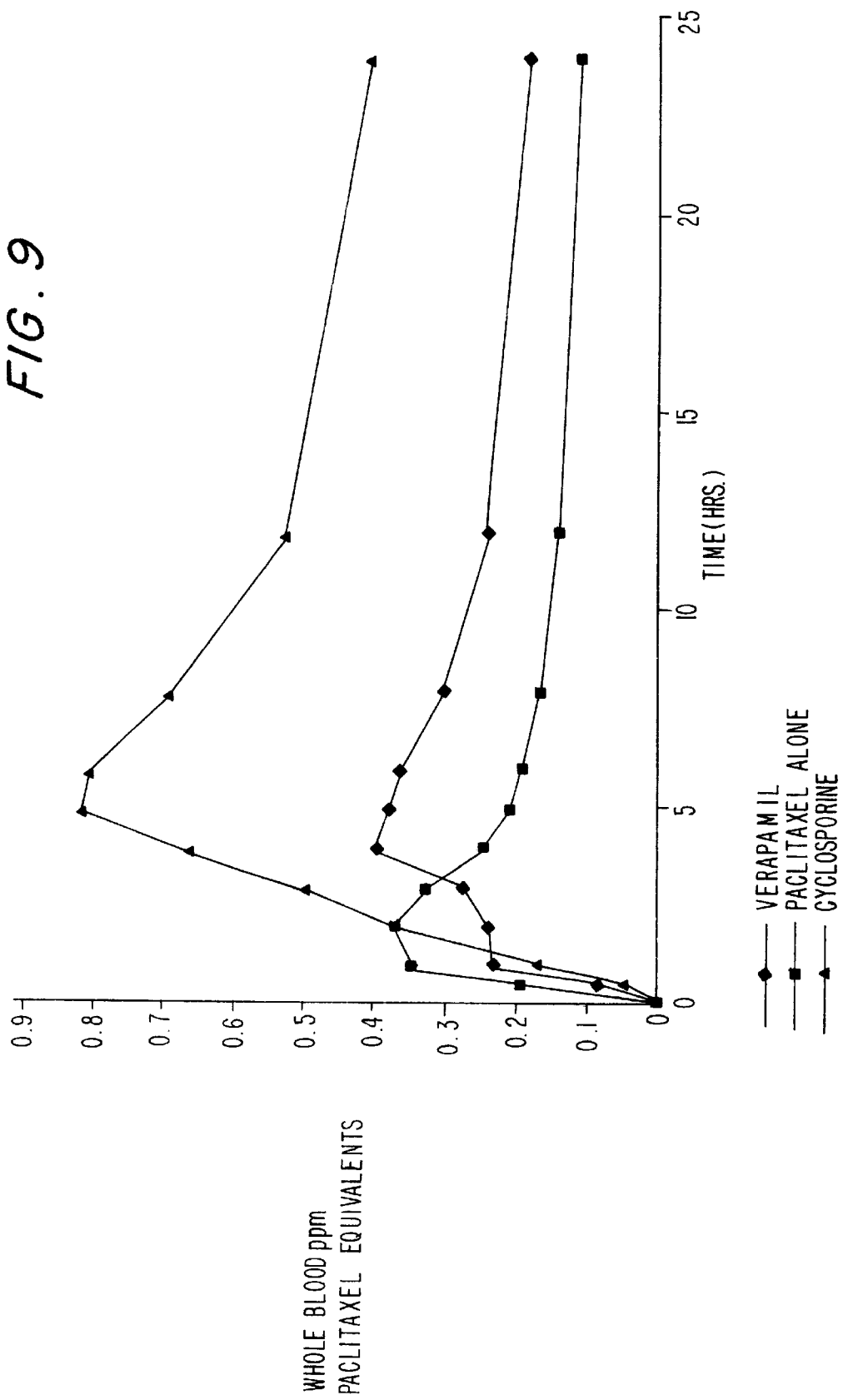
FIG. 9 is a graph reflecting the levels of radioactivity detected in whole blood samples taken over a period of 24 hours from the rats of the first group defined with respect to FIG. 8 (administered 10 mg/kg verapamil orally), a group of rats administered oral radiolabeled paclitaxel alone and a group of rats administered cyclosporine orally one hour prior to and again immediately after radiolabeled oral paclitaxel.

FIG. 9 sets forth a graphical comparison between the concentration-time profile of paclitaxel determined for the group of rats administered verapamil (10 mg/kg) as an enhancing agent with the values determined in a prior study for animals administered oral paclitaxel (9 mg/kg) alone and another group administered oral cyclosporine (5 mg/kg) both one hour before and again immediately after a dose of oral paclitaxel (9 mg/kg). The group receiving cyclosporine achieved far higher blood levels than the other groups throughout almost the entire 24-hour period.

Figure 10:
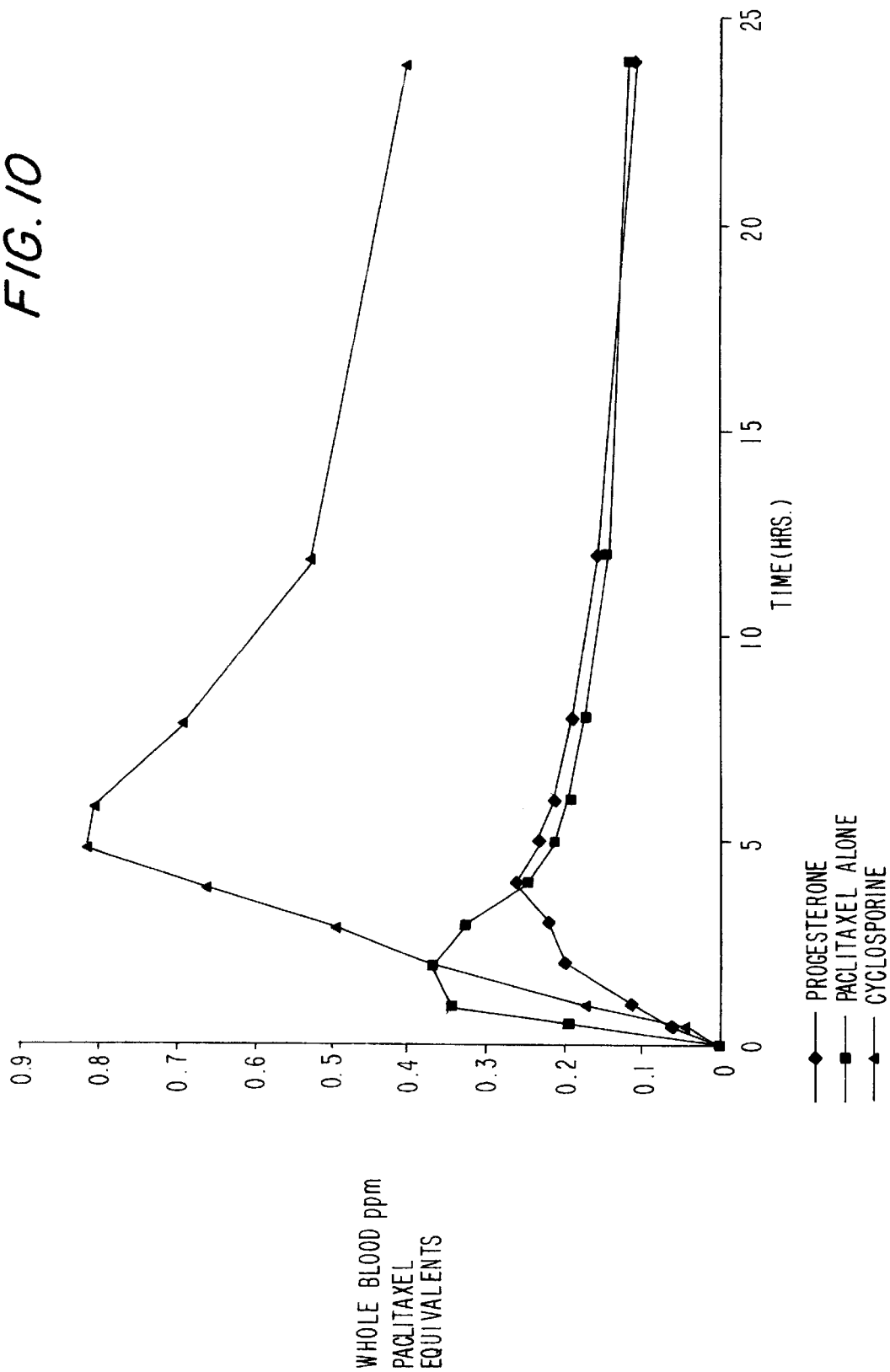
FIG. 10 is a graph reflecting the levels of radioactivity detected in whole blood samples taken over a period of 24 hours from the rats of the second group defined with respect to FIG. 8 (administered progesterone orally), a group of rats administered radiolabeled oral paclitaxel alone and a group of rats administered cyclosporine orally one hour prior to and again immediately after radiolabeled oral paclitaxel.
Figure 11:
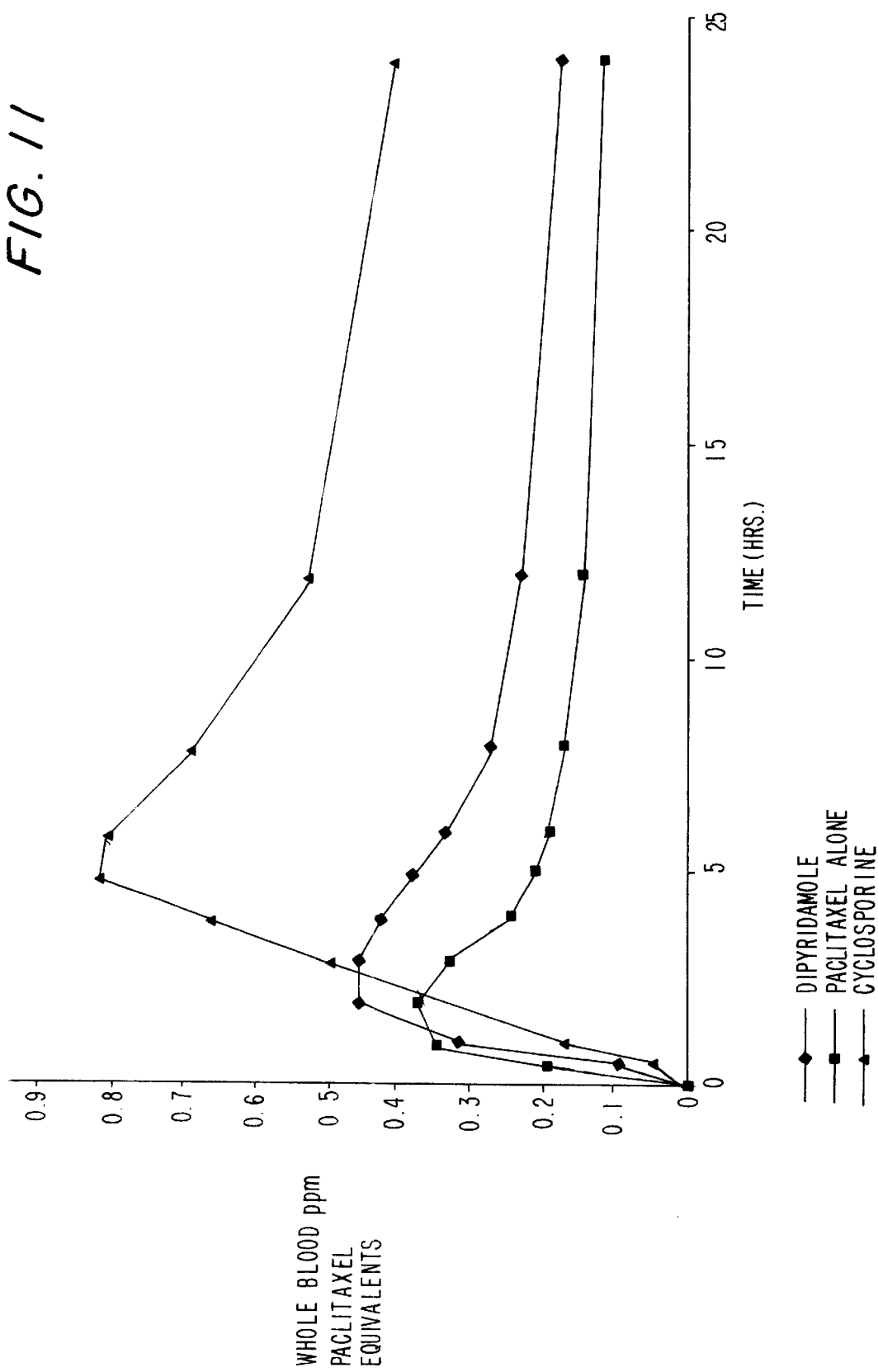
FIG. 11 is a graph reflecting the levels of radioactivity detected in whole blood samples taken over a period of 24 hours from the rats of the third group defined with respect to FIG. 8 (administered dipyridamole orally), a group of rats administered radiolabeled oral paclitaxel alone and a group of rats receiving cyclosporine orally one hour prior to and again immediately after radiolabeled oral paclitaxel.

FIGS. 10 and 11 represent parallel graphical comparisons to FIG. 9, but with the values for the progesterone-administered group shown in FIG. 10 and the dipyridamole group shown in FIG. 11 in place of the verapamil group of FIG. 9.

EXAMPLE 5

Three groups of rats were administered, respectively, 100 mg/kg of verapamil orally, 5 mg/kg of megestrol acetate orally and 50 mg/kg of ketoconazole orally as enhancing agents, both alone and one hour later with an oral dose of radiolabeled paclitaxel. A graphical comparison of the whole blood concentration-time profile (measured as concentration equivalents versus time) determined for the three groups is set forth in FIG. 12. The data reflect roughly similar results for verapamil and megestrol acetate as enhancing agents, with markedly higher bioavailability achieved with ketoconazole in the first 12 hours.

FIG. 13 sets forth a graphical comparison between the concentration-time profile of radioactivity determined for the group of rats administered verapamil (100 mg/kg) as an enhancing agent with the values determined in a prior study for animals administered oral paclitaxel (9 mg/kg) alone and another group administered oral cyclosporine (5 mg/kg) both one hour before and again immediately after a dose of oral radiolabeled paclitaxel (9 mg/kg).

FIGS. 14 and 15 represent parallel graphical comparisons to FIG. 13, but with the values for the megestrol acetate-administered group shown in FIG. 14 and the ketoconazole group shown in FIG. 15 in place of the verapamil group of FIG. 13.

FIG. 16 sets forth graphical comparisons between the concentration-time profiles of radioactivity determined for the group of rats administered 10 mg/kg of verapamil in Example 4 and the group administered 100 mg/kg of verapamil in Example 5.

FIG. 17 sets forth graphical comparisons between the concentration-time profiles of radioactivity determined for the group of rats administered 5 mg/kg of progesterone in Example 4 and the group administered 5 mg/kg of megestrol acetate in Example 5.

In both FIGS. 16 and 17 there are also shown the same profiles reflected in FIGS. 13–15 for study groups receiving oral radiolabeled paclitaxel alone and oral radiolabeled paclitaxel immediately after and one hour after 5 mg/kg of cyclosporine.

Exploration of dose-response data for cyclosporine was performed. Increasing the dose to 10 mg/kg and 20 mg/kg one hour before and concomitantly with paclitaxel resulted in oral absorption of radioactivity to about 45%. This can be contrasted with the findings for ketoconazole in which doses of up to 50 mg/kg were given one hour before and concomitantly with paclitaxel and resulted in no further increase in oral absorption of radioactivity (see FIGS. 17A and 17B).

The mean pharmacokinetic parameters for the study groups of animals discussed in Examples 4 and 5 are set forth in Table 6.[3]

[3]The study of Example 4 is identified in Table 6 as protocol NP951202, and the study of Example 5 is identified as protocol NP960101.

The data generated by the studies of Examples 4 and 5 and reflected in Table 6 and FIGS. 8–17B clearly indicate the efficacy of cyclosporine as an oral bioavailability enhancing agent and its superiority to high or low dose verapamil, progesterone or megestrol acetate, particularly in the first 12 hours after paclitaxel dosing. They also indicate that ketoconazole, while not as effective as cyclosporine, also has significant activity in promoting the oral absorption of paclitaxel.

TABLE 6

Mean Pharmacokinetic Parameters For NP951202 and NP960101

| Study Protocol | Treatment | Dose/Route (mg/kg) | AUC0–24 (ug × hr/mL) | F % | t½ (hour) | Cmax (ug*eq/mL) |
|---|---|---|---|---|---|---|
| NP951001 | Paclitaxel only | 9/IV | 32.04 | | 20.15 | 37 |
| | Paclitaxel only | 9/PO | 3.24 | 10.1 | 18.86 | 0.21 |
| | Cyclosporin | 5/PO(C), 9/PO(P) 5/PO(C) | 12.02 | 37.5 | 14.51 | 0.82 |
| NP951202 | Verapamil | 10/PO(V), 9/PO(P) 10/PO(V) | 6.34 | 19.8 | 24.4 | 0.78 |
| | Progesterone | 5/PO(Pro), 9/PO(P) 5/PO(Pro) | 3.78 | 11.8 | 20.0 | 0.26 |
| | Dipyridamole | 10/PO(D), 9/PO(P) 10/PO(D) | 6.18 | 19.3 | 26.6 | 0.46 |
| NP960101 | *Verapamil (animals died) | 100/PO(V), 9/PO(P) 100/PO(V) | NA | NA | NA | 0.44 |
| | Megace | 5/PO(M), 9/PO(P) 5/PO(M) | 5.19 | 16.2 | 23.1 | 0.44 |
| | Ketoconazole | 50/PO(K), 9/PO(P) 50/PO(K) | 8.03 | 25.1 | 9.23 | 0.69 |

EXAMPLE 6

Three groups of three male rats each were fasted 16–18 hours prior to dosing. At the end of the fasting period one group of rats was administered an oral dose of 5 mg/kg of cyclosporine. One hour later, that group was administered 5 mg/kg of cyclosporine orally with 1 mg/kg of $^3$H-radiolabeled etoposide orally. The other two groups were administered after fasting only 1 mg/kg of $^3$H-etoposide IV and 1 mg/kg H-etoposide orally, respectively. The procedures for blood and urine collection and for determining total radioactivity were the same as in Examples 4 and 5 except that blood was taken at two additional intervals from the group receiving etoposide IV, at 0.033 and 0.25 hours. The resultant data are set forth in Table 7.

FIGS. 18 and 19 set forth graphically the mean whole blood concentration-time profile of etoposide determined for the three study groups. In FIG. 18 the ordinate scale runs from 0–1 etoposide concentration equivalents (ppm), while in FIG. 19 the ordinate scale runs from 0–0.2 etoposide equivalents (ppm) to more clearly illustrate the differences between the values achieved for the three groups.

The data set forth in Table 7 and FIGS. 18 and 19 demonstrate the efficacy of cyclosporine as an oral bioavailability enhancing agent for etoposide, particularly in the first 12 hours after dosing.

TABLE 7

Mean Pharmacokinetic Parameters For NP960102

| Study Protocol | Treatment | Dose/Route (mg/kg) | AUC0–24 (ug × hr/mL) | F (%) | t½ (hour) | Cmax (ug*eq/mL) |
|---|---|---|---|---|---|---|
| NP960102 | | | | | | |
| Grp A | Etoposide only | 1/IV | 1.08 | | 26.5 | 2.16 |
| Grp B | Etoposide only | 1/PO | 0.61 | 56.5 | 19.1 | 0.03 |
| Grp C | CsA, Etoposide + CsA | 5/PO(C), 1/PO(P) 5/PO(C) | 1.04 | 96.3 | 18.1 | 0.12 |

EXAMPLE 7

In another series of studies, three groups of three male rats each were fasted 16–18 hours prior to dosing. At the end of the fasting period one group of rats was administered an oral dose of ketoconazole (2 mg/kg). One hour later, that group was administered 2 mg/kg of ketoconazole orally with 1 mg/kg of $^3$H-radiolabeled etoposide orally. The other two groups were treated in the same fashion except that they were administered 10 and 50 mg/kg of ketoconazole, respectively, after fasting prior to and just after $^3$H-etoposide orally. The procedures for blood collection and for determining total radioactivity were the same as in Examples 4 and 5. The resultant data are set forth in Table 7A. Thus, in contrast to the effect that cyclosporine had on nearly doubling the oral absorption of paclitaxel-derived radioactivity, ketoconazole administered over a wide range of doses did not enhance the oral absorption of etoposide compared to etoposide alone

TABLE 7A

NP960501

| | | | | | | | |
|---|---|---|---|---|---|---|---|
| Grp A | Etoposide + Ketoconazole | 1/EO(2/Keto) | 0.54 | 50.39 | 0.026 | 1 | 47.8 |
| Grp B | Etoposide + Ketoconazole | 1/EO(10/Keto) | 0.69 | 63.95 | 0.032 | 24 | −91.5 |
| Grp C | Etoposide + Ketoconazole | 1/EO(50/Keto) | 0.64 | 58.91 | 0.060 | 4 | 38.1 |

EXAMPLE 7

An excretion balance study for paclitaxel in rats was conducted. Three groups of 4–5 male rats each were fasted 12–14 hours prior to dosing. At the end of the fasting period one group of rats was administered an oral dose of 5 mg/kg of cyclosporine. One hour later, that group was administered 5 mg/kg of cyclosporine orally with 9 mg/kg of radiolabeled paclitaxel orally. The other two groups were administered after fasting only 9 mg/kg of radiolabeled paclitaxel IV and 9 mg/kg of radiolabeled paclitaxel orally.

The urine and feces were collected from each animal at the following intervals: 0–2, 2–4, 4–8, 8–12, 12–24, 24–36, 36–48, 48–72, 72–96, 96–120, 120–144, and 144–168 hours post-dose. Tissue collection was performed at 168 hours post-dose. The procedure for determining total radioactivity was the same as in Examples 4 and 5.

FIG. 20 sets forth a graphical comparison of the mean cumulative percentage of dose of paclitaxel detected in the feces and urine of the test animals over the 168-hour period. The group of rats administered cyclosporine both before and with the oral paclitaxel exhibited a markedly lower percentage of dose in feces than the other two groups and a significantly higher percentage of dose in urine, indicating that substantially more of the oral paclitaxel diffused through the gut wall and entered the systemic circulation of the animals in the cyclosporine treated group. In addition, the fact that the percentage of dose in urine was significantly higher for the rats administered oral cyclosporine and paclitaxel in comparison with the IV-paclitaxel group indicates that the concomitant oral administration caused a higher concentration of radioactivity to pass through the genitourinary tract.

FIGS. 21–24 are bar graphs reflecting the mean ppm values of paclitaxel detected in a variety of tissues harvested from the rats in the three study groups, Group A representing the animals administered paclitaxel IV, Group B representing those administered paclitaxel orally and Group C representing the cyclosporine-treated group. These graphs show that the levels of paclitaxel found in the various tissues from the rats in Group C were roughly comparable to the levels observed in the rats from Group A that received paclitaxel IV, except in the liver where the level of paclitaxel was more than twice as high in the cyclosporine treated group as in the group administered paclitaxel IV. The levels detected in the tissues of the rats of Group B (administered oral paclitaxel alone) were quite low, in most instances far less than half of the levels in either of the other groups.

The data resulting from this study are set forth in Tables 8 and 9.

TABLE 8

EXCRETION BALANCE STUDY FOR PACLITAXEL IN RAT
Radioactivity in Urine, Feces and Tissues Expressed as %
of Dose (Mean Values)

| SAMPLE | GROUP A | GROUP B | GROUP C |
|---|---|---|---|
| Urine | 9.160 | 6.660 | 18.350 |
| Feces | 79.660 | 84.410 | 61.250 |
| Tissues | 1.710 | 0.600 | 1.430 |
| Total | 90.530 | 91.670 | 81.030 |

TABLE 9

EXCRETION BALANCE STUDY FOR PACLITAXEL IN RAT
Radioactive Residues in Tissues Expressed as PPM (Mean Values)

| SAMPLE | GROUP A | GROUP B | GROUP C |
|---|---|---|---|
| Brain | 0.101 | 0.029 | 0.096 |
| Heart | 0.085 | 0.025 | 0.088 |
| Lung | 0.143 | 0.030 | 0.136 |
| Liver | 0.237 | 0.074 | 0.566 |
| Kidney | 0.180 | 0.032 | 0.119 |
| Muscle | 0.079 | 0.025 | 0.080 |
| GI Tract | 0.083 | 0.021 | 0.055 |
| Testes | 0.346 | 0.037 | 0.217 |
| Pancreas | 0.078 | 0.018 | 0.080 |
| Carcass | 0.143 | 0.053 | 0.099 |
| Bone | 0.035 | 0.007 | 0.034 |
| Spleen | 0.101 | 0.024 | 0.083 |
| Prostate | 0.08 1 | 0.022 | 0.090 |
| S. Vesicles | 0.121 | 0.024 | 0.094 |
| Blood | 0.112 | 0.034 | 0.106 |
| Plasma | 0.126 | 0.038 | 0.124 |

EXAMPLE 9

Another tissue distribution study for paclitaxel in rats was conducted. Two groups of 10 male rats each were fasted 12–14 hours prior to dosing. At the end of the fasting period one group of rats was administered an oral dose of 5 mg/kg cyclosporine. One hour later, that group was administered 5 mg/kg of cyclosporine orally with 9 mg/kg of radiolabeled paclitaxel orally. The other group was administered after fasting only 9 mg/kg of radiolabeled paclitaxel IV.

Tissue collection was performed at 24 hours post-dose. The procedure for determining total radioactivity was the same as in Examples 4 and 5.

Table 9A reflects the ppm values of paclitaxel-derived radioactivity detected in a variety of tissues harvested from the rats in the two study groups. One group representing the animals administered paclitaxel IV and the second group representing those administered paclitaxel with cyclosporine given 1 hour prior to and immediately after paclitaxel. The levels of paclitaxel found in the various tissues from the cyclosporine-treated rats were roughly comparable to the levels observed in the rats given paclitaxel IV, except in the spleen, pancreas and gastrointestinal tract where the level of paclitaxel was about twice as high in the cyclosporine-treated group as in the group administered paclitaxel IV.

A comparison of unchanged paclitaxel concentrations in various organs after IV paclitaxel alone compared to oral paclitaxel given in the presence of cyclosporine is shown in Table 9B. Higher concentrations of unchanged paclitaxel after oral administration were found in the lungs and gastrointestinal tract, compared to the IV route of administration.

TABLE 9A

Ratio of ppm Paclitaxel Equivalents in Tissue for Group C and A (Mean Values)

| Tissue | Oral Dose with CsA | IV Dose | Ratio |
| --- | --- | --- | --- |
| Brain | 0.267 | 0.284 | 0.94 |
| Heart | 1.166 | 0.576 | 2.92 |
| Lung | 2.076 | 1.230 | 1.69 |
| Liver | 4.328 | 3.685 | 1.17 |
| Kidney | 2.325 | 1.259 | 1.85 |
| Muscle | 0.951 | 0.639 | 1.49 |
| GI Tract | 11.282 | 5.673 | 1.99 |
| Testes | 0.435 | 0.804 | 0.54 |
| Pancreas | 1.999 | 0.911 | 2.19 |
| Carcass | 1.043 | 0.858 | 1.22 |
| Bone | 1.057 | 0.612 | 1.73 |
| Spleen | 3.089 | 1.180 | 2.62 |
| Prostate | 2.212 | 1.660 | 1.33 |
| Seminal Vesicles | 1.891 | 2.693 | 0.70 |
| Blood | 0.373 | 0.401 | 0.93 |
| Plasma | 0.370 | 0.347 | 1.07 |

TABLE 9B

Extraction of Radioactivity from Various Tissues

| Group | Tissue | Tissue ppm $^3$H | % of $^3$H Characterized by HPLC | Tissue Paclitaxel ppm | % of $^3$H Characterized as Paclitaxel |
| --- | --- | --- | --- | --- | --- |
| IV | Liver | 3.7 | 75.9 | 1.34 | 36.2 |
|  | Lung | 1.3 | 79.5 | 0.82 | 63.1 |
|  | GI Tract | 5.4 | 78.1 | 1.55 | 28.7 |
| Oral with CsA | Liver | 4.5 | 75.5 | 0.93 | 20.7 |
|  | Lung | 2.3 | 91.3 | 1.42 | 61.7 |
|  | GI Tract | 10.6 | 91.4 | 5.17 | 48.8 |
| 1.0 ppm Spike | Liver | 1.0 | 102.7 | 0.77 | 77.0 |

EXAMPLE 10

The procedure of Examples 4 and 5 was followed, but the three groups of three male rats each were orally administered respectively 5 mg/kg doses of cyclosporin D, cyclosporin G and cyclosporin A, both alone and one hour later immediately after an oral dose of 9 mg/kg radiolabeled paclitaxel. FIG. 25 sets forth a graphical comparison of the whole blood concentration-time profiles for radioactivity determined in these three test groups. While all three cyclosporins showed substantial activity in promoting oral absorption of paclitaxel, the cyclosporin D, which has the least immunosuppressive activity (Jeffery, Clin. Biochem, 24:15–21 (1991)), of the three cyclosporins tested, exhibited the greatest bioavailability enhancing activity.

EXAMPLE 11

A number of studies were conducted wherein the procedure used in Examples 4 and 5 was followed, and groups of three male rats each were orally administered 5–10 mg/kg of various cyclosporins alone and then again one hour later immediately after an oral dose of 9 mg/kg radiolabeled paclitaxel. Table 10 sets forth a comparison of AUC and % absorption from these studies, each identified by a protocol number beginning with the prefix "NP".

TABLE 10

AUC & % Absorption of Various Cyclosporins

| Protocol | Cyclosporin | Dose (mg/kg) | AUC$_{0-24}$ ($\mu$g · eg.hr/ml) | % Absorption |
| --- | --- | --- | --- | --- |
| NP 960507 | A | 2 × 5 | 13.91 | 42.1 |
| 960503 | A | 2 × 10 | 10.17 | 33.6 |
| 960503 | A | 2 × 20 | 14.63 | 48.3 |
| NP 960507 | Acetyl A | 2 × 5 | 8.39 | 25.4 |
| 960507 | C | 2 × 5 | 11.39 | 34.5 |
| 960507 | E | 2 × 5 | 5.96 | 18.0 |
| 960507 | H | 2 × 5 | 6.00 | 18.1 |
| 960507 | U | 2 × 5 | 5.02 | 15.2 |
| NP 960103 | D | 2 × 5 | 15.92 | 48.2 |
| 960103 | G | 2 × 5 | 13.22 | 40.0 |
| NP 960704 | D | 2 × 10 | 14.23 | 43.1 |
| 960704 | F | 2 × 10 | 11.99 | 36.3 |
| NP 960605 | F | 2 × 5 | 8.99 | 27.2 |
| 960605 | Dihydro A | 2 × 5 | 8.5 | 25.7 |
| NP 960801 | Leu$^4$ | 2 × 5 | 7.38 | 24.6 |
| 960801 | Dihydro C | 2 × 5 | 13.09 | 45.1 |

EXAMPLE 12

The procedure of Examples 4 and 5 was followed, but the three groups of three male rats each were orally administered respectively a 5 mg/kg dose of cyclosporin A, 50 mg/kg ketoconazole and 5 mg/kg cyclosporin A plus 50 mg/kg ketoconazole, both alone and one hour later immediately after an oral dose of 9 mg/kg radiolabeled paclitaxel. A graphical comparison of the results achieved is set forth in FIG. 26. The group receiving the combination of ketoconazole and cyclosporin A unexpectedly exhibited significantly higher blood radioactivity levels over almost the entire 24-hour period than the groups receiving only one of these enhancing agents.

EXAMPLE 13

The procedure of Examples 4 and 5 was followed, but the three groups of three male rats each were orally administered respectively a 100 mg/kg dose of captopril both alone and two hours later immediately after an oral dose of 9 mg/kg radiolabeled paclitaxel, a 5 mg/kg dose of cyclosporine alone and again one hour later immediately after a 9 mg/kg oral dose of radiolabeled paclitaxel, and a 9 mg/kg oral dose of radiolabeled paclitaxel alone. A graphical comparison of the results achieved is set forth in FIG. 27.

The aforedescribed studies produced several previously unknown and unexpected findings which are all of great significance to the clinical management of many diseases, particularly various types of cancer:

1. Certain MDR (P-glycoprotein) inhibitors as well as other agents not known to be MDR inhibitors can be administered orally to effectively enhance the oral bioavailability of treatment agents which have until now been administered only parenterally because therapeutic blood levels cannot be attained upon oral administration.

2. Co-administration of the enhancing agents of the invention with target drugs having poor oral bioavailability can achieve sustained blood levels of the target drugs comparable to that achieved with IV infusion therapy but with a less abrupt initial rise in blood levels and hence less likelihood of toxic side effects.

3. The oral co-administration of the enhancing agents and target drugs increases the proportionate concentration of the target agent in the liver, lung and gastrointestinal tract in comparison with IV administration, making the novel method of administration particularly useful in the treatment of liver tumors and metastases.

4. Administering an enhancing agent orally prior to administration of concomitant oral doses of enhancing agent and target drug increases the oral bioavailability of the target drug to a significantly higher degree than co-administration of the enhancing and target agents with no preadministration of enhancing agent. This results in plasma levels of the target drug reaching therapeutic levels.

5. Cyclosporins, particularly cyclosporins A, D and F, are much more effective agents for enhancing the bioavailability of antitumor agents than MDR inhibitors such as verapamil and progesterone. Ketoconazole has clinically significant oral bioavailability-enhancing activity, but less than the cyclosporins.

In general, the various aspects of the invention enable and make practical for the first time the administration of oral dosage forms of widely used pharmaceutical agents, particularly anticancer drugs such as paclitaxel related taxanes and etoposide, which until now could only be administered effectively or reliably by IV infusion. The use of such oral dosage forms in the clinical management of cancers will promote patient comfort, convenience, compliance and safety and result in cost savings to patients, hospitals and government and private medical insurers.

In addition, the teachings of the invention set forth herein provide information regarding the selection of target and enhancing agents as well as timing, schedules and dosing. This information and the methods and compositions of the invention provide clinicians with procedures for sustaining therapeutic levels of drugs which require narrow windows of drug concentrations while avoiding unnecessary and frequently harmful peaks and valleys in blood concentration levels. In addition, increased volume of distribution of paclitaxel in the presence of cyclosporine, suggests more drug would be available for anti-tumor activity.

Apart from multi-drug resistance resulting from P-glycoprotein encoded by the MDR1 gene, there is another gene which has recently been found to confer a multi-drug resistance phenotype in certain laboratory systems: the gene for multi-drug-resistance-associated protein, MRP (e.g., Zaman et al., *Proc. Natl. Acad. Sci. USA,* 91:8822–8826, 1994).

Less is known about this new gene and its protein product, a 190-kd membrane bound glycoprotein. Although both the MRP and MDR1 genes encode membrane glycoproteins that can act as transporters of multiple drugs, there are differences in function, likely substrates, and prognostic significance between these two genes. For example MRP but not MDR1 gene expression is a good marker of poor clinical outcome in patients with neuroblastomas. The putative function of the MRP-related proteins is to serve as an efflux pump for glutathione S-conjugates. Thus, molecules that undergo glutathione conjugation would be susceptible to the action of the MRP-related system.

The oral bioavailability of pharmacologically active agents (or exposure of the tumor to such agents) which are subject to resistance by MRP-related proteins can be enhanced by orally co-administrating MRP inhibitors. The preferred embodiment of this method of increasing oral bioavailability is the oral administration of one or more MRP inhibitors prior to the oral co-administration of one or more MRP inhibitors and one or more target agents subject to MRP-related resistance.

Examples of target agents of this type include (but are not limited to) vinca alkaloids (e.g., vincristine), anthracyclines, epidophyllotoxins (e.g., etoposide) and various taxanes. Examples of MRP inhibitors that can increase oral bioavailability of target agents include, but are not limited to, cyclosporins, ketoconazole and the experimental drugs VX-710 and VX-853 (Vertex Pharmaceuticals, Inc., Cambridge, Mass.). The structures of VX-710 and VX853, as well as many related compounds, are disclosed in U.S. Pat. No. 5,192,773.

Another method of improving the oral bioavailability of agents subject to MRP-related resistance is to co-administer with those agents glutathione or substances which form glutathione-conjugated products which would interfere with the functioning of the MRP system and enhance the absorption of the target agents from the gut, or increase the systemic exposure of agents subjected to MRP-related transport.

Yet another system capable of conferring multi-drug resistance is the so-called Lung Resistance-Related Protein (LRP), because it was first identified in a multi-drug resistant lung cancer cell line. This protein is the major structural protein of the so-called vault apparatus, a large abundant cytoplasmic ribonucleoprotein particle, which has been conserved from slime mold to man. Inhibition of this system may also positively affect oral bioavailability of certain agents. LRP is found in highest expression in epithelial cells with secretory and excretory functions, as well as in cells chronically exposed to xenobiotics, such as bronchial and intestinal lining cells (Scheffer et al., *Nature Medicine,* 1: 578–582, 1955). Therefore, this system could also serve as a target for enhancing oral bioavailability.

It has thus been shown that there are provided methods, compositions and kits which achieve the various objects of the invention and which are well adapted to meet the conditions of practical use.

As various possible embodiments might be made of the above invention, and as various changes might be made in the embodiments set forth above, it is to be understood that all matters herein described are to be interpreted as illustrative and not in a limiting sense.

What is claimed as new and desired to be protected by Letters Patent is set forth in the following claims.

We claim:

1. A method of increasing the bioavailability upon oral administration to a mammalian patient of a taxane comprising the oral co-administration to the patient of the taxane and an oral bioavailability enhancing agent comprising a cyclosporin.

2. The method of claim 1 wherein the taxane is selected from the group consisting of paclitaxel, metabolites of paclitaxel, docetaxel and prodrugs, and pharmaceutically acceptable salts thereof.

3. The method of claim 1 wherein the enhancing agent is administered either
   a) about 0.5–24 hrs. before,
   b) less than 0.5 hr. before, together with or less than 0.5 hr. after, or
   c) both about 0.5–24 hrs. before and again less than 0.5 hr. before, together with or less than 0.5 hr. after, the administration of the taxane.

4. The method of claim 1 wherein the taxane and the enhancing agent are each administered in separate oral dosage forms.

5. The method of claim 1 wherein the taxane and the enhancing agent are administered together in a combination oral dosage form.

6. The method of claim 1 wherein the taxane composes paclitaxel.

7. The method of claim 1 wherein the taxane comprises docetaxel.

8. The method of claim 1 wherein the patient is administered about 20–1,000 mg/m$^2$ of the taxane based on patient body surface area.

9. The method of claim 1 wherein the patient is administered about 2–30 mg/kg of paclitaxel based on patient body weight.

10. The method of claim 1 wherein the cyclosporin comprises cyclosporin D.

11. The method of claim 1 wherein the patient is administered about 0.1 to about 15 mg/kg of enhancing agent based on patient body weight.

12. The method of claim 1 wherein the enhancing agent comprises cyclosporin A.

13. The method of claim 1 wherein the enhancing agent comprises about 5 mg/kg of cyclosporin A.

14. The method of claim 1 wherein the cyclosporin is selected from the group consisting of cyclosporins A through Z, (Me-lle-4)-cyclosporin, dihydro cyclosporin A, dihydro cyclosporin C and acetyl cyclosporin A and related oligopeptides produced by species in the genus Topycladium.

15. The method of claim 1 wherein the enhancing agent comprises cyclosporin G.

16. The method of claim 1 wherein the enhancing agent comprises a non-immunosuppressive cyclosporin.

17. The method of claim 1 wherein the enhancing agent comprises cyclosporin F.

18. A method of treating a mammalian patient afflicted with a disease responsive to a taxane comprising the oral co-administration to the patient of a taxane and an oral bioavailability-enhancing agent comprising a cyclosporin.

19. The method of claim 18 wherein the disease is a cancer, tumor, neoplastic growth, or uncontrolled tissue or cellular proliferation secondary to tissue injury.

20. The method of claim 18 wherein the disease is selected form the group consisting of ovarian cancer, breast cancer, lung cancer, head and neck carcinomas, hepatocellular carcinoma, liver metastases, genito-urinary and gastrointestinal tract cancer, Kaposi's sarcoma, polycystic kidney disease and malaria.

21. The method of claim 18 wherein the enhancing agent is administered either
   a) about 0.5–24 hrs. before,
   b) less than 0.5 hr. before, together with or less than 0.5 hr. after, or
   c) both about 0.5–24 hrs. before and again less than 0.5 hr. before, together with or less than 0.5 hr. after, the administration of the taxane.

22. The method of claim 18 wherein the taxane and the enhancing agent are administered together in separate dosage forms.

23. The method of claim 18 wherein the taxane and the enhancing agent are administered together in a combination oral dosage form.

24. The method of claim 18 wherein the taxane is selected from the group consisting of paclitaxel, metabolites of paclitaxel, docetaxel and prodrugs and pharmaceutically acceptable salts thereof.

25. The method of claim 18 wherein the taxane comprises paclitaxel.

26. The method of claim 18 wherein the taxane comprises docetaxel.

27. The method of claim 18 wherein the cyclosporin comprises cyclosporin D.

28. The method of claim 18 wherein the patient is administered about 20–1,000 mg/m$^2$ of the taxane based on patient body surface area.

29. The method of claim 18 wherein the patient is administered about 2–30 mg/kg of paclitaxel based on patient body weight.

30. The method of claim 18 wherein the patient is administered about 0.1 to about 15 mg/kg of enhancing agent based on patient body weight.

31. The method of claim 18 wherein the enhancing agent comprises cyclosporin A.

32. The method of claim 18 wherein the enhancing agent comprises about 5 mg/kg of cyclosporin A.

33. The method of claim 18 wherein the cyclosporin is selected from the group consisting of cyclosporins A through Z, (me-lle-4)-cyclosporin, dihydro cyclosporin A, dihydro cyclosporin C, acetyl cyclosporin A, and related oligopeptides produced by species in the genus Topycladium.

34. The method of claim 18 wherein the enhancing agent comprises cyclosporin G.

35. The method of claim 18 wherein the enhancing agent comprises a non-immunosuppressive cyclosporin.

36. The method of claim 18 wherein the enhancing agent comprises cyclosporin F.

37. An oral pharmaceutical dosage form containing a taxane and an oral bioavailability enhancing agent comprising a cyclosporin.

38. The oral pharmaceutical dosage form of claim 37 wherein the taxane is selected from the group consisting of paclitaxel, metabolites of paclitaxel, docetaxel and prodrugs, and pharmaceutically acceptable salts thereof.

39. The dosage form of claim 37 wherein the taxane comprises docetaxel.

40. The dosage form of claim 37 wherein the taxane comprises paclitaxel.

41. The dosage form of claim 37 which contains about 20–1,000 mg/m$^2$ of the taxane based on average or median patient body surface area.

42. The dosage form of claim 37 wherein the taxane comprises about 2–30 mg/kg of paclitaxel based on patient body weight.

43. The dosage form of claim 37 wherein the cyclosporin comprises cyclosporin A or cyclosporin D.

44. The dosage form of claim 37 wherein the cyclosporin comprises (Me-lle-4)-cyclosporin or cyclosporin A.

45. The dosage form of claim 37 which contains about 0.1 to about 15 mg/kg of enhancing agent based on patient body weight.

46. The dosage form of claim 37 wherein the enhancing agent comprises about 5 mg/kg of cyclosporin A.

47. The dosage form of claim 37 which is in a form selected from the group consisting of tablets, capsules, caplets, pills, lozenges and liquid solutions, suspensions or elixirs.

48. The dosage form of claim 37 further comprising a pharmaceutically inert excipient vehicle, filler, binder, disintegrant, solvent, solubilizing agent, sweetener or coloring agent.

49. The dosage form of claim 37 further comprising a polyethoxylated castor oil, alcohol or a polyoxyethylated sorbitan mono-oleate.

50. The dosage form of claim 37 wherein the cyclosporin is selected from the group consisting of cyclosporins A through Z, (Me-lle-4)-cyclosporin, dihydro cyclosporin A, dihydro cyclosporin C, acetyl cyclosporin A and related oligopeptides produced by species in the genus Typycladium.

51. The method of claim 37 wherein the enhancing agent comprises cyclosporin G.

52. The method of claim 37 wherein the enhancing agent comprises a non-immunosuppressive cyclosporin.

53. The method of claim 37 wherein the enhancing agent comprises cyclosporin F.

* * * * *

UNITED STATES PATENT AND TRADEMARK OFFICE
CERTIFICATE OF CORRECTION

PATENT NO. : 6,245,805 B1　　　　　　　　　　　　　　　　　　　　　Page 1 of 1
DATED　　　 : August 20, 2001
INVENTOR(S) : Samuel Broder, Kenneth L. Duchin, and Sami Selim It is certified that error appears in the above-identified patent and that said Letters Patent is hereby corrected as shown below:

Column 3,
Line 64, "provides" should read -- provide --.

Column 12,
Line 44, "Mufti" should read -- MULTI --.

Column 26,
Line 67, after "alone" insert -- . --.

Column 32,
Line 66, "bioavailability enhancing" should read -- bioavailability-enhancing --.

Column 33,
line 19, "composes" should read -- comprises --.

Column 34,
Line 35, "me" should read -- Me --.
Line 45, "bioavailability enhancing" should read -- bioavailability-enhancing --.

Column 35,
Line 8, after "excipient" insert -- , --.

Column 36,
Line 5 and 6, "Typycladium" should read -- *Topycladium* --.

Signed and Sealed this

Eighteenth Day of December, 2001

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

| | |
|---|---|
| PATENT NO. | : 6,245,805 B1 |
| DATED | : June 12, 2001 |
| INVENTOR(S) | : Samuel Broder, Kenneth L. Duchin, and Sami Selim |

It is certified that error appears in the above-identified patent and that said Letters Patent is hereby corrected as shown below:

<u>Column 36,</u>
Lines 7, 9 and 11, "method" should read -- dosage form --.

Signed and Sealed this

Twelfth Day of March, 2002

Attest:

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO.    : 6,245,805 B1
DATED         : June 12, 2001
INVENTOR(S)   : Samuel Broder, Kennth L. Duchin and Sami Selim It is certified that error appears in the above-identified patent and that said Letters Patent is hereby corrected as shown below:

Column 33,
Lines 43 "Topycladium" should read -- Tolypocladium --.

Column 34,
Line 37, "Topycladium" should read -- Tolypcladium --.

Column 35,
Line 5, "suspensions or" should read -- suspensions and --.

Signed and Sealed this

Fifteenth Day of March, 2005

JON W. DUDAS
*Director of the United States Patent and Trademark Office*